(12) United States Patent
Jain et al.

(10) Patent No.: US 12,258,368 B2
(45) Date of Patent: Mar. 25, 2025

(54) DISULFIDE-LINKED REVERSIBLE TERMINATORS

(71) Applicant: CENTRILLION TECHNOLOGY HOLDINGS CORPORATION, Grand Cayman (KY)

(72) Inventors: Moti Jain, Palo Alto, CA (US); Wei Zhou, Palo Alto, CA (US)

(73) Assignee: CENTRILLION TECHNOLOGY HOLDINGS CORPORATION, Grand Cayman (KY)

( * ) Notice: Subject to any disclaimer, the term of this patent is extended or adjusted under 35 U.S.C. 154(b) by 831 days.

(21) Appl. No.: 17/278,958

(22) PCT Filed: Sep. 27, 2019

(86) PCT No.: PCT/US2019/053629
§ 371 (c)(1),
(2) Date: Mar. 23, 2021

(87) PCT Pub. No.: WO2020/069424
PCT Pub. Date: Apr. 2, 2020

(65) Prior Publication Data
US 2022/0048940 A1 Feb. 17, 2022

Related U.S. Application Data

(60) Provisional application No. 62/847,458, filed on May 14, 2019, provisional application No. 62/835,007, (Continued)

(51) Int. Cl.
*C07H 19/10* (2006.01)
*C07H 19/20* (2006.01)
(Continued)

(52) U.S. Cl.
CPC ............. *C07H 19/10* (2013.01); *C07H 21/04* (2013.01); *C12Q 1/6869* (2013.01); *C07H 19/14* (2013.01); *C07H 19/173* (2013.01); *C07H 19/20* (2013.01)

(58) Field of Classification Search
CPC ...... C12Q 1/6869; C07H 19/20; C07H 19/14; C07H 19/10; C07H 19/23; C07H 21/00; C07H 21/02; C07H 21/04
See application file for complete search history.

(56) References Cited

U.S. PATENT DOCUMENTS 11,059,849 B2    7/2021  Ybert et al.
11,180,522 B2 *  11/2021 Jain ..................... C07H 19/10
(Continued)

FOREIGN PATENT DOCUMENTS

CN    101631796 A    1/2010
CN    106117288 A    11/2016
(Continued)

OTHER PUBLICATIONS

Quaedflieg et al., "An Alternative Approach towards the Synthesis of (3'-5') Methylene Acetal Linked Dinucleosides" Tetrahedron Letters vol. 33 No. 21 pp. 3081-3084 (Year: 1992).*

(Continued)

*Primary Examiner* — Eric Olson
(74) *Attorney, Agent, or Firm* — JONES DAY

(57) ABSTRACT

The present disclosure provides methods of sequencing polynucleotides and compounds, compositions useful for sequencing of polynucleotides. The chemical compounds include nucleotides and their analogs which possess a sugar moiety comprising a cleavable chemical group capping the 3'-OH group and a base that is attached to a detectable label through a cleavable linker comprising a disulfide bond. In (Continued)

addition, the disulfide bond(s) can be cleavable by a reducing reagent. In addition, after the disulfide bond(s) is/are cleaved by the reducing reagent, there is no free thiol group linked to the nucleotides. Examples of chemical compounds according to the present disclosure are shown as Formulae (IV) and (V).

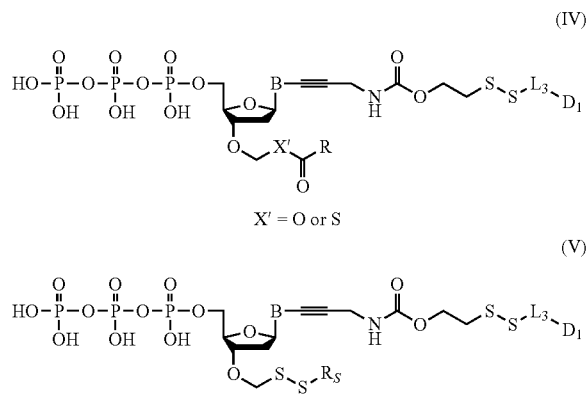

10 Claims, 4 Drawing Sheets

Related U.S. Application Data filed on Apr. 17, 2019, provisional application No. 62/808,413, filed on Feb. 21, 2019, provisional application No. 62/738,627, filed on Sep. 28, 2018.

(51) Int. Cl.
*C07H 21/04* (2006.01)
*C12Q 1/6869* (2018.01)
*C07H 19/14* (2006.01)
*C07H 19/173* (2006.01)

(56) References Cited

U.S. PATENT DOCUMENTS

| 2003/0104437 | A1 | 6/2003 | Barnes et al. |
| 2007/0166705 | A1 | 7/2007 | Milton et al. |
| 2010/0093992 | A1 | 4/2010 | Cherkasov et al. |
| 2016/0355541 | A1* | 12/2016 | Jain ............... C12Q 1/6869 |
| 2017/0130051 | A1* | 5/2017 | Marma ............ C12Q 1/6876 |
| 2017/0211134 | A1 | 7/2017 | Marma et al. |

FOREIGN PATENT DOCUMENTS

| CN | 107074903 A | 8/2017 |
| DE | 102007045173 A1 | 5/2008 |
| WO | WO 2016182984 A1 | 11/2016 |
| WO | WO 2017058953 A1 | 4/2017 |
| WO | WO 2017079498 A2 | 5/2017 |
| WO | WO 2017176677 A1 | 10/2017 |

OTHER PUBLICATIONS

Thillier et al., "Solid-phase synthesis of 5'-triphosphate 2'-5'-oligoadenylates analogs with 3'-O-biolabile groups and their evaluation as RNase L activators and antiviral drugs" Bioorganic & Medicinal Chemistry vol. 21 pp. 5461-5469, DOI: 10.1016/j.bmc.2013.06.008 (Year: 2013).*

International Searching Authority, International Search Report and Written Opinion for International Patent Application No. PCT/US2019/053629 (Pub No. WO 2020069424) mailed Jan. 29, 2020 (10 pages).

Knapp et al., 2011, "Fluoride-cleavable, fluorescently labelled reversible terminators: synthesis and use in primer extension," Chemistry, 17(10):2903-2915.

Turcatti et al., 2008, "A new class of cleavable fluorescent nucleotides: synthesis and optimization as reversible terminators for DNA sequencing by synthesis," Nucleic Acids Res., 36(4):e25 (13 pages).

* cited by examiner 1. dT-terminator 2. dC-terminator 3. dA-terminator 4. dG-terminator X = O or S 1. dT-terminator 2. dC-terminator 3. dA-terminator 4. dG-terminator

DISULFIDE-LINKED REVERSIBLE TERMINATORS

CROSS-REFERENCE TO RELATED APPLICATIONS

This application is a U.S. National Stage Application under 35 U.S.C. § 371 of International Patent Application No. PCT/US2019/053629, filed Sep. 27, 2019, which claims the benefit of U.S. Provisional Patent Application No. 62/738,627, filed Sep. 28, 2018, U.S. Provisional Patent Application No. 62/808,413, filed Feb. 21, 2019, U.S. Provisional Patent Application No. 62/835,007, filed Apr. 17, 2019, and U.S. Provisional Patent Application No. 62/847,458, filed May 14, 2019, the disclosure of each of which is incorporated by reference herein in its entirety.

BACKGROUND

High-throughput sequencing has found application in many areas of modern biology from ecology and evolution, to gene discovery and discovery medicine. For example, in order to move forward the field of personalized medicine, the complete genotype and phenotype information of all geo-ethnic groups may need to be garnered. Having such information may permit physicians to tailor the treatment to each patient.

New sequencing methods, commonly referred to as Next Generation Sequencing (NGS) technologies, have promised to deliver fast, inexpensive and accurate genome information through sequencing. For example, high throughput NGS (HT-NGS) methods may allow scientists to obtain the desired sequence of genes with greater speed and at lower cost. Clinically screening a full genome for an individual's mutations may offer benefits both for pursuing personalized medicine and for uncovering genomic contributions to diseases. However, sometimes the efficiency of HT-NGS is obtained at the cost of accuracy of the sequencing results. In this context, sequencing by synthesis (SBS) methodologies may allow a more accurate determination of the identity of the incorporated base, thereby offering higher fidelity in HT-NGS.

SUMMARY

The present disclosure provides chemical compounds including reversible terminator molecules, i.e. nucleoside and nucleotide analogs which comprise a cleavable chemical group covalently attached to the 3' hydroxyl of the nucleotide sugar moiety. In addition, the reversible terminator molecules comprise a detectable label attached to the base of the nucleotide through a cleavable linker. The cleavable linker comprises a disulfide bond which can be cleaved by a reducing reagent. Then the reducing reagent or a basic reagent can also cleave the cleavable chemical group on the 3' hydroxyl of the nucleotide sugar moiety. The covalent linkage to the 3' hydroxyl is reversible, meaning the cleavable chemical group may be removed by chemical and/or enzymatic processes. The detectable label may optionally be quenchable. The nucleotide analogs may be ribonucleotide or deoxyribonucleotide molecules and analogs, and derivatives thereof. Presence of the covalently bound cleavable chemical group is designed to impede progress of polymerase enzymes used in methods of enzyme-based polynucleotide synthesis.

A first aspect of the present disclosure provides a nucleoside 5'-triphosphate analog according to formula (I):

(I)

or a salt or protonated form thereof, wherein:
X is O, S, or $BH_3$;
LG is $-X'-(C=O)-R_X$ or $-S-S-R_S$;
X' is O or S;
w is 1, 2, 3, 4, or 5;
$R_X$ is H or $C_{1-6}$ alkyl, wherein the $C_{1-6}$ alkyl is unsubstituted or substituted by 1-3 groups selected from the group consisting of F and Cl;
$R_S$ is $C_{1-6}$ alkyl, wherein the $C_{1-6}$ alkyl is unsubstituted or substituted by 1-3 groups selected from the group consisting of F and Cl;
base B is a nucleotide base or an analog thereof;
$L_1$ is a first linker group and $L_1$ is 3-25 atoms in length;
$L_2$ is a second linker group and $L_2$ is and m is 2 or 3;
$L_3$ is a third linker group and $L_3$ is 4-47 atoms in length;
$D_1$ is a detectable label; and
the disulfide bond(s) is/are cleavable by a reducing reagent, thereby after the disulfide bond(s) is/are cleaved by the reducing reagent, there is no free thiol group linked to the base B (and the 3'-O).

A second aspect of the present disclosure provides a nucleoside 5'-triphosphate analog according to formula (II):

(II)

or a salt or protonated form thereof, wherein:
X is O, S, or $BH_3$;
X' is O or S;
w is 1, 2, 3, 4, or 5;
$R_X$ is H or $C_{1-6}$ alkyl, wherein the $C_{1-6}$ alkyl is unsubstituted or substituted by 1-3 groups selected from the group consisting of F and Cl;
base B is a nucleotide base or an analog thereof;
$L_1$ is a first linker group and $L_1$ is 3-25 atoms in length;

$L_2$ is a second linker group and $L_2$ is

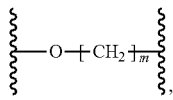

and m is 2 or 3;
$L_3$ is a third linker group and $L_3$ is 4-47 atoms in length;
$D_1$ is a detectable label; and
the disulfide bond is cleavable by a reducing reagent, thereby after the disulfide bond is cleaved by the reducing reagent, there is no free thiol group linked to the base B.

A third aspect of the present disclosure provides a nucleoside 5'-triphosphate analog according to formula (III):

(III)

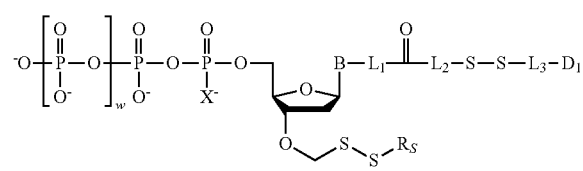

or a salt or protonated form thereof, wherein:
X is O, S, or $BH_3$;
w is 1, 2, 3, 4, or 5;
base B is a nucleotide base or an analog thereof;
$R_S$ is $C_{1-6}$ alkyl, wherein the $C_{1-6}$ alkyl is unsubstituted or substituted by 1-3 groups selected from the group consisting of F and Cl;
$L_1$ is a first linker group and $L_1$ is 3-25 atoms in length;
$L_2$ is a second linker group and $L_2$ is

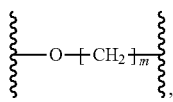

and m is 2 or 3;
$L_3$ is a third linker group and $L_3$ is 4-47 atoms in length;
$D_1$ is a detectable label; and
the disulfide bonds are cleavable by a reducing reagent, thereby after the disulfide bonds are cleaved by the reducing reagent, there is no free thiol group linked to the base B and the 3'-O.

In some embodiments of aspects provided herein, the base B of the nucleoside 5'-triphosphate analog is selected from the group consisting of

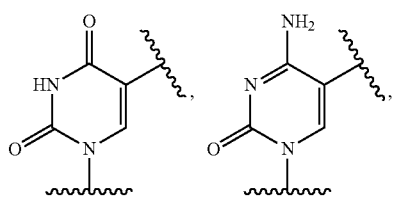

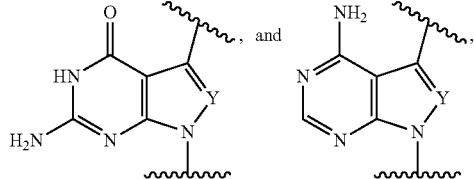

and Y is CH or N.

In some embodiments of aspects provided herein, the nucleoside 5'-triphosphate analog of formulae (I), (II) and (III) is further defined as: $L_1$ comprises alkylene, alkenylene, alkynylene, —O—, —NH—, or combinations thereof. In some embodiments of aspects provided herein, the nucleoside 5'-triphosphate analog of formulae (I), (II) and (III) is further defined as: $L_3$ comprises alkylene, alkenylene, cycloalkylene with a 3-7 membered ring, alkynylene, arylene, heteroarylene, heterocyclene with a 5-12 membered ring comprising 1-3 atoms of N, O or S, —O—, —NH—, —S—, —N($C_{1-6}$ alkyl)-, —C(=O)—, —C(=O)NH—, or combinations thereof.

In some embodiments of aspects provided herein, the nucleoside 5'-triphosphate analog of formulae (I), (II) and (III) is further defined as:
$L_1$ is

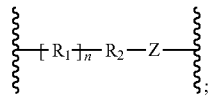

n is 0 or 1;
$R_1$ is

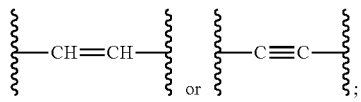

$R_2$ is

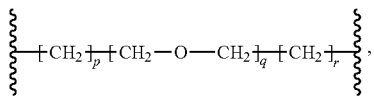

wherein p is 0-3, q is 0-12, and r is 1-3; and
Z is O or NH.

In some embodiments of aspects provided herein, the nucleoside 5'-triphosphate analog of formulae (I), (II) and (III) is further defined as:
$L_3$ is

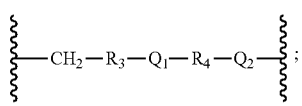

$Q_1$ and $Q_2$ are independently selected from the group consisting of a bond,

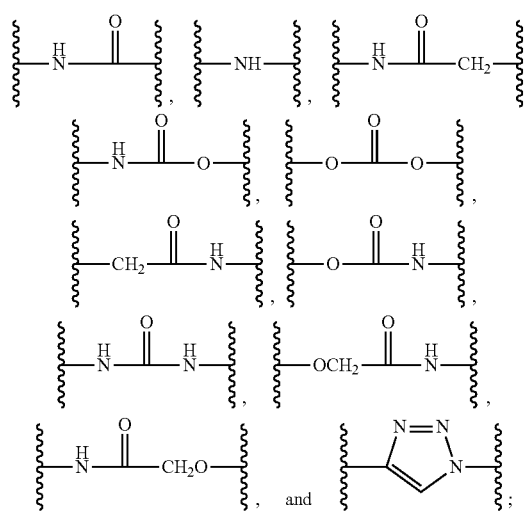

and
$R_3$ and $R_4$ are independently

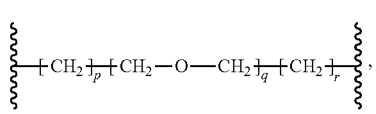

wherein p is 0-3, q is 0-12, and r is 1-3.

In some embodiments of aspects provided herein, the nucleoside 5'-triphosphate analog of formulae (I), (II) and (III) is further defined as:
w is 1;
X is O;
$R_X$ is H or methyl;
$L_1$ is

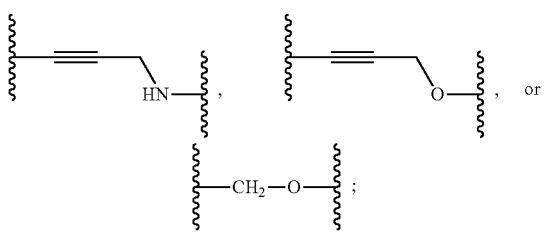

$L_2$ is

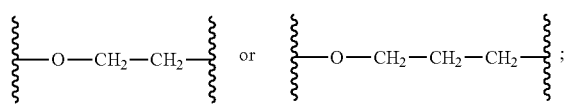

$L_3$ is

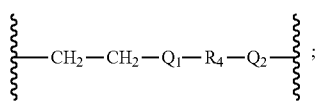

$R_4$ is

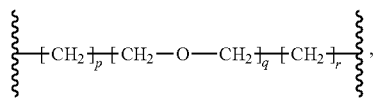

wherein p is 0-3, q is 0-12, and r is 1-3; and
$Q_1$ and $Q_2$ are independently selected from the group consisting of a bond,

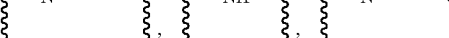

In some embodiments of aspects provided herein, D in formulae, (I), (II) and (III) is a fluorophore.

In some embodiments of aspects provided herein, the reducing reagent to cleave the compound of formulae (I), (II) and (III) is dithiothreitol (DTT), 2-mercaptoethanol, trialkylphosphine, triarylphosphine or tris(2-carboxyethyl) phosphine. In some embodiments of aspects provided herein, the reducing reagent to cleave the compound of formula (II) is trialkylphosphine, triarylphosphine, or tris(2-carboxyethyl)phosphine. In some embodiments of aspects provided herein, the reducing reagent to cleave the compound of formula (I) is dithiothreitol (DTT) or 2-mercaptoethanol.

A fourth aspect of the present disclosure provides a composition. The composition comprises a first, second, third and fourth nucleoside 5'triphosphate analog, wherein the analog is defined according to formula (II) or analogs thereof, and the base is different for each of the first, second, third and fourth nucleoside 5'-triphosphate analogs; and the detectable label is different for each different base.

A fifth aspect of the present disclosure provides a composition. The composition comprises four nucleoside 5'-triphosphates as reversible terminators, wherein each of reversible terminators is according to formula (III) described above. Each of the four nucleoside 5'-triphosphates has a different base, wherein each different base has a different detectable label. Because each different reversible terminator may comprise a different detectable label, detection and differentiation of each different type of reversible terminators may be achieved. In addition, after the disulfide bonds are cleaved by the reducing reagent, there is no free thiol group linked to the different base or to the 3'-O.

In some embodiments of aspects provided herein for the composition, the detectable label $D_1$ is a fluorophore. In some embodiments of aspects provided herein for the composition, the reducing reagent to cleave the compound of formulae (I), (II) and (III) is dithiothreitol (DTT), 2-mercaptoethanol, trialkylphosphine, triarylphosphine or tris(2-carboxyethyl)phosphine. In some embodiments of aspects provided herein for the composition, the reducing reagent to cleave the compound of formula (II) is trialkylphosphine, triarylphosphine, or tris(2-carboxyethyl)phosphine. In some embodiments of aspects provided herein for the composition, the reducing reagent to cleave the compound of formula (III) is DTT or 2-mercaptoethanol.

A sixth aspect of the present disclosure provides that the nucleoside 5'-triphosphate analog is formula (IV):

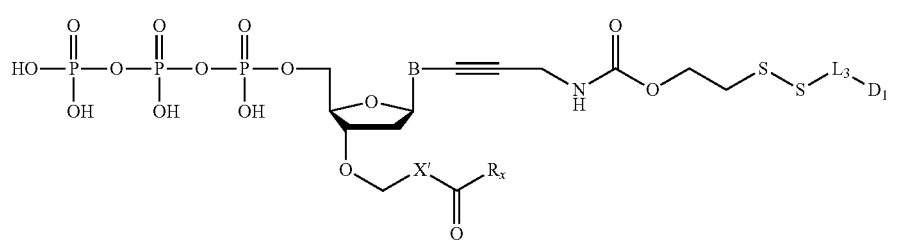

(IV)

or a salt and/or protonated form thereof, wherein:

X' is O or S $R_X$ is H or $C_{1-6}$ alkyl, wherein the $C_{1-6}$ alkyl is unsubstituted or substituted by 1-3 groups selected from the group consisting of F and Cl;

base B is selected from the group consisting of

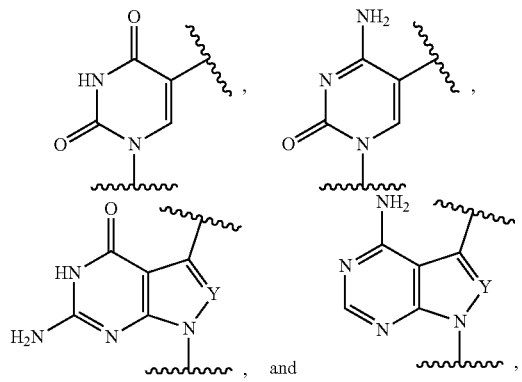

and Y is CH or N;

$L_1$ is a first linker group and $L_1$ is 3-25 atoms in length;

$L_2$ is a second linker group and $L_2$ is

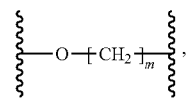

and m is 2 or 3;

$L_3$ is a third linker group and $L_3$ is 4-47 atoms in length;

$D_1$ is a detectable label; and the disulfide bonds are cleavable by a reducing reagent, thereby after the disulfide bonds are cleaved by the reducing reagent, there is no free thiol group linked to the base B or the 3'-O.

In some embodiments of aspects provided herein, the nucleoside 5'-triphosphate analog of formula (IV) is further defined as: $L_1$ comprises alkylene, alkenylene, alkynylene, —O—, —NH—, or combinations thereof. In some embodiments of aspects provided herein, the nucleoside 5'-triphosphate analog of formula (IV) is further defined as: $L_3$ comprises alkylene, alkenylene, cycloalkylene with a 3-7 membered ring, alkynylene, arylene, heteroarylene, heterocyclene with a 5-12 membered ring comprising 1-3 atoms of N, O or S, —O—, —NH—, —S—, —N($C_{1-6}$ alkyl)-, —C(=O)—, —C(=O)NH—, or combinations thereof.

In some embodiments of aspects provided herein, the nucleoside 5'-triphosphate analog of formula (IV) is further defined as:

$L_1$ is

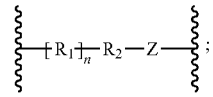

n is 0 or 1;

$R_1$ is

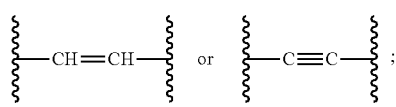

$R_2$ is

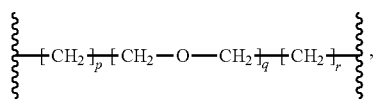

wherein p is 0-3, q is 0-12, and r is 1-3; and

Z is O or NH.

In some embodiments of aspects provided herein, the nucleoside 5'-triphosphate analog of formulae (I), (II) and (III) is further defined as:

$L_3$ is

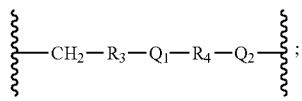

$Q_1$ and $Q_2$ are independently selected from the group consisting of a bond,

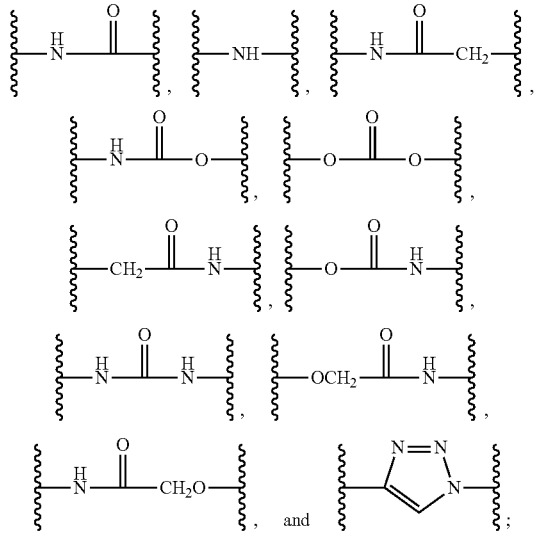

and $R_3$ and $R_4$ are independently

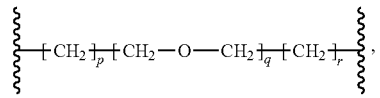

wherein p is 0-3, q is 0-12, and r is 1-3.

In some embodiments of aspects provided herein, the nucleoside 5'-triphosphate analog of formulae (I), (II) and (III) is further defined as:

w is 1;
X is O;
$R_X$ is H or methyl;
$L_1$ is

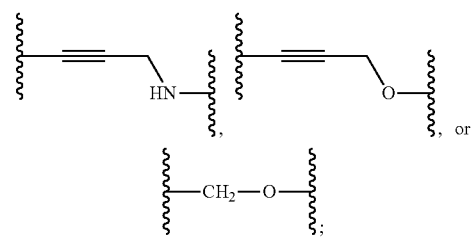

$L_2$ is

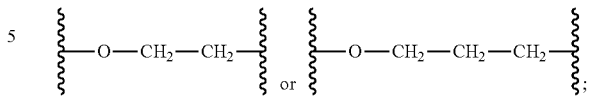

$L_3$ is

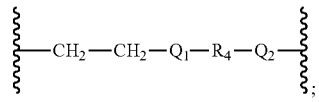

$R_4$ is

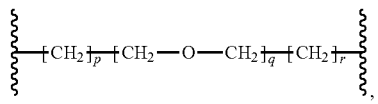

wherein p is 0-3, q is 0-12, and r is 1-3; and $Q_1$ and $Q_2$ are independently selected from the group consisting of a bond,

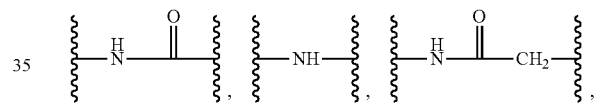

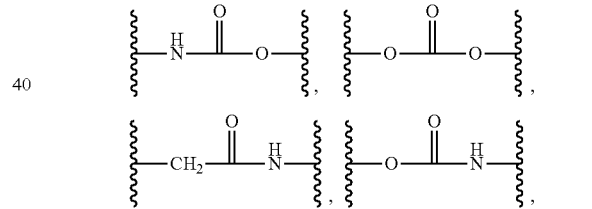

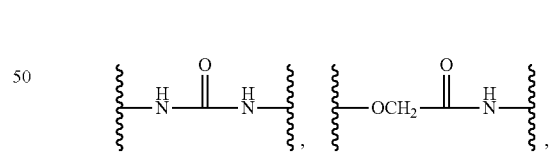

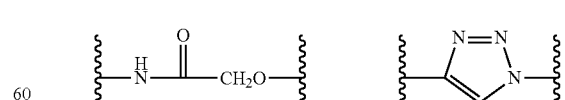

In some embodiments of aspects provided herein, D in formula (IV) is a fluorophore.

A seventh aspect of the present disclosure provides that the nucleoside 5'-triphosphate analog is formula (V):

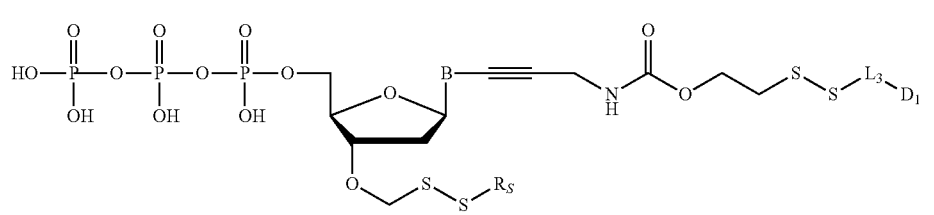

(V)

or a salt and/or protonated form thereof, wherein:

$R_S$ is $C_{1-6}$ alkyl, wherein the $C_{1-6}$ alkyl is unsubstituted or substituted by 1-3 groups selected from the group consisting of F and Cl;

base B is selected from the group consisting of

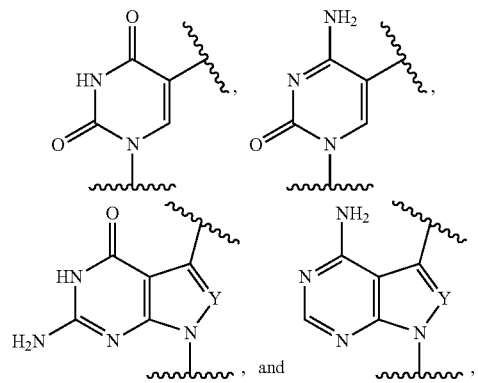

and Y is CH or N;

$L_1$ is a first linker group and $L_1$ is 3-25 atoms in length;

$L_2$ is a second linker group and $L_2$ is

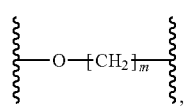

and m is 2 or 3;

$L_3$ is a third linker group and $L_3$ is 4-47 atoms in length;

$D_1$ is a detectable label; and the disulfide bonds are cleavable by a reducing reagent, thereby after the disulfide bonds are cleaved by the reducing reagent, there is no free thiol group linked to the base B or the 3'-O.

In some embodiments of aspects provided herein, the nucleoside 5'-triphosphate analog of formula (V) is further defined as: $L_3$ comprises alkylene, alkenylene, cycloalkylene with a 3-7 membered ring, alkynylene, arylene, heteroarylene, heterocyclene with a 5-12 membered ring comprising 1-3 atoms of N, O or S, —O—, —NH—, —S—, —N($C_{1-6}$ alkyl)-, —C(=O)—, —C(=O)NH—, or combinations thereof.

In some embodiments of aspects provided herein, the nucleoside 5'-triphosphate analog of formula (V) is further defined as: $R_S$ is methyl or ethyl.

In some embodiments of aspects provided herein, the nucleoside 5'-triphosphate analog of formula (V) is further defined as:

$L_3$ is

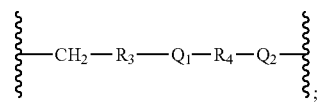

$Q_1$ and $Q_2$ are independently selected from the group consisting of a bond,

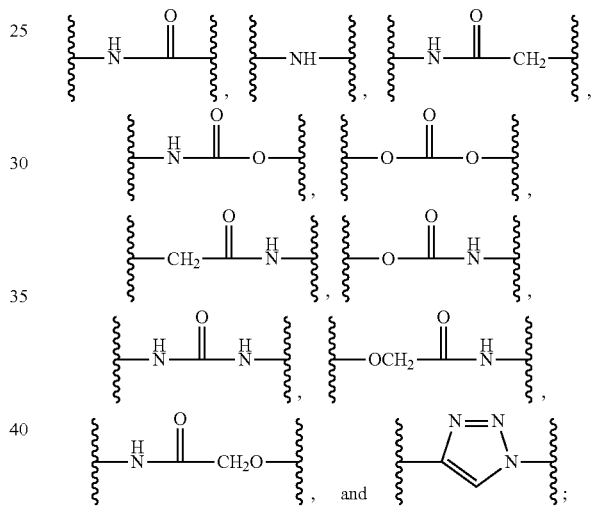

and $R_3$ and $R_4$ are independently

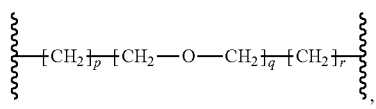

wherein p is 0-3, q is 0-12, and r is 1-3.

An eighth aspect of the present disclosure provides a method for sequencing a polynucleotide, comprises: performing a polymerization reaction in a reaction system comprising a target polynucleotide to be sequenced, one or more polynucleotide primers which hybridize with the target polynucleotide to be sequenced, a catalytic amount of a polymerase enzyme, and one or more nucleoside 5'-triphosphate analogs of formulae (I), (II), (III), (IV) or (V) as described herein, thereby generating one or more sequencing products complimentary to the target polynucleotide.

In some embodiments of aspects provided herein for the sequencing method, the one or more nucleoside 5'-triphosphate analogs is of formula (II). In some embodiments of aspects provided herein for the sequencing method, the one or more nucleoside 5'-triphosphate analogs is of formula (III). In some embodiments of aspects provided herein for the sequencing method, the one or more nucleoside 5'-triphosphate analogs is of formula (IV). In some embodiments of aspects provided herein for the sequencing method, the one or more nucleoside 5'-triphosphate analogs is of formula (V).

In some embodiments of aspects provided herein for the sequencing method, the one or more 5'-triphosphate analogs are at a concentration of no more than 400 µM. In some embodiments of aspects provided herein for the sequencing method, the one or more 5'-triphosphate analogs are at a concentration of no more than 100 µM. In some embodiments of aspects provided herein for the sequencing method, the one or more 5'-triphosphate analogs are at a concentration of no more than 50 µM. In some embodiments of aspects provided herein for the sequencing method, the one or more 5'-triphosphate analogs are at a concentration of no more than 10 µM. In some embodiments of aspects provided herein for the sequencing method, the one or more 5'-triphosphate analogs are at a concentration of no more than 5 µM. In some embodiments of aspects provided herein for the sequencing method, the one or more 5'-triphosphate analogs are at a concentration of no more than 3 µM. In some embodiments of aspects provided herein for the sequencing method, the one or more 5'-triphosphate analogs are at a concentration of no more than 2 µM. In some embodiments of aspects provided herein for the sequencing method, the method further comprises treating the one or more sequencing products with a reducing reagent of dithiothreitol (DTT), 2-mercaptoethanol, trialkylphosphine, triarylphosphine or tris(2-carboxyethyl)phosphine. In some embodiments of aspects provided herein for the sequencing method, the reducing agent is trialkylphosphine, triarylphosphine, or tris(2-carboxyethyl)phosphine. In some embodiments, the reducing agent is dithiothreitol (DTT) or 2-mercaptoethanol. In some embodiments of aspects provided herein for the sequencing method, after treating with the reducing reagent, the one or more sequencing products do not have free thiol group linked to any of their bases. In some embodiments of aspects provided herein for the sequencing method, when using one or more nucleoside 5'-triphosphate analogs of formulae (III) or (V) as described herein, after treating with the reducing reagent, the one or more sequencing products do not have free thiol group linked to any of their bases or to any of their 3'-O.

In some embodiments of aspects provided herein for the sequencing method when using one or more nucleoside 5'-triphosphate analogs of formulae (II) or (IV) as described herein, the method further comprises after the treating with the reducing reagent, treating the one or more sequencing products with a basic reagent. In some embodiments of aspects provided herein for the sequencing method, treating with the basic reagent provides 3'-OH. In some embodiments of aspects provided herein for the sequencing method, the basic reagent is a buffer having a pH from about 10 to about 11. In some embodiments of aspects provided herein for the sequencing method, the basic reagent is a sodium carbonate/sodium bicarbonate buffer.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
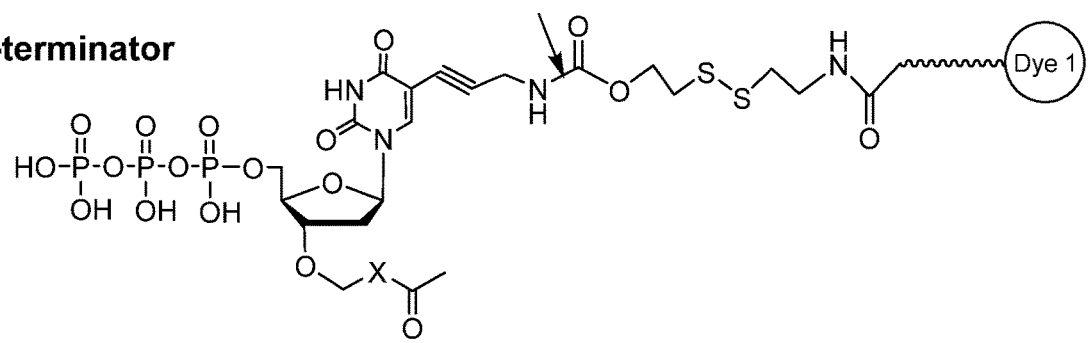
FIG. 1 illustrates nucleotide terminators of the present disclosure with deoxyribose as the sugar and thymine/uracil, adenine, cytidine and guanine as the base. These reversible terminators can be prepared using similar chemistry as provided herein to afford labeled nucleotide reversible terminators.
Figure 1:
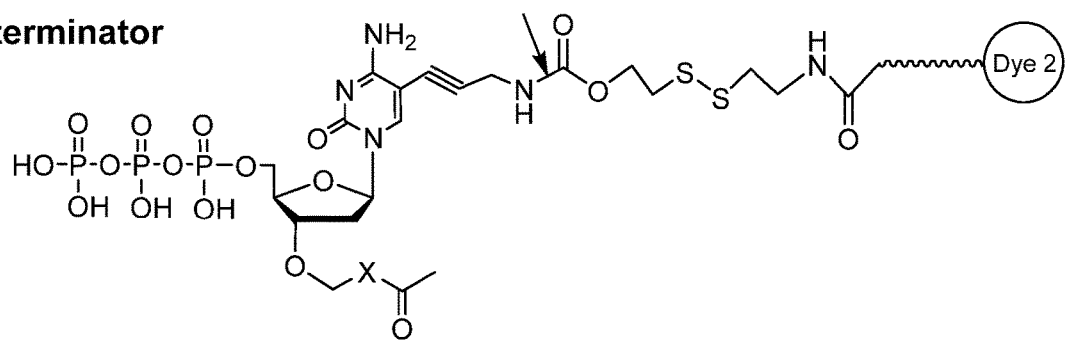
Figure 1:
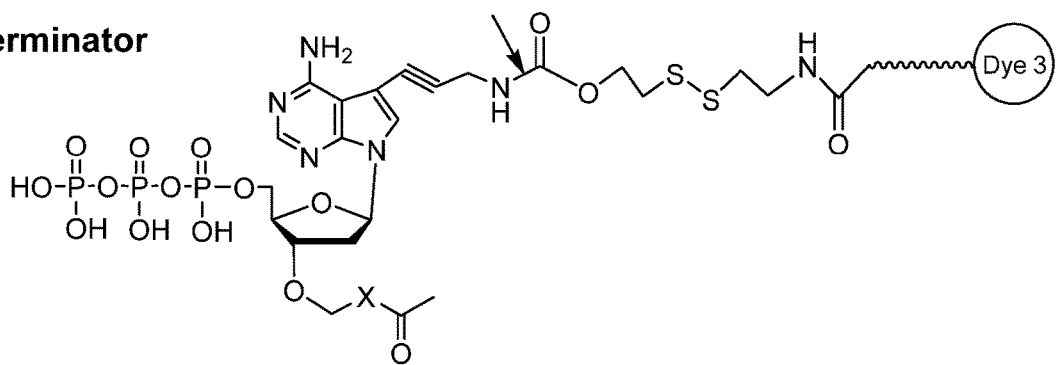
Figure 1:
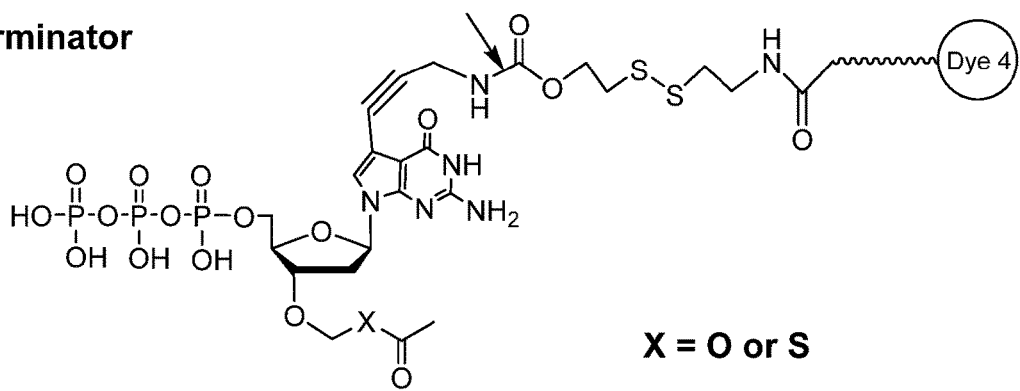

The second generation sequencing (NGS) approaches, involving sequencing by synthesis (SBS) have experienced a rapid development as data produced by these new technologies mushroomed exponentially. The SBS approach may have shown promise as a new sequencing platform. Despite remarkable progress in last two decades, there remains much room for the development before introducing them into practice.

One step of the SBS methodologies may be to place a removable cap at the 3'-OH position of the last nucleotide already in the growing strand. Accordingly, the synthesis of labeled nucleotides with removable caps at its 3'-OH position may be of interest to developing new SBS technologies.

Some SBS methods may use dye-labelled, modified nucleotides. These modified nucleotides may be incorporated specifically by an incorporating enzyme (e.g., a DNA polymerase), cleaved during or following fluorescence imaging, and extended as modified or natural bases in the growing strand in the ensuing cycles. Two main classes of reversible terminators have been reported: 3' blocked terminators, which contain a cleavable group attached to the 3'-hydroxyl group of the deoxyribose sugar; and 3'-unblocked terminators, which bears an unblocked 3'-hydroxyl group at the deoxyribose sugar. Several 3'-blocking groups may include 3'O-allyl and 3'O-azidomethyl. For example, some reversible terminators may have either 3' blocking groups, 3'O-allyl (Intelligent bio) or 3'-O-azidomethyldNTP's (Illumina/Selexa) while the label is linked to the base, which act as a reporter and can be cleaved. Other reversible terminators may be 3'-unblocked reversible terminators in which the terminator group is linked to the base as well as a fluorescence group, with the fluorescence group not only acting as a reporter but also behaving as reversible terminating group.

One issue with many cyclic reversible terminator (CRT) technologies in the NGS platform may be short read length, for example, a read length between about 100 and about 150 bases. One of the reasons causing this limitation of short read length may lie in the findings that many modified nucleotides developed so far for CRT may leave behind a vestige (or scar) after cleavage of the linker carrying the fluorophore. This vestige or scar comprises some residual linker structures or other chemical entities that are attached to the base molecules and are accumulated over time in subsequent sequencing cycles, Accumulation of such scars along the major grooves of the DNA duplex after two rounds of sequencing extension may impede further polymerase-catalyzed extensions, such as, for example, impairing the stability of DNA double helix structure adversely and hindering the substrate recognition and primer extension steps.

Therefore, there is a need for the development of a suitable chemical moiety or capping group to cap the 3'-OH of the nucleotide such that the chemical moiety or capping group may temporarily terminate the polymerase reaction to allow the identification of the incorporated nucleotide. This development may help further development of the SBS methods. In addition, the chemical moiety or capping group can be removed from the synthesized DNA extension products to regenerate the 3'-hydroxy group on the newly incorporated nucleotide for the continuous polymerase reaction.

Therefore, there is a need to develop nucleotide analogs that work well with polymerase enzymes and are able to terminate strand growth upon incorporation into the growing strand. A pause in polymerase activity during strand elongation caused by a reversible terminator nucleotide analog allows accurate determination of the identity of the incorporated nucleic acid. Ability to continue strand synthesis after this accurate determination is made would be ideal, through subsequent modification of the reversible terminator nucleotide analog that allows the polymerase enzyme to continue to the next position on the growing DNA strand. The process of arresting DNA polymerization followed by removal of the blocking group on the incorporated non-native nucleotide is referred to herein as sequential reversible termination. Another requirement of sequential reversible termination is that the capping group on the 3'-OH of the non-native nucleotide analog must be easily removed without damaging the growing DNA strand or the polymerase, i.e. termination must be reversible under mild reaction conditions. Still another goal of the present disclosure is to find a reducing reagent to cleave both the detectable label attached on the incorporated nucleotide and the blocking group on the incorporated non-native nucleotide.

Sequencing-by-Synthesis (SBS) and Single-Base-Extension (SBE) Sequencing

Several techniques are available to achieve high-throughput sequencing. (See, Ansorge; Metzker; and Pareek et al., "Sequencing technologies and genome sequencing," *J. Appl. Genet.*, 52(4):413-435, 2011, and references cited therein). The SBS method is a commonly employed approach, coupled with improvements in PCR, such as emulsion PCR (emPCR), to rapidly and efficiently determine the sequence of many fragments of a nucleotide sequence in a short amount of time. In SBS, nucleotides are incorporated by a polymerase enzyme and because the nucleotides are differently labeled, the signal of the incorporated nucleotide, and therefore the identity of the nucleotide being incorporated into the growing synthetic polynucleotide strand, are determined by sensitive instruments, such as cameras.

SBS methods commonly employ reversible terminator nucleic acids, i.e. bases which contain a covalent modification precluding further synthesis steps by the polymerase enzyme once incorporated into the growing stand. This covalent modification can then be removed later, for instance using chemicals or specific enzymes, to allow the next complementary nucleotide to be added by the polymerase. Other methods employ sequencing-by-ligation techniques, such as the Applied Biosystems SOLiD platform technology. Other companies, such as Helicos, provide technologies that are able to detect single molecule synthesis in SBS procedures without prior sample amplification, through use of very sensitive detection technologies and special labels that emit sufficient light for detection. Pyrosequencing is another technology employed by some commercially available NGS instruments. The Roche Applied Science 454 GenomeSequencer, involves detection of pyrophosphate (pyrosequencing). (See, Nyren et al., "Enzymatic method for continuous monitoring of inorganic pyrophosphate synthesis," *Anal. Biochem.*, 151:504-509, 1985; see also, US Patent Application Publication Nos. 2005/0130173 and 2006/0134633; U.S. Pat. Nos. 4,971,903, 6,258,568 and 6,210,891).

Sequencing using the presently disclosed reversible terminator molecules may be performed by any means available. Generally, the categories of available technologies include, but are not limited to, sequencing-by-synthesis (SBS), sequencing by single-base-extension (SBE), sequencing-by-ligation, single molecule sequencing, and pyrosequencing, etc. The method most applicable to the present compounds, compositions, methods and kits is SBS. Many commercially available instruments employ SBS for determining the sequence of a target polynucleotide. Some of these are briefly summarized below.

One method, used by the Roche Applied Science 454 GenomeSequencer, involves detection of pyrophosphate (pyrosequencing). (See, Nyren et al., "Enzymatic method for continuous monitoring of inorganic pyrophosphate synthesis," *Anal. Biochem.*, 151:504-509, 1985). As with most methods, the process begins by generating nucleotide fragments of a manageable length that work in the system employed, i.e. about 400-500 bp. (See, Metzker, Michael A., "Sequencing technologies—the next generation," *Nature Rev. Gen.*, 11:31-46, 2010). Nucleotide primers are ligated to either end of the fragments and the sequences individually amplified by binding to a bead followed by emulsion PCR. The amplified DNA is then denatured and each bead is then placed at the top end of an etched fiber in an optical fiber chip made of glass fiber bundles. The fiber bundles have at the opposite end a sensitive charged-couple device (CCD) camera to detect light emitted from the other end of the fiber holding the bead. Each unique bead is located at the end of a fiber, where the fiber itself is anchored to a spatially-addressable chip, with each chip containing hundreds of thousands of such fibers with beads attached. Next, using an SBS technique, the beads are provided a primer complementary to the primer ligated to the opposite end of the DNA, polymerase enzyme and only one native nucleotide, i.e., C, or T, or A, or G, and the reaction allowed to proceed. Incorporation of the next base by the polymerase releases light which is detected by the CCD camera at the opposite end of the bead. (See, Ansorge, Wilhelm J., "Next-generation DNA sequencing techniques," *New Biotech.*, 25(4): 195-203, 2009). The light is generated by use of an ATP sulfurylase enzyme, inclusion of adenosine 5' phosphosulferate, luciferase enzyme and pyrophosphate. (See, Ronaghi, M., "Pyrosequencing sheds light on DNA sequencing," *Genome Res.*, 11(1):3-11, 2001).

A commercially available instrument, called the Genome Analyzer, also utilizes SBS technology. (See, Ansorge, at page 197). Similar to the Roche instrument, sample DNA is first fragmented to a manageable length and amplified. The amplification step is somewhat unique because it involves formation of about 1,000 copies of single-stranded DNA fragments, called polonies. Briefly, adapters are ligated to both ends of the DNA fragments, and the fragments are then hybridized to a surface having covalently attached thereto primers complimentary to the adapters, forming tiny bridges on the surface. Thus, amplification of these hybridized fragments yields small colonies or clusters of amplified fragments spatially co-localized to one area of the surface. SBS is initiated by supplying the surface with polymerase enzyme and reversible terminator nucleotides, each of which is fluorescently labeled with a different dye. Upon incorporation into the new growing strand by the polymerase, the fluorescent signal is detected using a CCD camera. The terminator moiety, covalently attached to the 3' end of the reversible terminator nucleotides, is then removed as well as the fluorescent dye, providing the polymerase enzyme with a clean slate for the next round of synthesis. (Id., see also, U.S. Pat. No. 8,399,188; Metzker, at pages 34-36).

Many SBS strategies rely on detection of incorporation of detectably labeled nucleotides and nucleotide analogs. Such detection may rely on fluorescence or other optical signal, but this is not a requirement. Other technologies available are targeted towards measuring changes in heat and pH surrounding the nucleotide incorporation event. (See, U.S. Pat. Nos. 7,932,034 and 8,262,900; U.S. Patent Application Publication No. 20090127589; and Esfandyarpour el al., "Structural optimization for heat detection of DNA thermosequencing platform using finite element analysis," *Biomicrofluidics*, 2(2):024102 (1-11), 2008). Ion Torrent, a Life Technologies company, utilizes this technology in their ion sensing-based SBS instruments. In the Ion Torrent instrument, field effect transistors (FETs) are employed to detect minute changes in pH in microwells where the SBS polymerase reaction is occurring. Each well in the microwell array is an individual single molecule reaction vessel containing a polymerase enzyme, a target/template strand and the growing complementary strand. Sequential cycling of the four nucleotides into the wells allows FETs aligned below each microwell to detect the change in pH as the nucleotides are incorporated into the growing DNA strand. FETs convert this signal into a change in voltage, the change being commensurate in magnitude with the total number of nucleotides incorporated in that synthesis step.

In SBS-based NGS methods, reversible terminator nucleotides are may be needed to obtain the identity of the polynucleotide target sequence in an efficient and accurate manner. The present reversible terminators may be utilized in any of these contexts by substitution for the nucleotides and nucleotide analogs previously described in those methods. That is, the substitution of the present reversible terminators may enhance and improve all of these SBS and SBE methods. The majority of these protocols utilize deoxyribonucleotide triphosphates, or dNTPs. Likewise, the present reversible terminators may be substituted in dNTP form. Other forms of the present reversible terminators useful in other methodologies for sequencing are described below.

Reversible Terminator Nucleotides

The process for using reversible terminator molecules in the context of SBS, SBE and like methodologies generally involves incorporation of a labeled nucleotide analog into the growing polynucleotide chain, followed by detection of the label, then cleavage of the nucleotide analog to remove the covalent modification blocking continued synthesis. The cleaving step may be accomplished using enzymes or by chemical cleavage. Modifications of nucleotides may be made on the 5' terminal phosphate or the 3' hydroxyl group. Developing a truly reversible set of nucleotide terminators has been a goal for many years. Despite the recent advances only a few solutions have been presented, most of which cause other problems, including inefficient or incomplete incorporation by the polymerase, inefficient or incomplete cleavage of the removable group, or harsh conditions needed to for the cleaving step causing spurious problems with the remainder of the assay and/or fidelity of the target sequence. In a standard SBS protocol using reversible terminators, the polymerase enzyme has to accommodate obtrusive groups on the nucleotides that are used for attachment of fluorescent signaling moiety, as well as blocking groups on the 3'-OH. Native polymerases have a low tolerance for these modifications, especially the 3'-blocking groups. Mutagenesis of polymerase enzymes is necessary to obtain enzymes with acceptable incorporation efficiencies. After cleaving the fluorophore from the base, many current methodologies leave an unnatural "scar" on the remaining nucleobase. (See, for instance, Metzker, Michael A., "Sequencing technologies—the next generation," *Nature Rev. Gen.*, 11:31-46, 2010 and Fuller et al., "The challenges of sequencing by synthesis," *Nat. Biotech.*, 27(11): 1013-1023, 2009).

Thus, a limited number of groups suitable for blocking the 3'-oxygen have been shown to be useful when used in combination with certain mutant polymerases which allow the enzyme to tolerate modifications at the 3'-position. These include azidomethyl, allyl and allyloxycarbonyl. (See, for example, Metzker et al., "Termination of DNA synthesis by novel 3'-modified deoxyribonucleoside triphosphates," *Nucleic Acids Res.*, 22:4259-4267, 1994; and U.S. Pat. Nos. 5,872,244; 6,232,465; 6,214,987; 5,808,045; 5,763,594, and 5,302,509; and U.S. Patent Application Publication No. 20030215862). These groups require the application of chemical reagents to conduct cleavage. Carboxylic esters, carbonates or thiocarbonate groups at the 3'-position have proven too labile to be effective as chain terminators, ostensibly due to an intrinsic editing activity of the polymerase distinct from exonuclease activity. (See, Canard B & Sarfati R., "DNA polymerase fluorescent substrates with reversible 3'-tags," *Gene*, 148:1-6, 1994).

Disclosed herein is a new class of fluorescently labeled reversible terminators. The new class of fluorescently labeled reversible terminators has a 3'-acyloxymethyl or 3-acylthiomethyl blocking group on the 3'-0 of the ribose ring of the nucleotides. The 3'-acyloxymethyl or 3'-acylthiomethyl group-modified nucleotides can be recognized as substrates by DNA polymerase for extension reactions to add to the growing strand during polymerase reactions, and, after being incorporated in the growing strand, can be cleaved under mild conditions. In addition, the fluorophore tags can be linked to the base through a disulfide linkage in connection with a carbamate linker moiety bridging the base and the disulfide group. The fluorophore tags can be cleaved under mild conditions to break the disulfide bond. For example, exposing the new reversible terminators with reducing agents, such as, for example, trialkylphosphine, (tris(2-carboxyethyl)phosphine) (TCEP), dithiothreitol (DTT) or 2-mercaptoethanol, may not only break the disulfide bonds of the fluorophore linker, but may trigger a simultaneous cleavage of the carbamate bond by an intramolecular cyclisation in the presence of the of the nascent sulfide anion generated from the disulfide breakage (Scheme 1), thereby removing the sulfide anions from the nucleotide (and the growing chain of the DNA) in the process. Then a basic reagent may be used to cleave the 3'-acyloxymethyl or 3'-acylthiomethyl blocking group on the ribose and reveal the free 3'-OH for further elongation of the growing chain.

propylenediyl group. Although Scheme 1 shows a triphosphate in the reversible terminator, similar cleavage mechanisms may occur in other type of molecules as long as the same acyloxymethyl or acylthiomethyl group is at the 3' position and the label D1 is linked to the nucleotide base B in the same or similar ways (i.e., via a disulfide bond which is separate from a carbamate group by an 1,2-ethylenediyl or 1,3-propylenediyl group). Similar mechanism may also occur when the reversible terminators are incorporated into the growing chain (i.e., the triphosphate group in Compound A may change into a phosphodiester group.

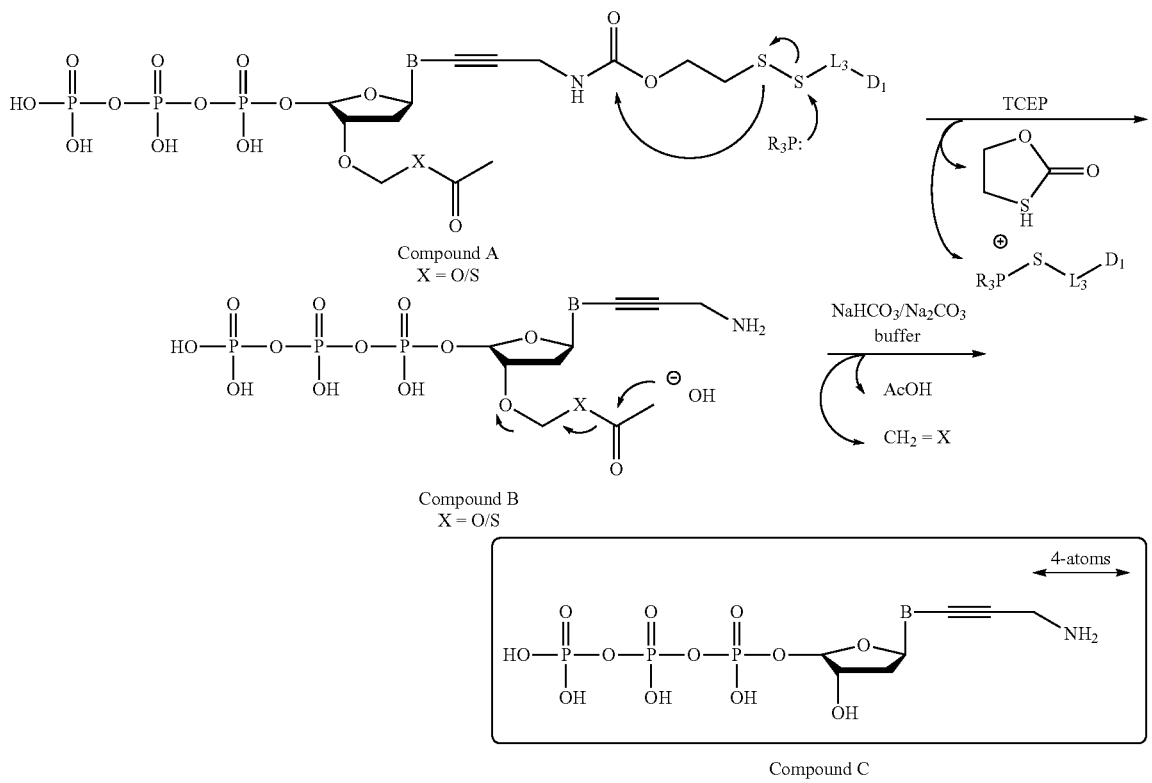

Scheme 1

As shown in Scheme 1, Compound A comprises a label $D_1$ linked by a linker $L_3$ to a disulfide bond. The disulfide bond is linked to the nucleotide base B via an amide bond. Compound A also comprises an acyloxymethyl or acylthiomethyl group on its 3' hydroxyl group. Label $D_1$ may a fluorescent label or fluorophore tag. Linker $L_3$ can be an alkyl group, an alkoxyl group, a carbamate group, an amide group, an ester group, or any combination of at least two of these groups. When Compound A is treated with trialkylphosphine, TCEP, DTT or 2-mercaptoethanol, the disulfide bond can be cleaved and the newly generated thiol group linked to the nucleotide base can undergo spontaneous cyclization to afford Compound B as shown. Compound B, when treated with a basic reagent, can eliminate the 3' blocking group to generate Compound C, which may not comprise any terminal thiol groups.

Although in Compound A, the disulfide group as shown in Scheme 1 is separated from the carbamate group by two atoms, such as a 1,2-ethylenediyl group, similar spontaneous cleavage can occur when the disulfide group is separated from the carbamate group by three atoms, such as a 1,3-

These novel reversible terminators, after incorporation into the growing chain and cleavage reaction, may comprise, a small (e.g., 4-atom) scar left on the nucleotide base. The 4-atom scar may be smaller when compared to with Illumina's 10-atom scar left on the nucleotide bases after the cleavage of the fluorophores. The novel reversible terminators may provide many advantages when compared with other reversible terminators having terminal thiol left on the incorporated nucleotide. For example, residual thiols may be undesirable for sequencing reactions because the residual thiols may be reactive in many ways. For instance, the reactive terminal free thiol functional groups may be associated with premature disulfide cleavages on the incoming nucleotide bases when the growing chain is further extended with additional fluorophore-labeled, disulfide-containing nucleotides. Additionally, if the terminal free thiol functional groups react with the incoming nucleotides (comprising reactive groups toward free thiol groups; e.g., a disulfide bond attached to the incoming nucleotide base), new covalent crosslinks may be formed (e.g., forming a disulfide bond with the incoming nucleotide bases or the dyes) such that the incoming nucleotide (or the dye) may be subsequently added to the growing strand as the sequencing process proceeds. This may cleave those disulfide linkers prematurely, releasing the dyes before they can be imaged or erroneously connect with the dye even if the nucleotide base is not complementary to the base on the template. Further, the free thiol groups can form covalent crosslinks with amino acids of proteins (e.g., polymerase) that contain free thiol groups or disulfide bonds. These side-reactions may "gum-up" or interfere with the sequencing process by impeding the polymerase' ability to advance along or dissociate from the elongation complex. In addition, the free thiol groups can form covalent crosslinks with other residual thiols attached to nucleotide bases on the same growing strand or adjacent growing strands being sequenced.

Using the novel reversible terminators as disclosed herein, the DNA sequences may be determined. DNA sequences of the template may be determined by the unique fluorescence emission of the fluorophore tag attached to the nucleotide base. After the ensuing cleavage of the disulfide bond connected with the fluorophore, the cleavage of acyl or thioacyl group connected to the 3' position may trigger spontaneous cleavage of a formaldehyde or methanethione group to regenerate the free 3'-hydroxy group (Scheme 1) for further elongation. The continuing elongation of the growing chain may delineate additional sequencing information of the template.

For example, as shown in Scheme 1, a disulfanylalkoxycarbonylamino linked fluorophore tags may be added to the bases of the nucleotides. Exposing the terminators with reducing agent, such as TCEP, dithiothreitol (DTT) or 2-mercaptoethanol, may reduce and break the disulfide bond, triggering the simultaneous cleavage of the carbamate bond by an intra-molecular cyclization of the resulting sulfide anion. Treatment with a basic reagent may cleave the 3' capping or blocking group. The cleavage of the fluorophore may leave only a small (e.g., 4-atoms) scar on the base (Scheme 1).

It should be noted that although Scheme 1 illustrates a proposed mechanism through which the reversible terminator of the present disclosure can react with a reducing agent, such as, trialkylphosphine, TCEP, DTT or 2-mercaptoethanol, a similar mechanism may occur when the reversible terminator is incorporated into a DNA or RNA growing strand. In that case, the triphosphate moiety of the reversible terminator shown in Scheme 1 may be replaced with a phosphodiester bond linkage to the end of a DNA or RNA growing strand. Accordingly, before the treatment with the reducing agent, because the 3'-OH group of the reversible terminator is capped by the blocking/capping group, the DNA or RNA strand growth may terminate or stop. However, when treated with a reducing agent, such as, trialkylphosphine, TCEP, DTT or 2-mercaptoethanol, the fluorophore attached to the base can be cleaved, and the capping moiety on the 3'-OH group of the sugar can be cleaved when treated with a basic reagent, similarly to what has been illustrated above in Scheme 1. The exposed 3'-OH group of the incorporated reversible terminator on the end of the DNA or RNA growing strand may allow continued strand growth of the DNA and RNA.

Further, although the reversible terminator shown in Scheme 1 is a triphosphate, other analogs of triphosphate are allowed at the 5' position of the nucleotide, as shown elsewhere in this disclosure.

Design and Synthesis of 3'O-Modified Nucleoside Reversible Terminator with Cleavable Disulfide-Linked Fluorescent Tags:

The novel reversible terminators as disclosed may comprise an acyloxy or thioacyloxy blocking group on the 3'-OH group of the ribose or deoxyribose, and a fluorophore is tagged to the C-5 position of pyrimidines (C and U) or the C-7 position of purine bases (A and G) through a disulfide linkage as shown in FIG. 1. The arrows indicate the positions at which the linked fluorescent tags can be cleaved from the base.

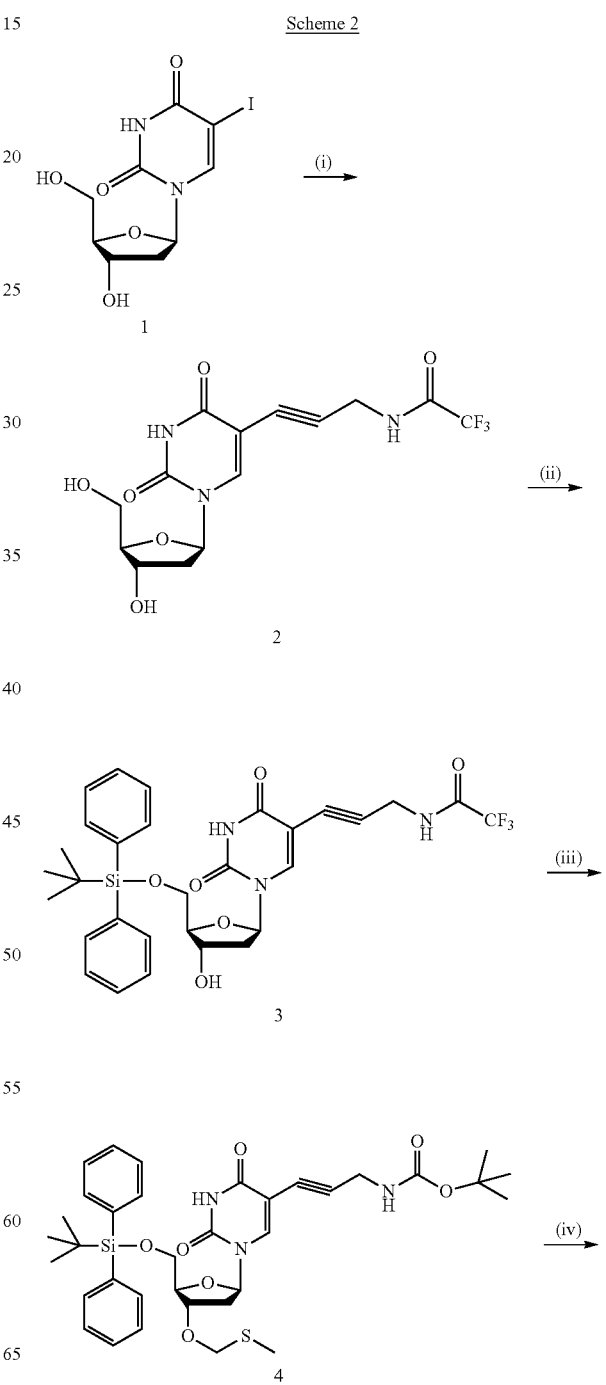

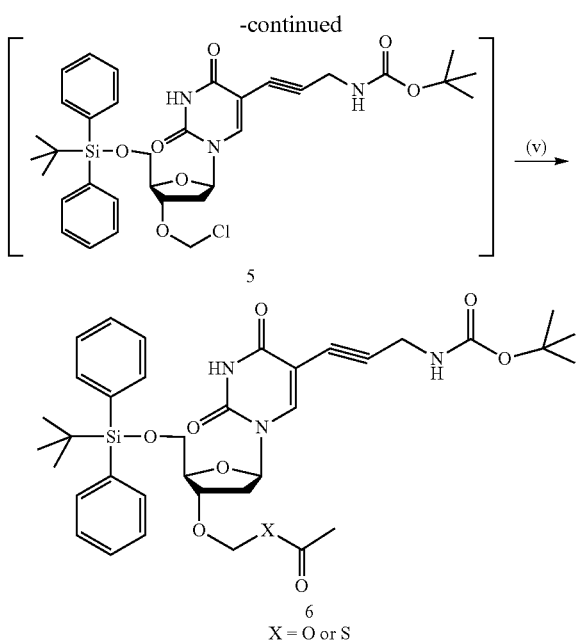

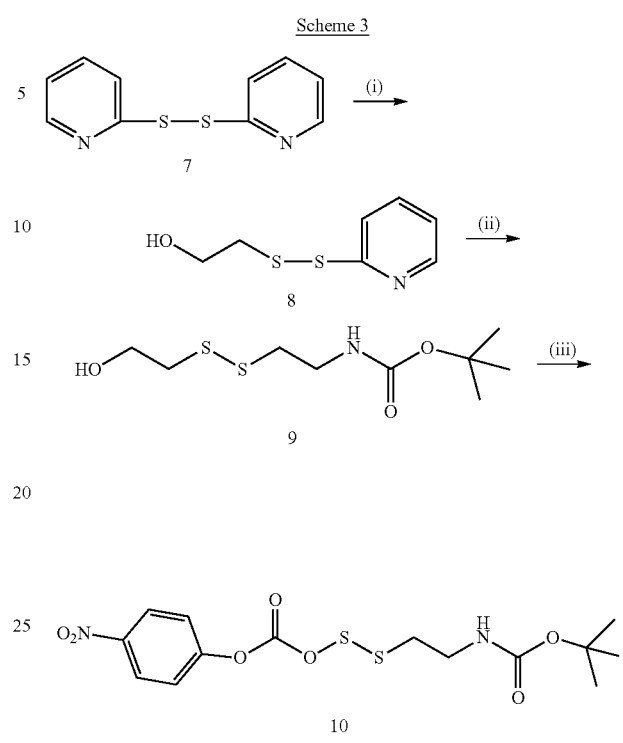

Reagents and conditions: (i) A-trifluoroacetylpropargylamine, Pd (PPh$_3$)$_4$, CuI, triethylamine, DMF, room temperature (RT), 12 h; (ii) tert-butyldiphenylsilylchloride, pyridine, RT, 6 h; (iii) (a) NH$_4$OH, MeOH, 55° C. 3 h; (b) di-tert-butyl dicarbonate (BOC$_2$O), triethylamine, CH$_2$Cl$_2$, RT; (c) DMSO, AcOH, acetic anhydride, RT, 12 h; (iv) SO$_2$Cl$_2$, 0° C., 1 h, (v) potassium salt of acetate or potassium salt of thioacetate, 18-crown-6, DMF, 4 h.

The synthesis of modified uridine reversible terminator can be carried out as shown in Scheme 2, which depicts a reaction scheme leading to the synthesis of (((2R,3S,5R)-5-(5-(3-aminoprop-1-yn-1-yl)-2,4-dioxo-3,4-dihydropyrimidin-1 (2H)-yl)-2-(((tert-butyldiphenylsilyl)oxy)methyl)tetrahydrofuran-3-yl)oxy)methyl acetate or thioacetate, which may be intermediates leading to modified uridine nucleotides. A palladium-catalyzed Sonogashira coupling of 5-iodo-2'deoxyuridine (1) with A-trifluoroacetylpropargylamine provided 2,2,2-trifluoro-N-(3-(1-((2R,4S,5R)-4-hydroxy-5-(hydroxymethyl)tetrahydrofuran-2-yl)-2,4-dioxo-1,2,3,4-tetrahydropyrimidin-5-yl)prop-2-yn-1-yl) acetamide (2). Silylation of 2,2,2-trifluoro-N-(3-(1-((2R,4S,5R)-4-hydroxy-5-(hydroxymethyl)tetrahydrofuran-2-yl)-2,4-dioxo-1,2,3,4-tetrahydropyrimidin-5-yl)prop-2-yn-1-yl) acetamide (2) afforded N-(3-(,5R)-4-hydroxy-5-(hydroxymethyl)tetrahydrofuran-2-yl)-2,4-dioxo-1,2,3,4-1-((2R,4S,5R)-5-(((tert-butyldiphenylsilyl)oxy)methyl)-4-hydroxytetrahydrofuran-2-yl)-2,4-dioxo-1,2,3,4-tetrahydropyrimidin-5-yl)prop-2-yn-1-yl)-2,2,2-trifluoroacetamide (3). The trifluoroacetamide protecting group is removed and the free primary amine is re-protected by a tert-butyloxycarbonyl (BOC) protecting group, following by conversion of the 3'-hydroxy group in 3 to 3'-O-methoxymethyl sulfide using DMSO, acetic acid and acetic anhydride by Pummerer's rearrangement to afford intermediate 4. Intermediate 4 is then converted to 3'-acyloxymethyl or 3'-acylthiomethyl derivative 6 in a one-pot reaction, first by in-situ conversion to 3'-O-chloromethyl intermediate 5 using sulfuryl chloride, followed by an ensuing reaction with the potassium salt of acetate or the potassium salt of thioacetate in the presence of 18-crown-6 to give the corresponding 3'-O-acyloxymethyl or 3'-O-acylthiomethyl ether 6, respectively.

Reagents and conditions: (i) 2-mercaptoethanol, pyridine, anhydrous MeOH, RT, 12 h; (ii) BOC-cysteamine, pyridine, MeOH, RT, 12 h; (iii) 4-nitrophenylchloroformate, Et$_3$N, MeCN.

The linker precursor 10 can be synthesized from activated disulfide 7 (Scheme 3). For example, condensation of commercially available 2,2'-dithiodipyridine 7 with 2-thioethanol may afford intermediate 8. Intermediate 8 may further react with N-tert-butoxycarbonyl-cysteamine to afford disulfide carbamate 9. The free terminal hydroxyl group of intermediate 9 can react with 4-nitrophenyl chlorocarbonate to afford 2-(N-tert-butoxyamido-ethyl)-2-yl-disulfanyl) ethyl-4-nitrophenyl carbonate 10, which can be an activated disulfide linker intermediate.

After these two intermediates 6 and 10 are synthesized, the novel reversible terminators may be synthesized, for example, according to steps shown in Scheme 4. Removal of the BOC group from 6 using trifluoroacetic acid, followed by condensation with activated linker 10 may afford 12. Removal of 5'-silyl group by treating 12 with tetrabutylammonium fluoride, followed by phosphorylation of the free 5'-OH on the ribose may afford the triphosphate 14. Finally, removal of the BOC group on 14 and condensation of resulting primary amine in 15 with N-hydroxysuccinimide (NHS) ester of a dye may afford a nucleoside reversible terminator 16. Because the 3' blocking group is an ester or thioester which may be removed by a basic solution, the pH range for the ensuing reactions after the installation of the 3' blocking group may be controlled. For example, the coupling reaction using an Alexa NHS ester to install the cleavable label may be carried out in sodium bicarbonate buffer (pH about 8.3) for 3 hrs at room temp. Under these conditions both, previously installed 3'O-acyloxymethyl and 3'O-thioacyloxymethyl blocking groups are stable.

Scheme 4
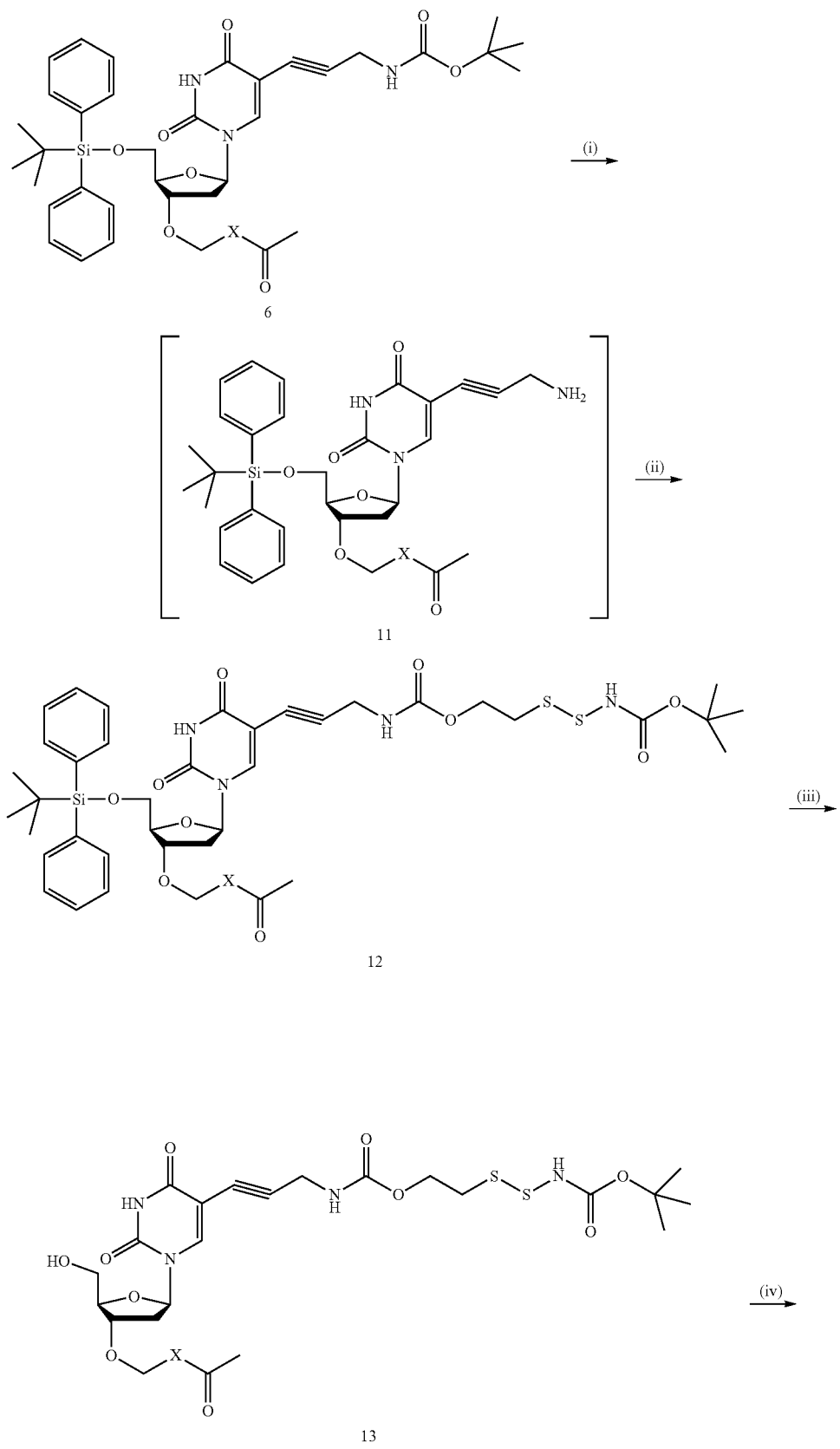

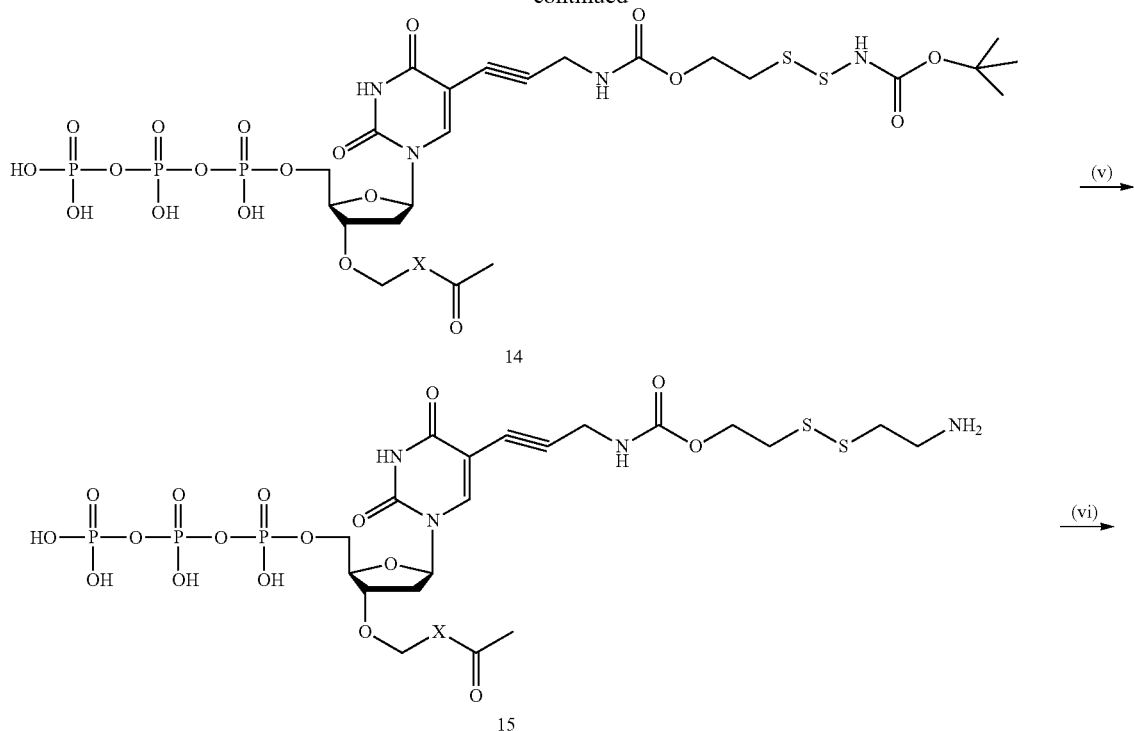

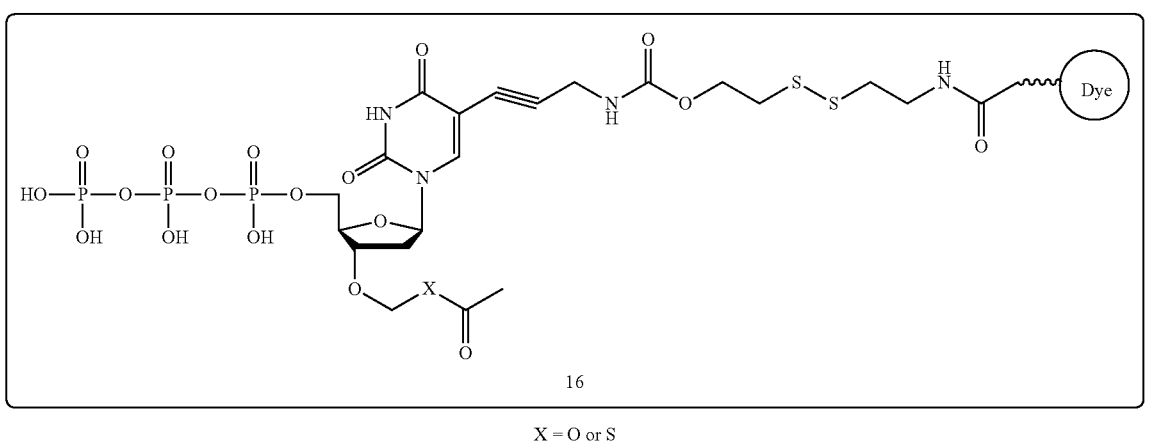

X = O or S

Reagent and conditions: (i) aqueous TFA; (ii) 10, NaHCO₃/Na₂CO₃ buffer (pH 9.2), acetonitrile (iii) Et₃N.3HF, THF, 55° C., 4 h; (iv) (a) 2-chloro-1H-1,3,2-benzodioxaphosphorin-4-one, pyridine, THF, 1.5 h, (b) tributylamine, tributylammonium pyrophosphate, 4 h; (c) tert-butyl hydrogen peroxide, 1 h; (v) aqueous TFA; (vi) fluorescent label-containing succinimidyl ester in DMSO, NaHCO₃/Na₂CO₃ buffer (pH 9.2).

Other nucleotide terminators with deoxy-adenine, cytidine and guanine can be prepared using similar chemistry shown in Schemes 2-4 to afford labeled reversible terminators as shown in FIG. 1.

For example, Schemes 5-6 depict synthetic routes that may provide some novel labeled reversible terminators.

Scheme 5

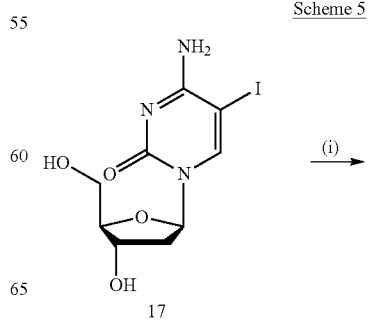

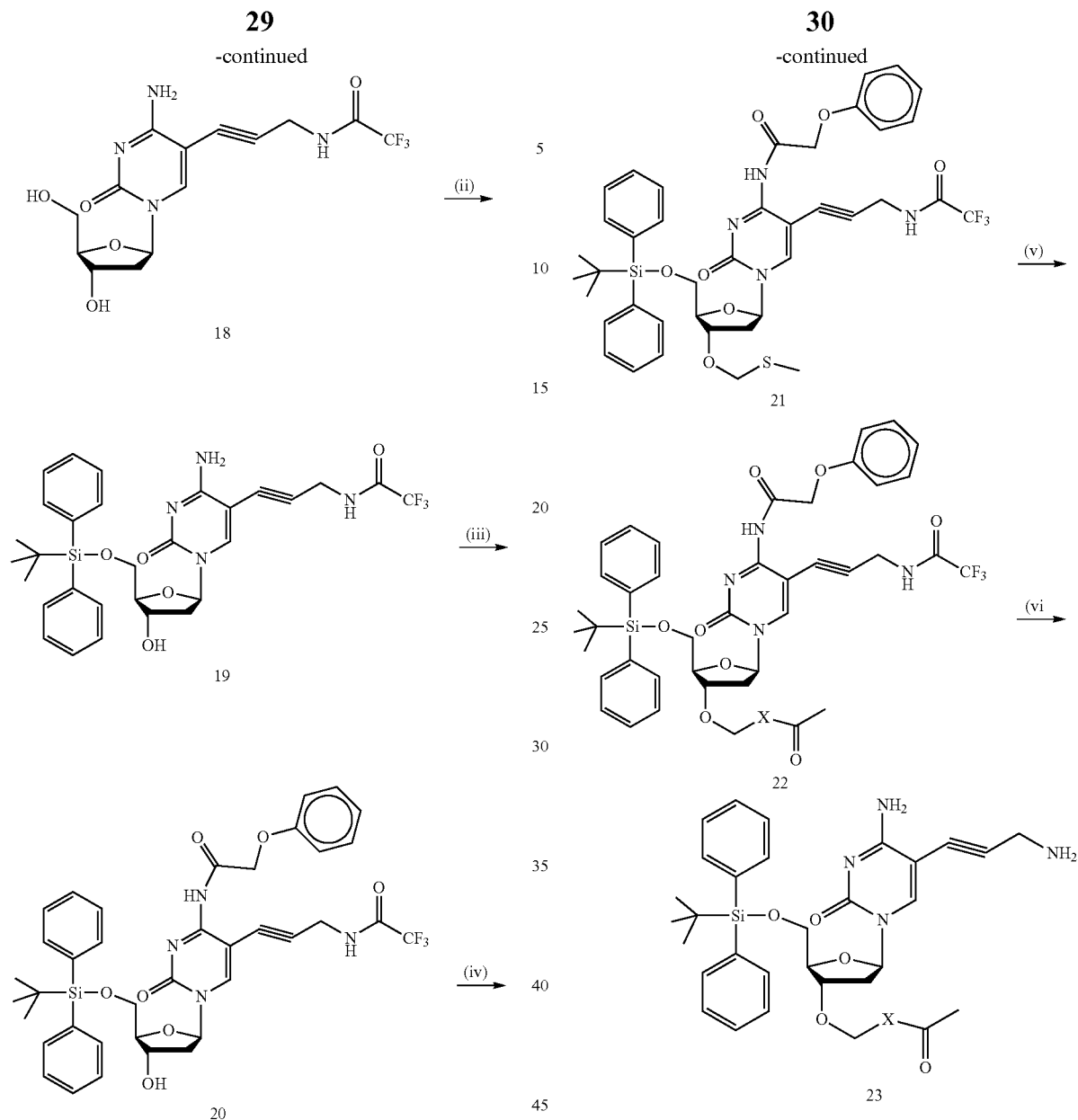
Scheme 6
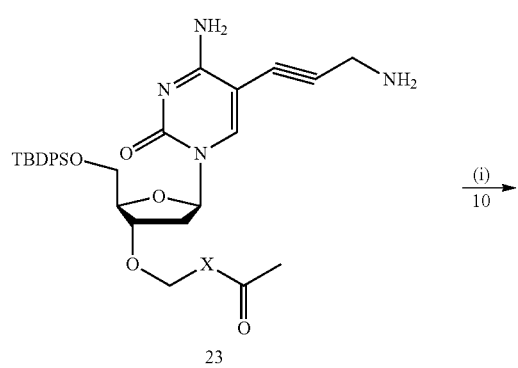

-continued
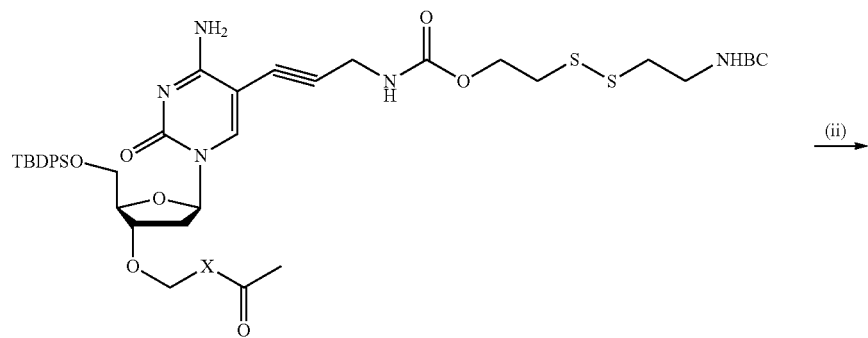
24
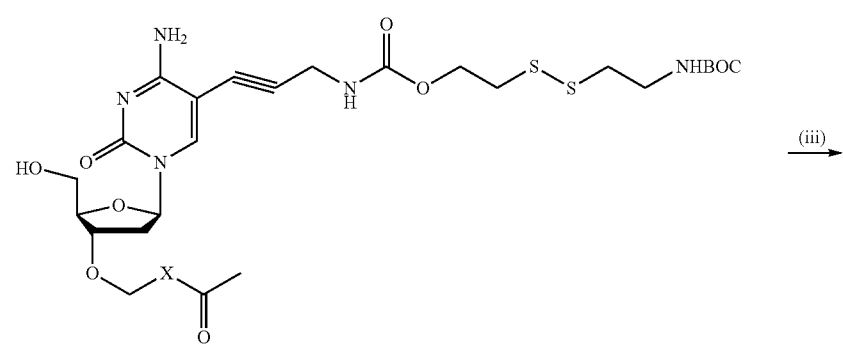
25
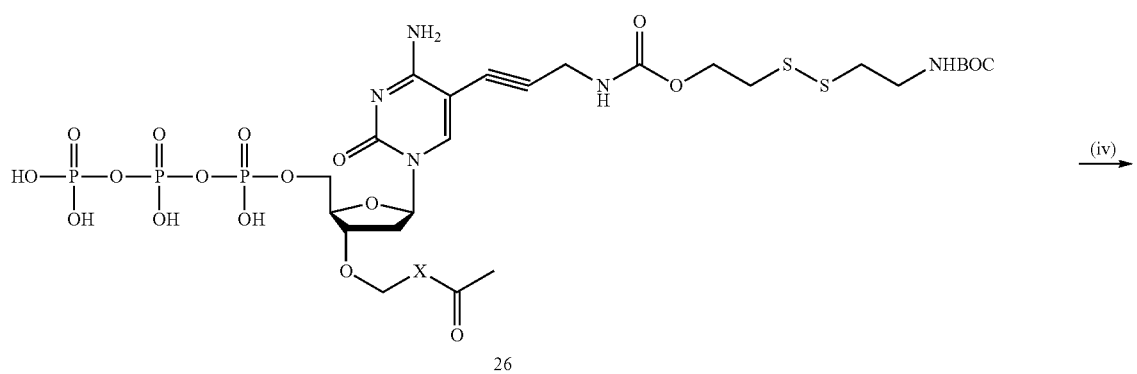
26
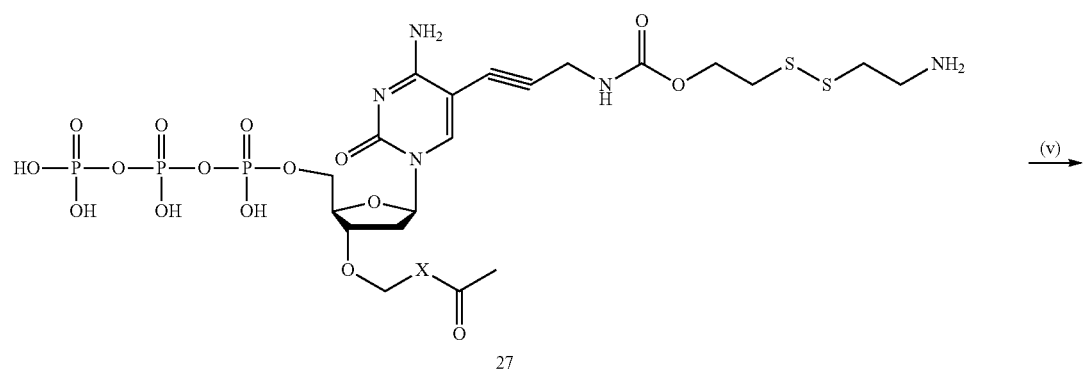
27

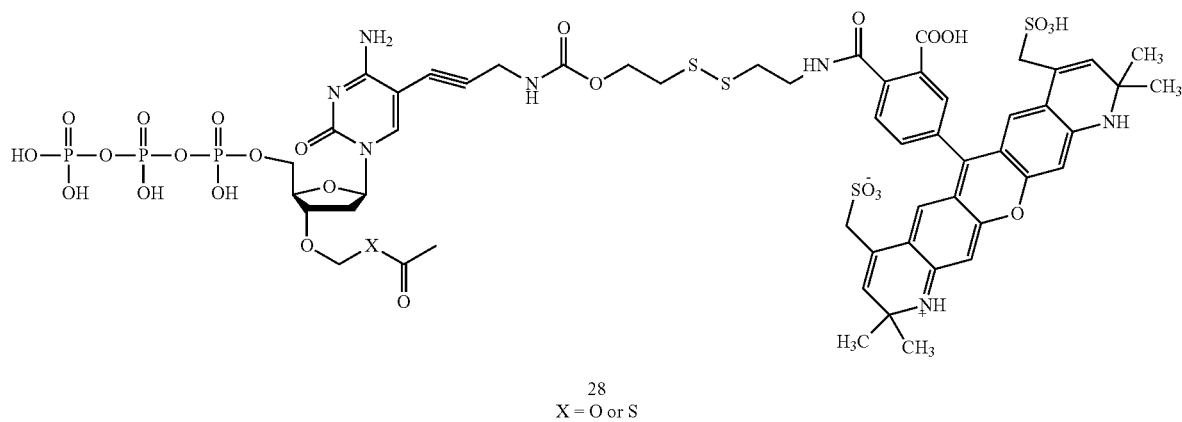

28
X = O or S

The chemical transformations shown in schemes 5-6 can be accomplished in many ways. For example, reagents and conditions used in scheme 5 may be: (i) N-trifluoroacetyl-propargylamine, Pd(PPh₃)₄, CuI, triethylamine, DMF, 12 h; (ii) tert-butyl-diphenylsilylchloride, pyridine RT, 6 h; (iii) (a) chlorotrimethylsilane, pyridine, (b) phenoxyacetic anhydride, DMAP, pyridine, CH₂Cl₂; (iv) DMSO, AcOH, Ac₂O, RT, 12 h; (v) (a) SO₂Cl₂, 0° C., 1 h, (b) potassium salt of acetate or potassium salt of thioacetate, 18-crown-6, DMF, 4 h; (vi) potassium carbonate in methanol, RT, 1 h.

Reagents and conditions used in Scheme 6 may be: (i) 10, NaHCO₃/Na₂CO₃ buffer (pH 9.2), acetonitrile; (ii) Et₃N.3HF, THF, 55° C.; (iii) (a) 2-chloro-1H-1,3,2-benzodioxaphosphorin-4-one, pyridine, THF, (b) tributylamine, tributylammonium pyrophosphate, (c) tert-butyl hydrogen peroxide; (iv) aqueous TFA; (v) ALEXA FLUOR® 568 NHS ester [1,10-Dihydro-2,2,10,10-tetramethyl-4,8-bis(sulfomethyl)-2H-pyrano[3,2-g:5,6-g']diquinolin-6-yl]benzenedicarboxylate-N-ethyl-N-(1-methylethyl)-2-propanamine, NaHCO₃/Na₂CO₃ buffer (pH 9.2).

For example, Schemes 7-8 depict synthetic routes that may provide some novel labeled reversible terminators.

Scheme 7

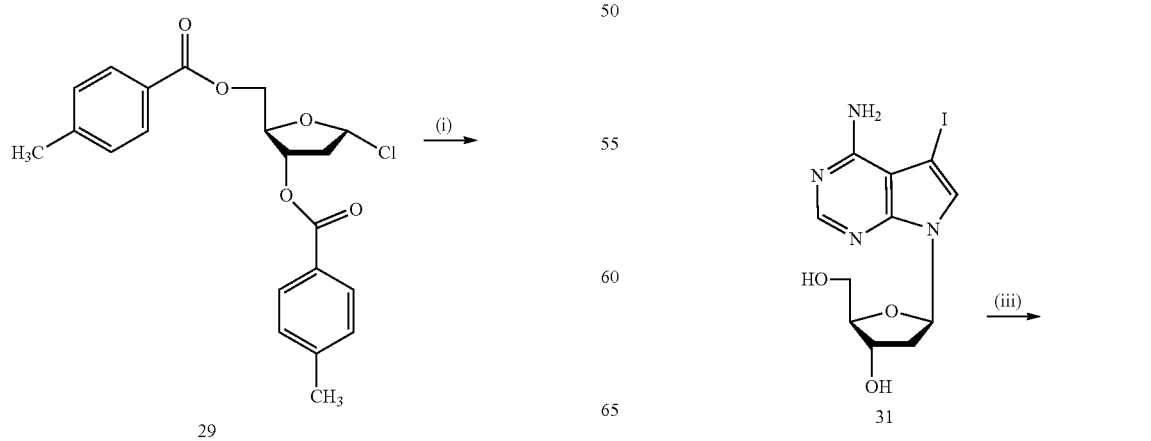

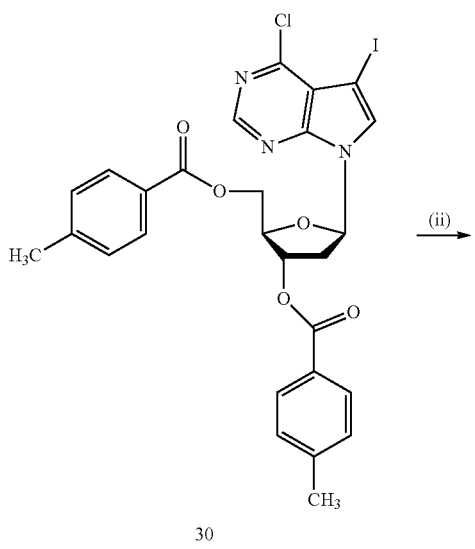

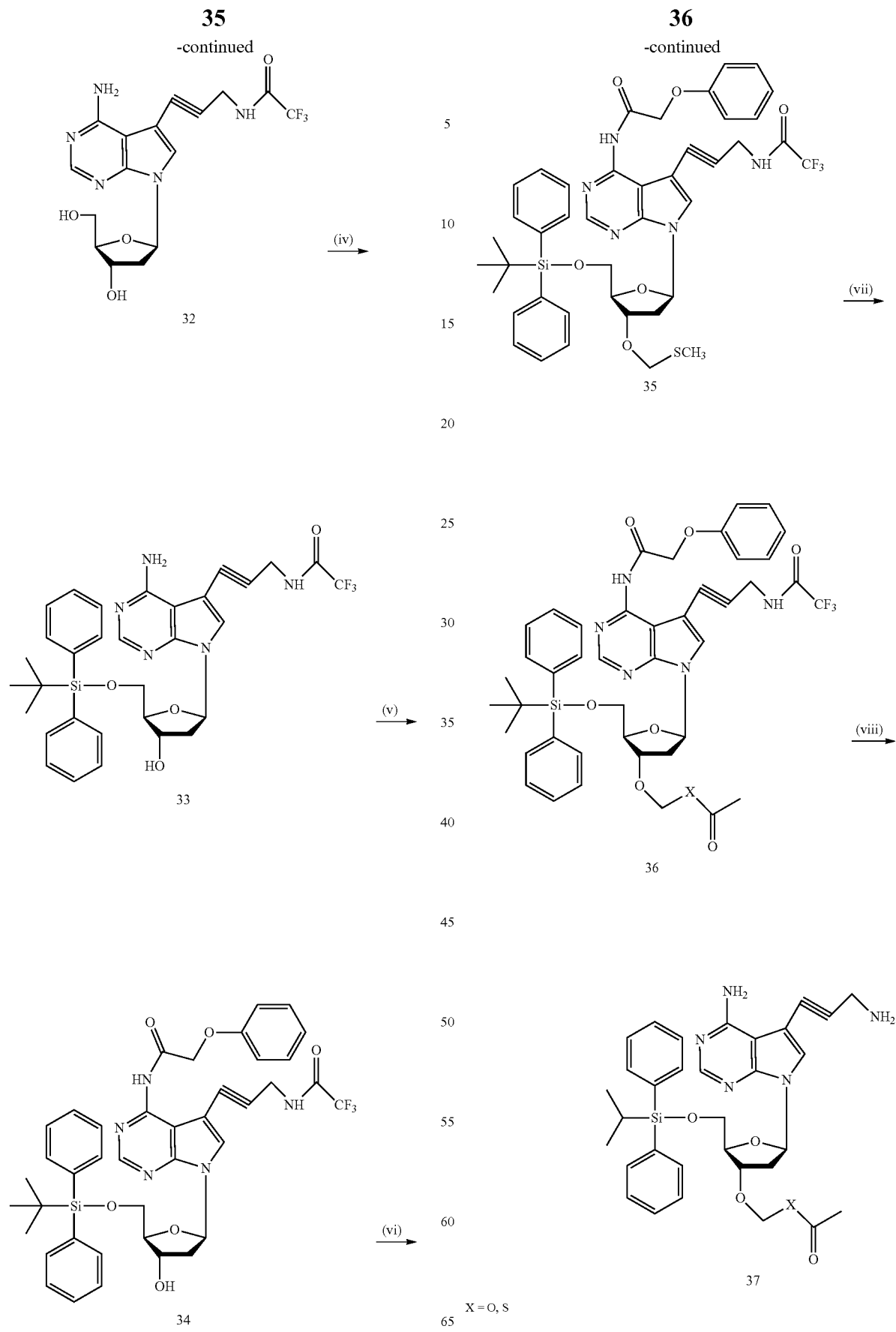

Scheme 8
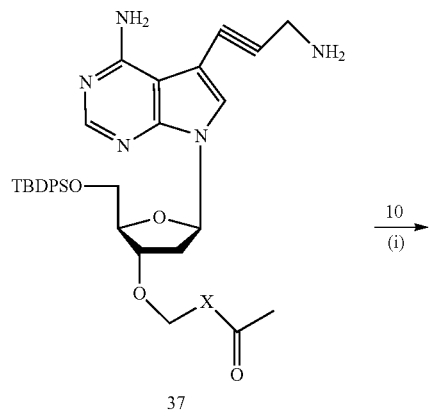
37
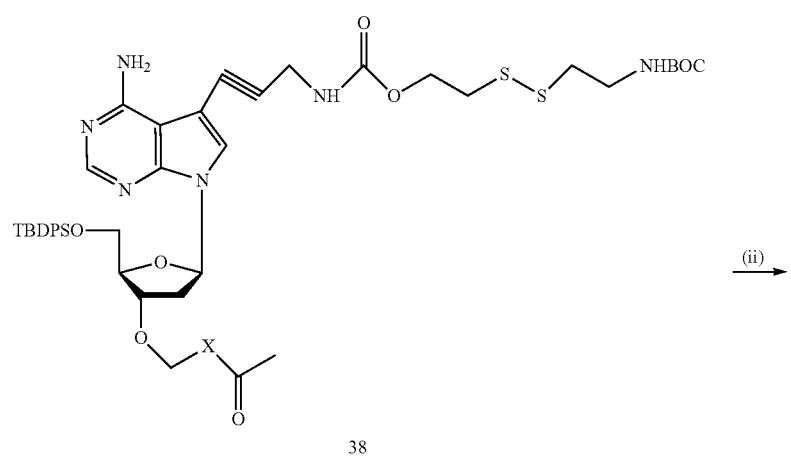
38
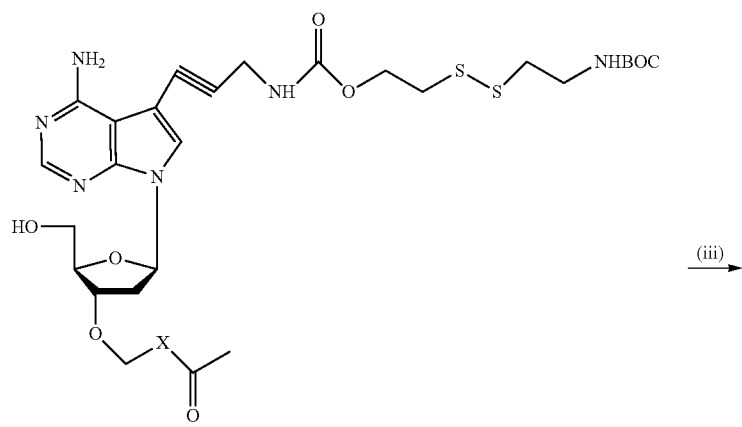
39

-continued

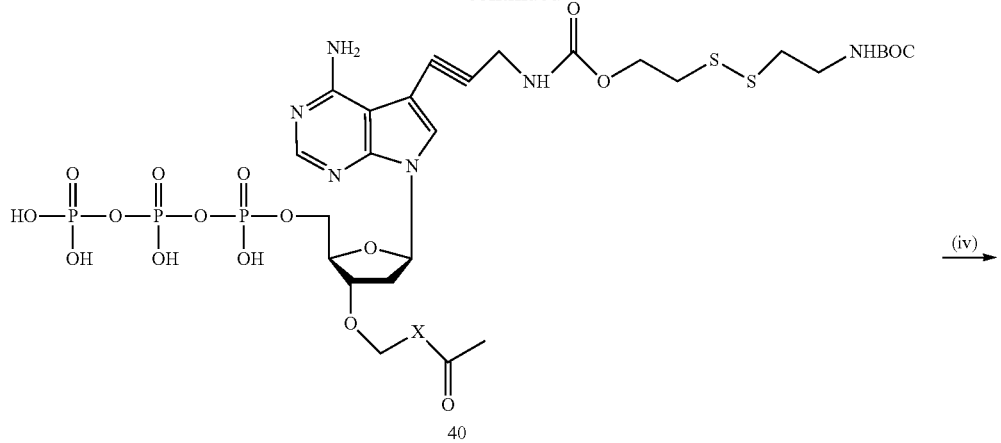

40

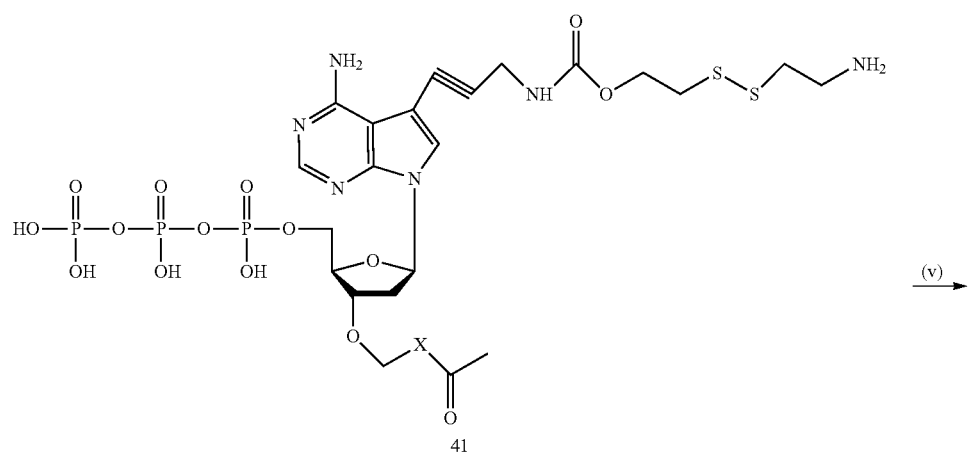

41

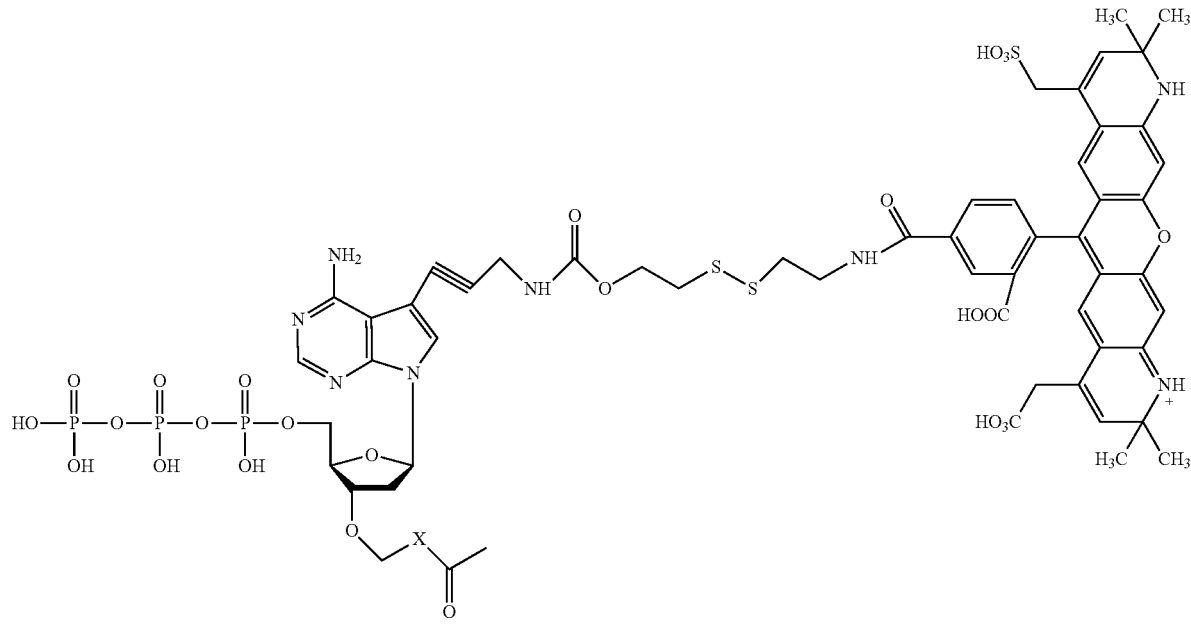

42

X = O or S

The chemical transformations shown in schemes 7-8 can be accomplished in many ways. For example, reagents and conditions used in scheme 7 may be: (i) 4-chloro-5-iodo-7H-pyrrolo[2.3-d]pyrimidine, NaH, ACN; (ii) NH₄OH, MeOH; (iii) N-trifluoroacetylpropargylamine, Pd(PPh₃)₄, CuI, triethylamine, DMF; (iv) tert-butyl-diphenylsilylchloride, pyridine; (v) (a) chlorotrimethylsilane, pyridine, (b) phenoxyacetic anhydride, pyridine, DMAP, CH₂Cl₂; (vi)

DMSO, AcOH, acetic anhydride, RT; (vii) (a) SO₂Cl₂, 0° C., 1 h, (b) potassium salt of acetate or potassium salt of thioacetate, 18-crown-6, DMF, 4 h; (viii) potassium carbonate, methanol, RT, 1 h.

Reagents and conditions: (i) 4-chloro-5-iodo-7 h-pyrrolo [2.3-d]pyrimidine, NaH, ACN; (ii) NH₄OH, MeOH, (iii). N-trifluoro-prop-2-ynyl-acetamide, Pd(PPh₃)₄, CuI, triethylamine, DMF, RT; (iv). tert-butyl-diphenylsilylchloride, pyridine; (v). (a) chlorotrimethylsilane, pyridine, (b) phenoxyacetic anhydride; (vi) DMSO, AcOH, Ac₂O; (vii) a) SOCl₂, 0° C., b) potassium salt of potassium acetate or potassium thioacetate, 18 crown-6, DMF, 4 h; (viii) potassium carbonate, methanol, RT, 1 h.

Reagents and conditions used in Scheme 8 may be: (i) 10, NaHCO₃/Na₂CO₃ buffer (pH 9.2), acetonitrile; (ii) Et₃N.3HF, THF; (iii) (a) 2-chloro-1H-1,3,2-benzodioxaphosphorin-4-one, pyridine, THF, (b) tributylamine, tributylammonium pyrophosphate; (c) tert-butyl hydrogen peroxide; (iv) aqueous TFA, (v) ALEXA FLUOR® 568 NHS ester [1,10-Dihydro-2,2,10,10-tetramethyl-4,8-bis(sulfomethyl)-2H-pyrano[3,2-g:5,6-g']diquinolin-6-yl]benzenedicarboxylate-N-ethyl-N-(1-methylethyl)-2-propanamine, NaHCO₃/Na₂CO₃ buffer (pH 9.2).

For example, Schemes 9-10 depict synthetic routes that may provide some novel labeled reversible terminators.

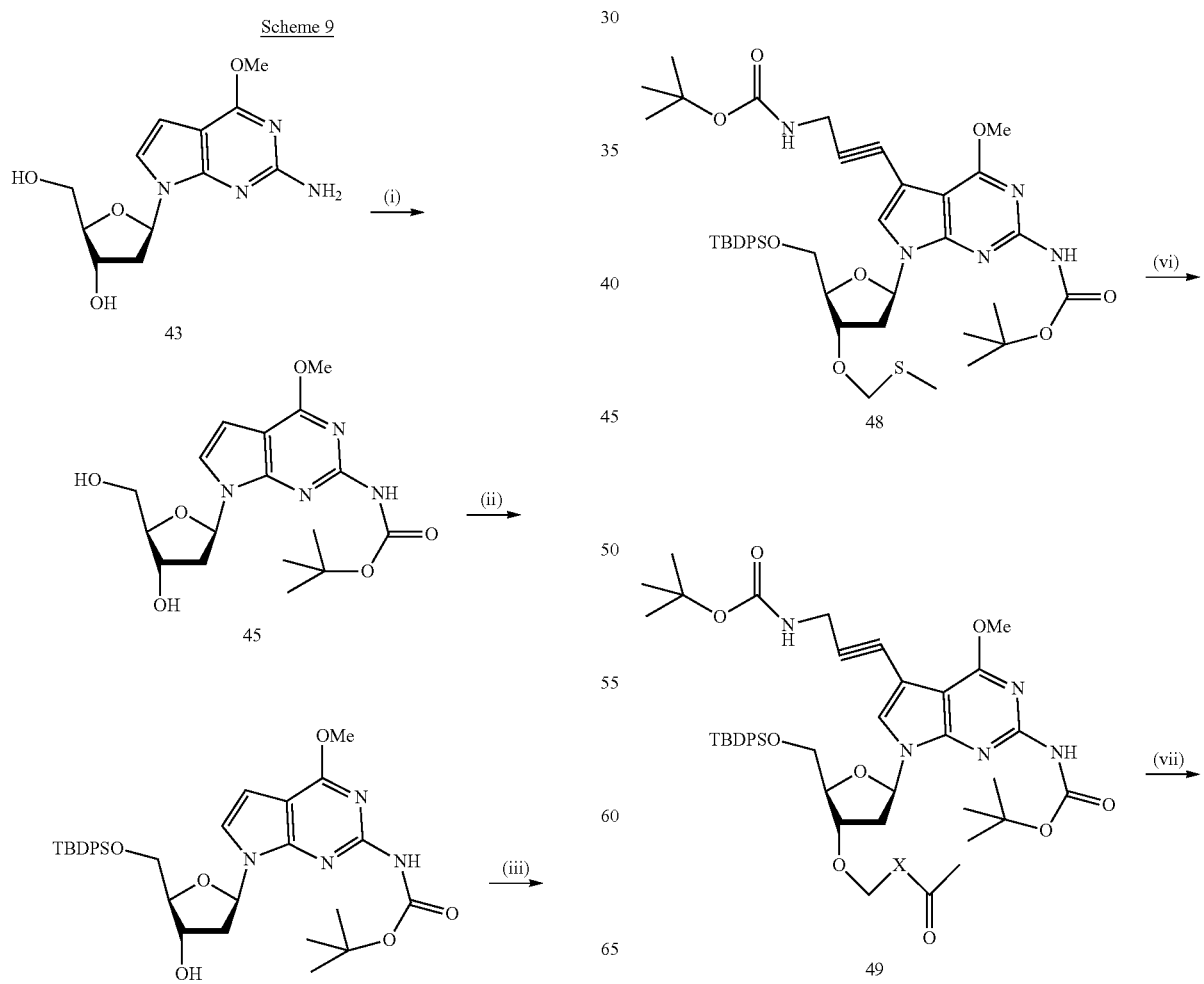

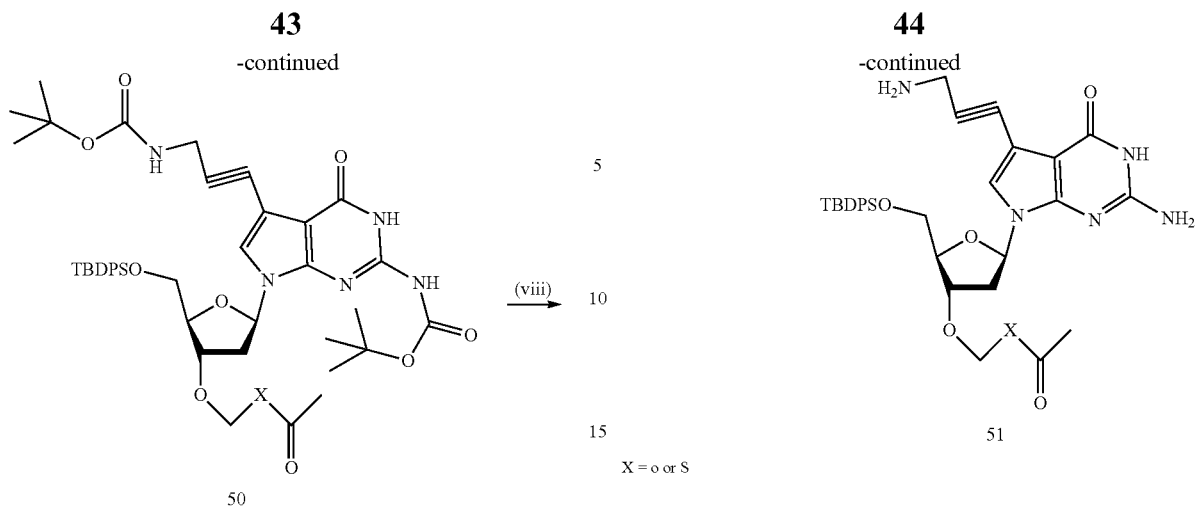
X = O or S
Scheme 10
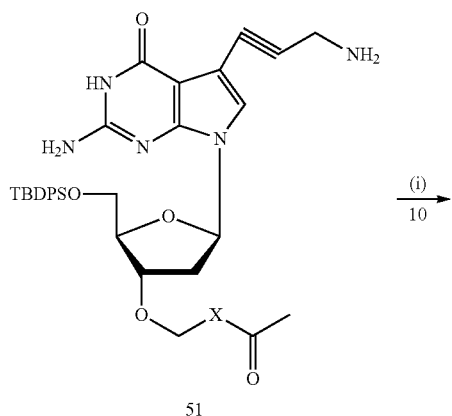
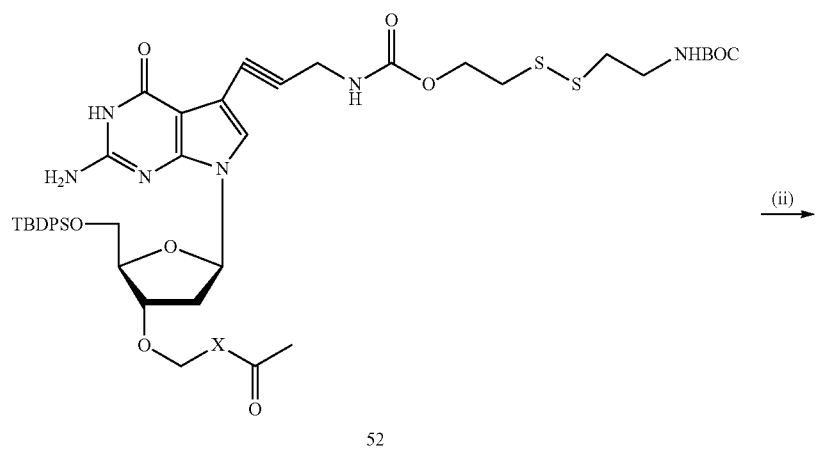

-continued
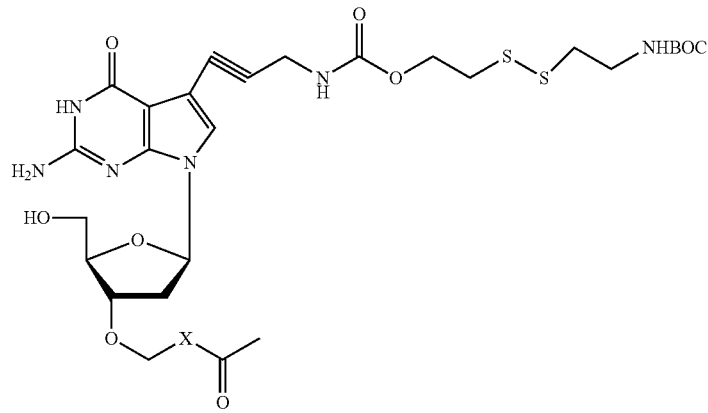
53
(iii) →
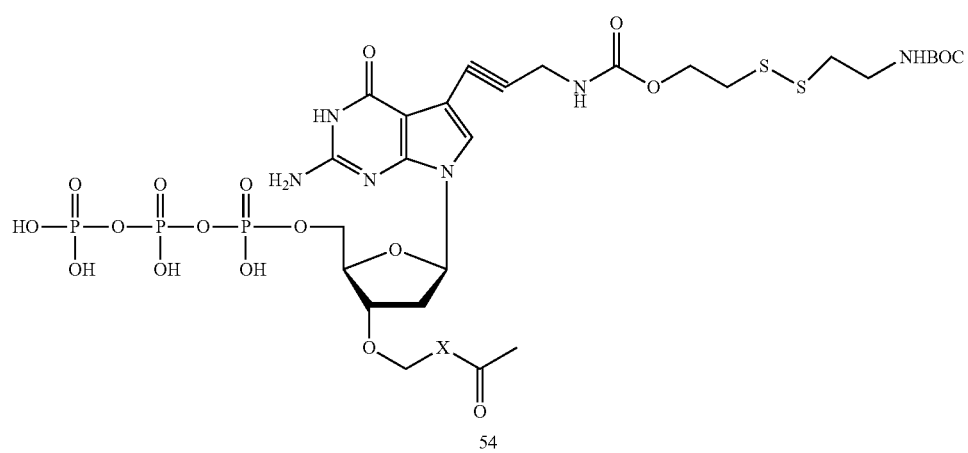
54
(iv) →
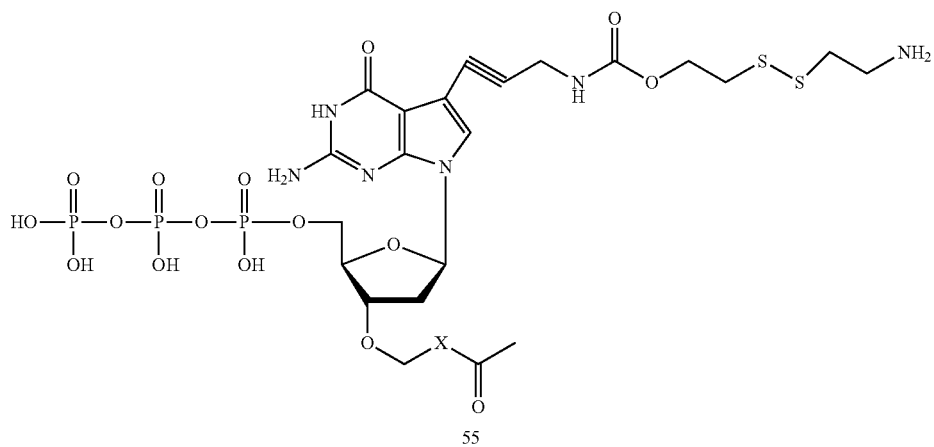
55
(v) →

-continued

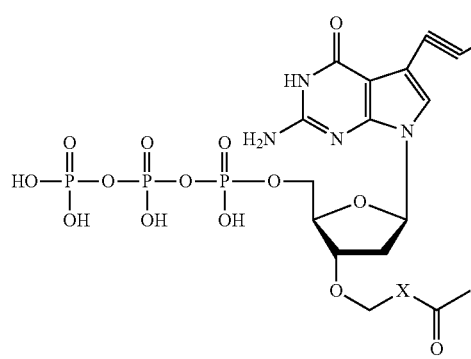 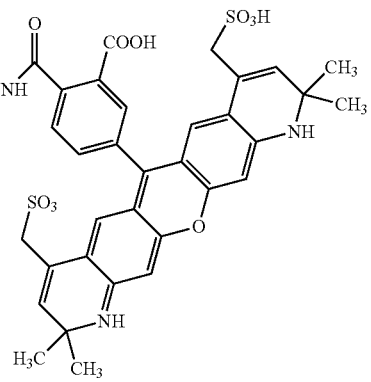

56

X = O or S

The chemical transformations shown in schemes 9-10 can be accomplished in many ways. For example, reagents and conditions used in scheme 9 may be: (i) di-tert-butyl dicarbonate, catalytic DMAP, DMF, RT, 12 h; (b) Aq. NaOH, MeOH, RT, 12 hr; (ii) tert-butyl-diphenylsilylchloride, pyridine; (iii) NIS, DMF, RT, 12 h; (iv) N-trifluoroacetylpropargylamine, Pd(PPh$_3$)$_4$, CuI, triethylamine, DMF, RT, 12 h; (v) DMSO, AcOH, acetic anhydride, RT, 12 h; (vi) (a) SO$_2$Cl$_2$, 0° C., 1 h, (b) potassium salt of acetate or potassium salt of thioacetate, 18-crown-6, DMF, 4 h; (vii) TMSCl, NaI, acetonitrile, RT, 12 h; (ivii) potassium carbonate, methanol, RT, 2 h.

Reagents and conditions used in Scheme 10 may be: (i) 10, NaHCO$_3$/Na$_2$CO$_3$ buffer (pH 9.2), acetonitrile; (ii) Et$_3$N.3HF, THF; (iii) (a) 2-chloro-1H-1,3,2-benzodioxaphosphorin-4-one, pyridine, THF, 1.5 h, (b) tributylamine, tributylammonium pyrophosphate, 4 h; (c) tert-butyl hydrogen peroxide, 1 h; (iv) aqueous TFA; (v) ALEXA FLUOR® 568 NHS ester [1,10-Dihydro-2,2,10,10-tetramethyl-4,8-bis (sulfomethyl)-2H-pyrano[3,2-g:5,6-g']diquinolin-6-yl]benzenedicarboxylate-N-ethyl-N-(1-methylethyl)-2-propanamine, NaHCO$_3$/Na$_2$CO$_3$ buffer (pH 9.2).

Disclosed herein is a new class of fluorescently labeled reversible terminators. The new class of fluorescently labeled reversible terminators can have a 3'-(alkyldisulfanyl) methyl (—CH$_2$—S—S-alkyl) blocking group on the 3'-O of the ribose ring of the nucleotides. The 3'-(alkyldisulfanyl) methyl group-modified nucleotides can be recognized as substrates by DNA polymerase for extension reactions to add to the growing strand during polymerase reactions, and, after being incorporated in the growing strand, can be cleaved under mild conditions. In addition, the fluorophore tags can be linked to the base through a disulfide linkage in connection with a carbamate linker moiety bridging the base and the disulfide group. The fluorophore tags can be cleaved under the same mild conditions to remove the 3'-(alkyldisulfanyl)methyl group from the 3'-O. For example, exposing the new reversible terminators with reducing agents, such as, for example, dithiothreitol (DTT) or 2-mercaptoethanol, may not only break the disulfide bonds of the fluorophore linker and the 3' blocking group, but may trigger a simultaneous cleavage of the carbamate bond by an intramolecular cyclisation in the presence of the of the nascent sulfide anion generated from the disulfide breakage (Scheme 11), thereby removing the sulfide anions from the nucleotide (and the growing chain of the DNA) in the process.

As shown in Scheme 11, Compound A comprises a label D$_1$ linked by a linker L$_3$ to a disulfide bond. The disulfide bond is linked to the nucleotide base B via an amide bond. Compound A also comprises 3'-(alkyldisulfanyl)methyl group on its 3' hydroxyl group. Label D$_1$ may a fluorescent label or fluorophore tag. Linker L$_3$ can be an alkyl group, an alkoxyl group, a carbamate group, an amide group, an ester group, or any combination of at least two of these groups. When Compound A is treated with DTT or 2-mercaptoethanol, both disulfide bonds can be cleaved to afford Compound B as shown. Compound B, a transient intermediate, may comprise two newly generated terminal thiol groups. The thiol group linked to the nucleotide base can undergo spontaneous cyclization while the thiol group linked to the 3' hydroxyl group can undergo spontaneous elimination of thioformaldehyde to generate Compound C, which may not comprise any terminal thiol groups. Consequently, no additional steps are needed to cap the resulting terminal thiol groups on the reversible terminator after both disulfide bonds are cleaved from Compound A.

Although in Compound A, the disulfide group is separated from the carbamate group by two atoms, such as a 1,2-ethylenediyl group, similar spontaneous cleavage can occur when the disulfide group is separated from the carbamate group by three atoms, such as a 1,3-propylenediyl group. Although Scheme 11 shows a triphosphate in the reversible terminator, similar cleavage mechanisms may occur in other type of molecules as long as the same (alkyldisulfanyl) methyl group is at the 3' position and the label D1 is linked to the nucleotide base B in the same or similar ways (i.e., via a disulfide bond which is separate from a carbamate group by an 1,2-ethylenediyl or 1,3-propylenediyl group). Similar mechanism may also occur when the reversible terminators are incorporated into the growing chain (i.e., the triphosphate group in Compound A may change into a phosphodiester group.

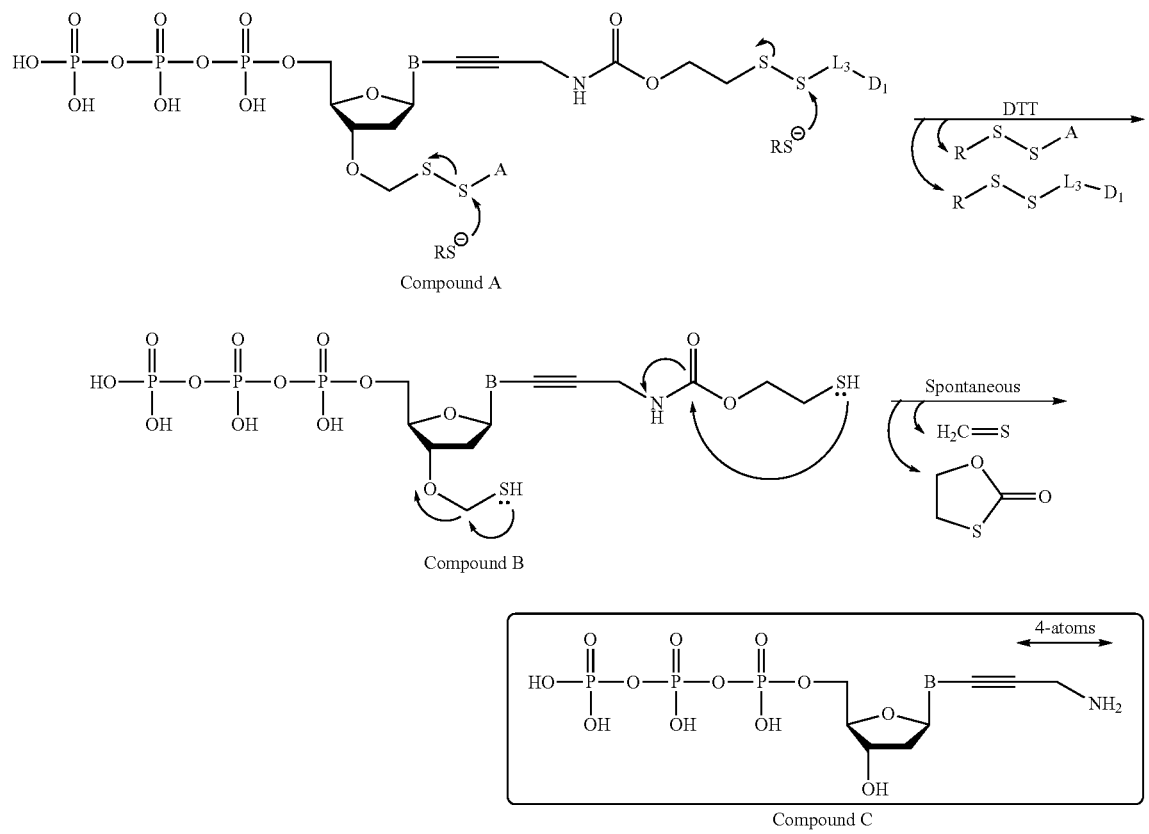

Scheme 11

These novel reversible terminators, after incorporation into the growing chain and cleavage reaction, may comprise, a small (e.g., 4-atom) scar left on the nucleotide base. The elimination of reactive terminal free thiol functional groups may occur after the fluorophore cleavage and/or the simultaneous cleavage of the 3' blocking group. The 4-atom scar may be smaller when compared to with Illumina's 10-atom scar left on the nucleotide bases after the cleavage of the fluorophores. Because the novel reversible terminators may also eliminate reactive free thiol terminal functionality from the remaining portion of the nucleotide after the disulfide cleavages related to both the nucleotide base and the 3' blocking group, the novel reversible terminators may provide many advantages when compared with other reversible terminators having terminal thiol left on the incorporated nucleotide. For example, residual thiols may be undesirable for sequencing reactions because the residual thiols may be reactive in many ways. For instance, the reactive terminal free thiol functional groups may be associated with premature disulfide cleavages on the incoming nucleotide bases when the growing chain is further extended with additional fluorophore-labeled, disulfide-containing nucleotides. Additionally, if the terminal free thiol functional groups react with the incoming nucleotides (comprising reactive groups toward free thiol groups; e.g., a disulfide bond attached to the incoming nucleotide base), new covalent crosslinks may be formed (e.g., forming a disulfide bond with the incoming nucleotide bases or the dyes) such that the incoming nucleotide (or the dye) may be subsequently added to the growing strand as the sequencing process proceeds. This may cleave those disulfide linkers prematurely, releasing the dyes before they can be imaged or erroneously connect with the dye even if the nucleotide base is not complementary to the base on the template. Further, the free thiol groups can form covalent crosslinks with amino acids of proteins (e.g., polymerase) that contain free thiol groups or disulfide bonds. These side-reactions may "gum-up" or interfere with the sequencing process by impeding the polymerase' ability to advance along or dissociate from the elongation complex. In addition, the free thiol groups can form covalent crosslinks with other residual thiols attached to nucleotide bases on the same growing strand or adjacent growing strands being sequenced.

Using the novel reversible terminators as disclosed herein, the DNA sequences may be determined. DNA sequences of the template may be determined by the unique fluorescence emission of the fluorophore tag attached to the nucleotide base. The ensuing cleavage of the disulfide bonds connected with the fluorophore and the simultaneous cleavage of 3' (alkyldisulfanyl)methyl blocking group may trigger spontaneous cleavage of a thiomethylene group to regenerate the free 3'-hydroxy group (Scheme 11). After the two disulfide linkers are broken and the two terminal thiol groups are removed, the 3' hydroxyl group is regenerated for elongation. The continuing elongation of the growing chain may delineate additional sequencing information of the template.

As shown in Scheme 11, a disulfanylalkoxycarbonylamino linked fluorophore tags may be added to the bases of the nucleotides. Exposing the terminators with reducing agent, such as dithiothreitol (DTT) or 2-mercaptoethanol, may reduce and break the disulfide bond, triggering the simultaneous cleavage of the carbamate bond by an intramolecular cyclization of the resulting sulfide anion. In addition, DTT may react with the disulfide bond of the 3' (alkyldisulfanyl)methyl blocking group. Subsequently, the 3' thiomethylene group may spontaneously break down to provide a free hydroxyl group at the 3' position with the concomitant elimination of thioformadehyde. The cleavage of the fluorophore may leave only a small (e.g., 4-atoms) scar on the base (Scheme 11).

It should be noted that although Scheme 11 illustrates a proposed mechanism through which the reversible terminator of the present disclosure can react with a reducing agent, such as DTT or 2-mercaptoethanol, a similar mechanism may occur when the reversible terminator is incorporated into a DNA or RNA growing strand. In that case, the triphosphate moiety of the reversible terminator shown in Scheme 11 may be replaced with a phosphodiester bond linkage to the end of a DNA or RNA growing strand. Accordingly, before the treatment with the reducing agent, because the 3'-OH group of the reversible terminator is capped by the blocking/capping group, the DNA or RNA strand growth may terminate or stop. However, when treated with a reducing agent, such as DTT or 2-mercaptoethanol, the fluorophore attached to the base can be cleaved, and the capping moiety on the 3'-OH group of the sugar can be cleaved simultaneously, similarly to what has been illustrated above in Scheme 11. The exposed 3'-OH group of the incorporated reversible terminator on the end of the DNA or RNA growing strand may allow continued strand growth of the DNA and RNA.

Further, although the reversible terminator shown in Scheme 11 is a triphosphate, other analogs of triphosphate are allowed at the 5' position of the nucleotide, as shown elsewhere in this disclosure.

Figure 3:
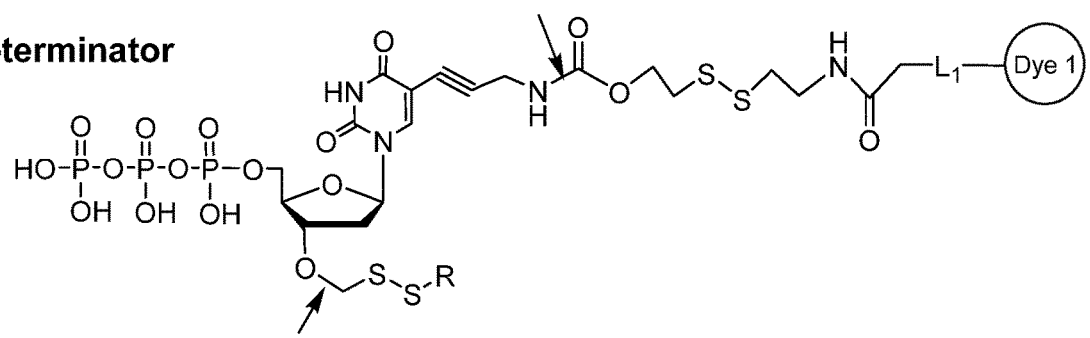
FIG. 3 illustrates another set of nucleotide terminators of the present disclosure with deoxyribose as the sugar and thymine/uracil, adenine, cytidine and guanine as the base. These reversible terminators can be prepared using similar chemistry as provided herein to afford labeled nucleotide reversible terminators.
Figure 3:
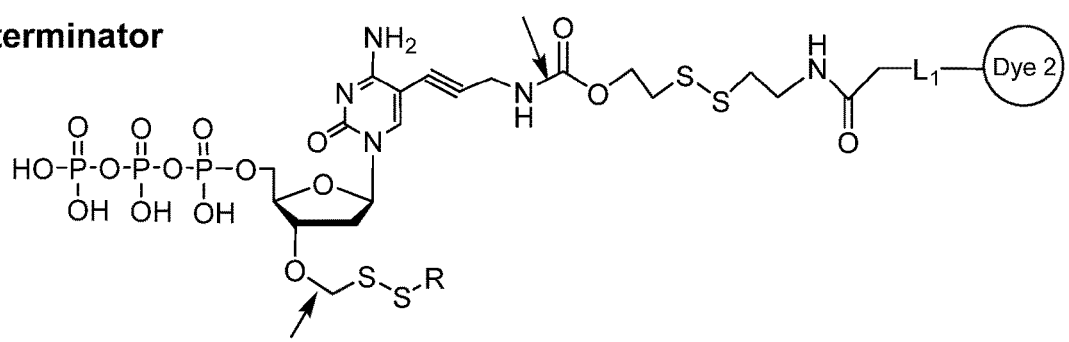
Figure 3:
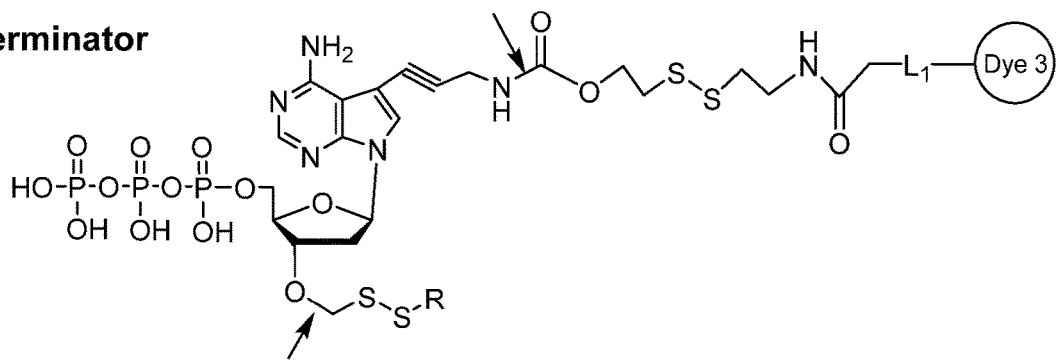
Figure 3:
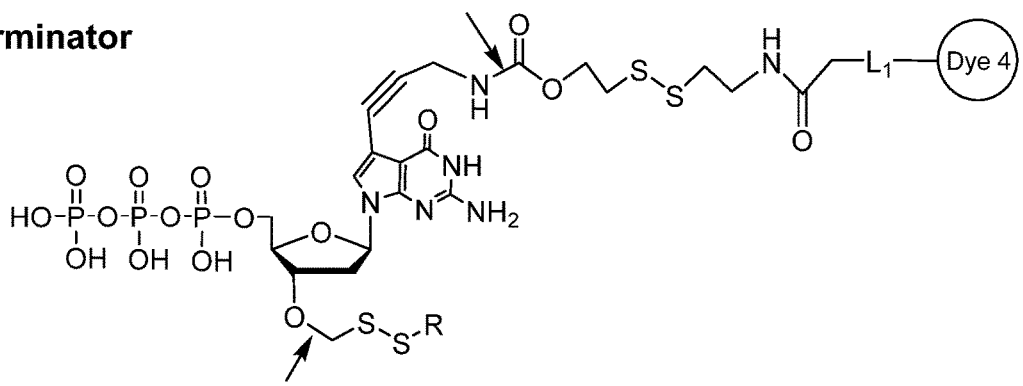

Design and Synthesis of 3'O-Modified Nucleoside Reversible Terminator with Cleavable Disulfide-Linked Fluorescent Tags:

The novel reversible terminators as disclosed may comprise an (alkyldisulfanyl)methyl blocking group on the 3'-OH group of the ribose or deoxyribose, and a fluorophore is tagged to the C-5 position of pyrimidines (C and U) or the C-7 position of purine bases (A and G) through a disulfide linkage as shown in FIG. 3. The arrows indicate the positions at which the linked fluorescent tags from the base or the 3' (alkyldisulfanyl)methyl blocking group can be cleaved.

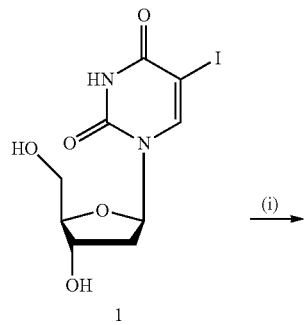

Scheme 12

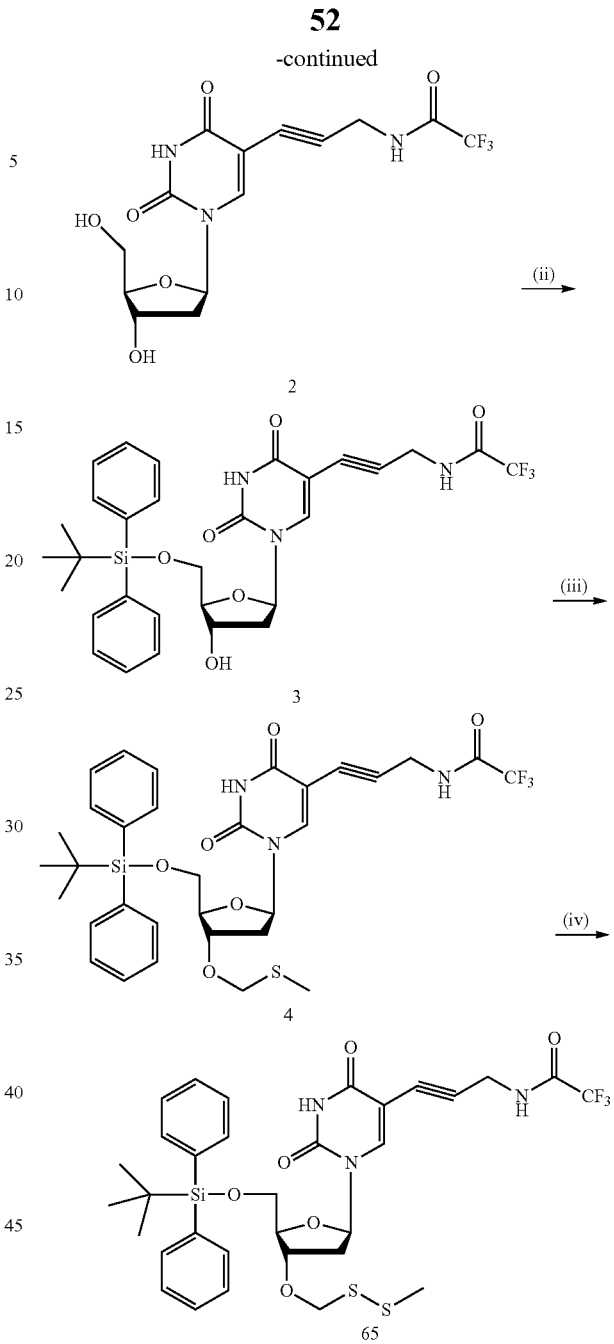

Reagents and conditions: (i) N-trifluoroacetylpropargylamine, Pd (PPh$_3$)$_4$, CuI, triethylamine, DMF, room temperature (RT), 12 h; (ii) tert-butyldiphenylsilylchloride, pyridine, RT, 6 h; (iii) DMSO, AcOH, acetic anhydride, room temperature (RT), 12 h; (iv) (a) SO$_2$Cl$_2$, 0° C., 1 h, (b) potassium p-toluenethiosulfonate, RT, 2 h, (c) sodium thiomethoxide, RT, 1.5 h.

The synthesis of modified uridine reversible terminator can be carried out as shown in Scheme 12, which depicts a reaction scheme leading to the synthesis of N-(3-(1-((2R, 4S,5R)-5-(((tert-butyldiphenylsilyl)oxy)methyl)-4-((methyldisulfaneyl)methoxy)tetrahydrofuran-2-yl)-2,4-dioxo-1,2, 3,4-tetrahydropyrimidin-5-yl)prop-2-yn-1-yl)-2,2,2-trifluoroacetamide (65), an intermediate leading to a modified uridine nucleotide. A palladium-catalyzed Sonogashira coupling of 5-iodo-2'deoxyuridine (1) with N-trifluoroacetylpropargylamine provided 2,2,2-trifluoro-N-(3-(1-((2R,4S,5R)-4-hydroxy-5-(hydroxymethyl)tetrahydrofuran-2-yl)-2,4-dioxo-1,2,3,4-tetrahydropyrimidin-5-yl)prop-2-yn-1-yl)acetamide (2). Silylation of 2,2,2-trifluoro-N-(3-(1-((2R,4S,5R)-4-hydroxy-5-(hydroxymethyl)tetrahydrofuran-2-yl)-2,4-dioxo-1,2,3,4-tetrahydropyrimidin-5-yl)prop-2-yn-1-yl)acetamide (2) afforded N-(3-(,5R)-4-hydroxy-5-(hydroxymethyl)tetrahydrofuran-2-yl)-2,4-dioxo-1,2,3,4-1-((2R,4S,5R)-5-(((tert-butyldiphenylsilyl)oxy)methyl)-4-hydroxytetrahydrofuran-2-yl)-2,4-dioxo-1,2,3,4-tetrahydropyrimidin-5-yl)prop-2-yn-1-yl)-2,2,2-trifluoroacetamide (3). Conversion of the 3'-hydroxy group in 3 to 3'-(methylthio)methoxy using DMSO, acetic acid and acetic anhydride by Pummerer's rearrangement provided intermediate N-(3-(1-((2R,4S,5R)-5-(((tert-butyldiphenylsilyl)oxy)methyl)-4-((methylthio)methoxy)tetrahydrofuran-2-yl)-2,4-dioxo-1,2,3,4-tetrahydropyrimidin-5-yl)prop-2-yn-1-yl)-2,2,2-trifluoroacetamide (4). Then the 3' functional group was further converted in-situ to 3'-O-chloromethyl using sulfuryl chloride, followed by in-situ replacement of the chloride by the p-toluenesulfonothioate group, which reacted further with thiomethoxide (with the elimination of p-toluenesulfinate) to give disulfide-containing intermediate (65).

After these two intermediates 65 and 10 are synthesized, the novel reversible terminators may be synthesized, for example, according to steps shown in Scheme 13. Removal of the trifluoroacetyl group from 65 using methanolic ammonia, followed by condensation with activated linker 10 may afford 71. Removal of 5'-silyl group by treating 71 with tetrabutylammonium fluoride, followed by phosphorylation of the free 5'-OH on the ribose may afford the triphosphate 73. Finally, removal of the BOC group on 73 and condensation of resulting primary amine in 74 with N-hydroxysuccinimide (NHS) ester of a dye may afford a nucleoside reversible terminator 75. Because the 3' blocking group is a disulfide which may be removed by a reducing agent, the 3' blocking group can be removed simultaneously with the disulfide linked dye connected to the nucleotide base.

Scheme 13

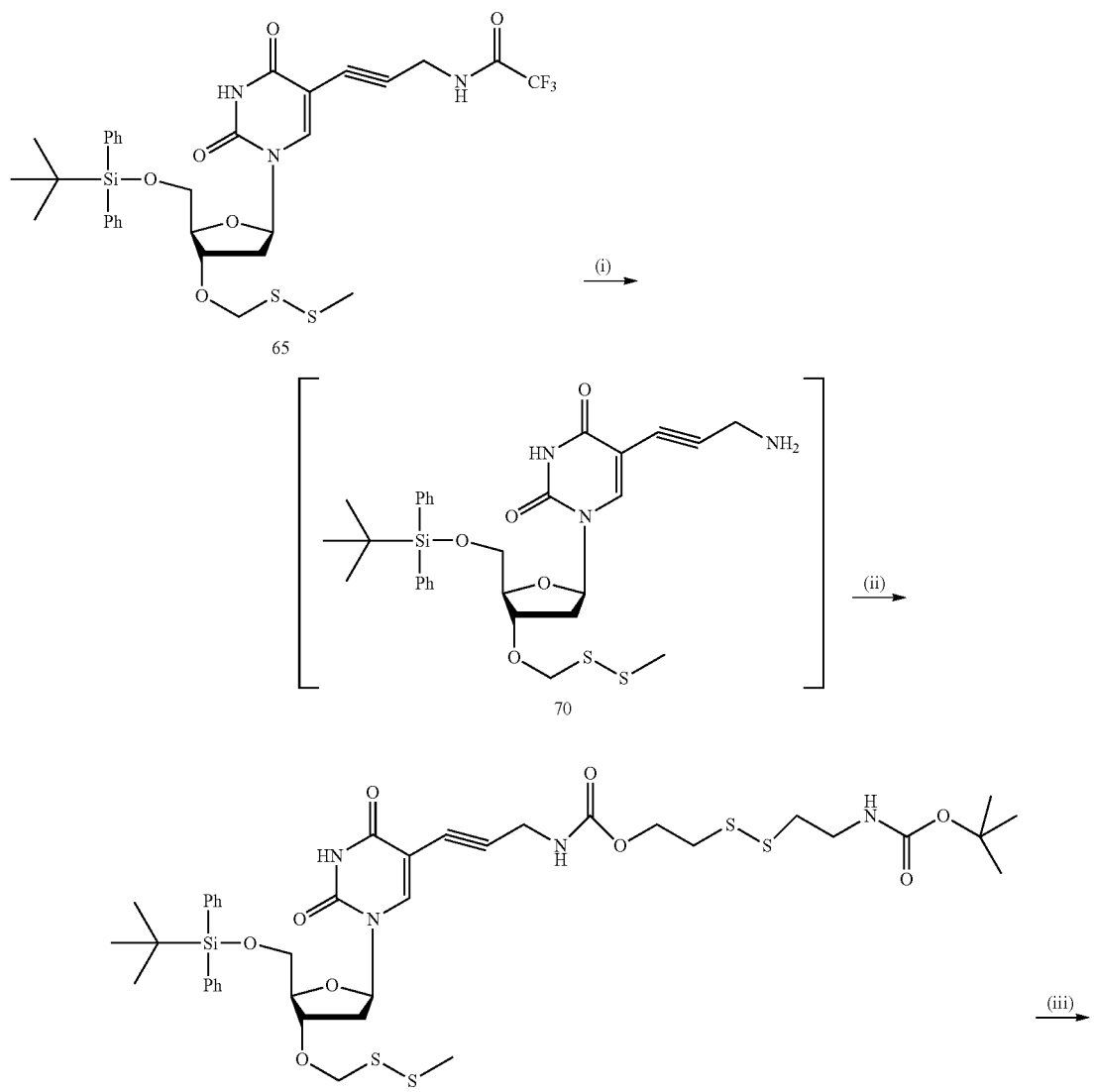

-continued

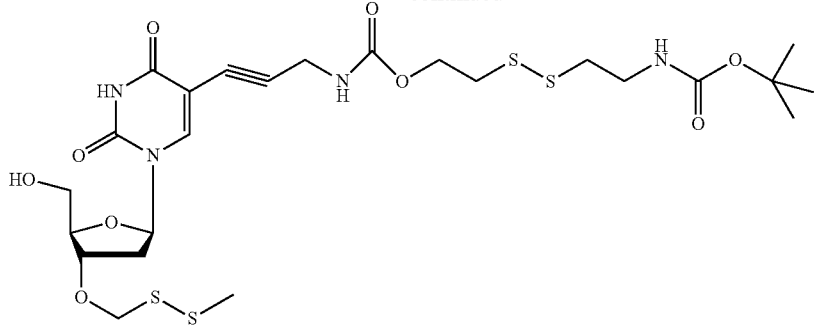
72

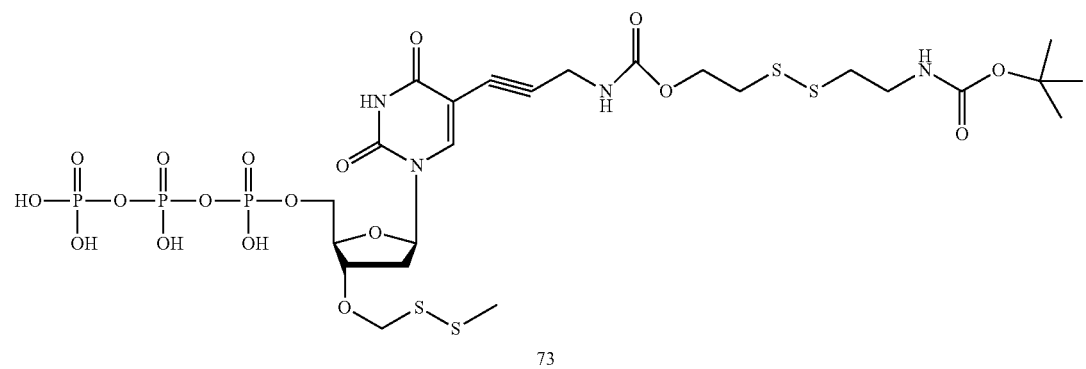
73

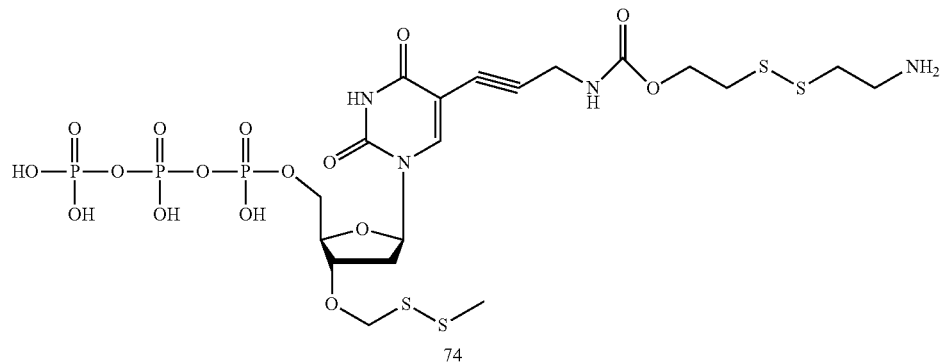
74

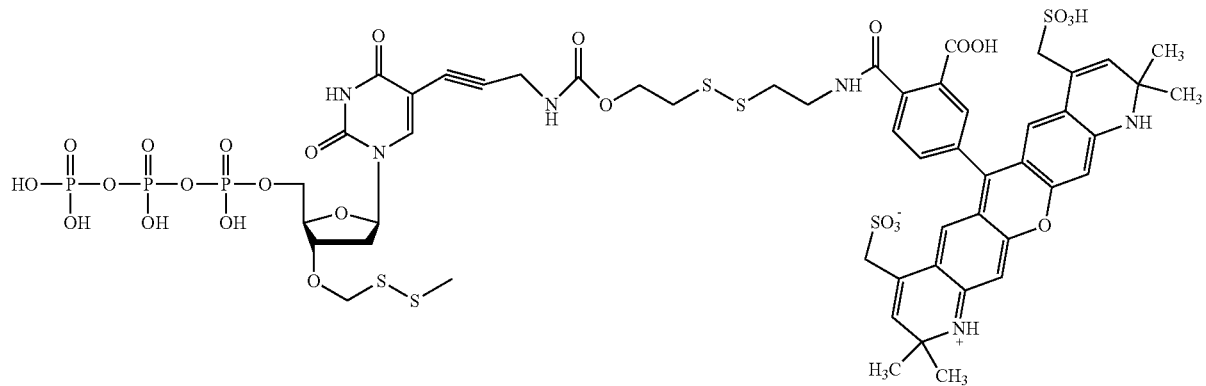
75

Reagent and conditions: (i) methanolic ammonia, RT, 12 h; (ii) 10, NaHCO$_3$/Na$_2$CO$_3$ buffer (pH 9.2), acetonitrile (iii) Et$_3$N.3HF, THF, RT, 12 h; (iv) (a) 2-chloro-1H-1,3,2-benzodioxaphosphorin-4-one, pyridine, THF, 1 h, (b) tributylamine, tributylammonium pyrophosphate, 1.5 h; (c) tert-butyl hydrogen peroxide, 1 h; (v) aqueous TFA; (vi) ALEXA FLUOR® 568 NHS ester [1,10-Dihydro-2,2,10,10-tetramethyl-4,8-bis(sulfomethyl)-2H-pyrano[3,2-g:5,6-g'] diquinolin-6-yl]benzenedicarboxylate-N-ethyl-N-(1-methylethyl)-2-propanamine, NaHCO$_3$/Na$_2$CO$_3$ buffer (pH 9.2).

Other nucleotide terminators with deoxy-adenine, cytidine and guanine can be prepared using similar chemistry shown in Schemes 12-13 to afford labeled reversible terminators as shown in FIG. 3.
For example, Schemes 14-15 depict synthetic routes that may provide some novel labeled reversible terminators.
Scheme 14
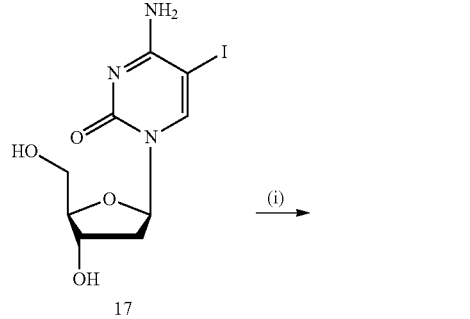
17
(i)
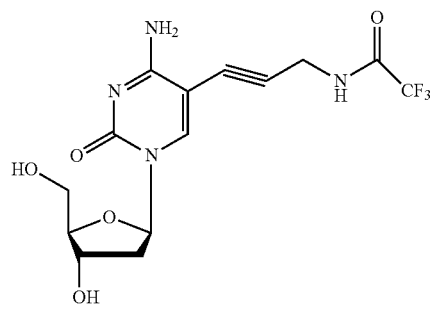
18
(ii)
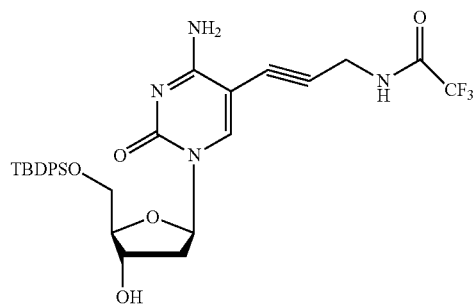
19
(iii)
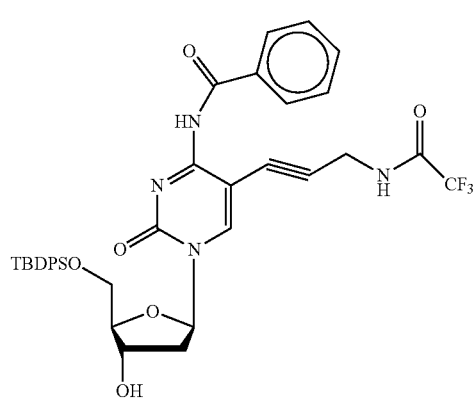
79
(iv)
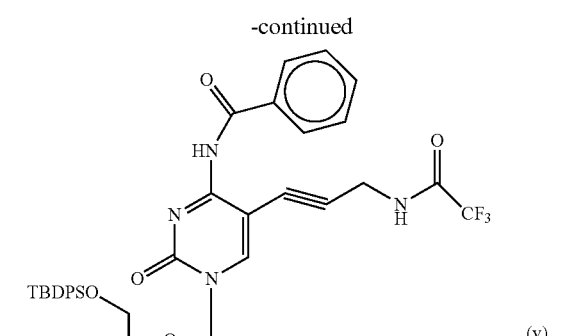
80
(v)
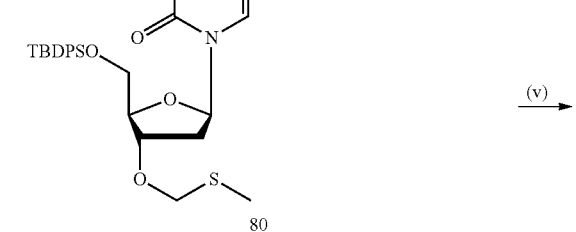
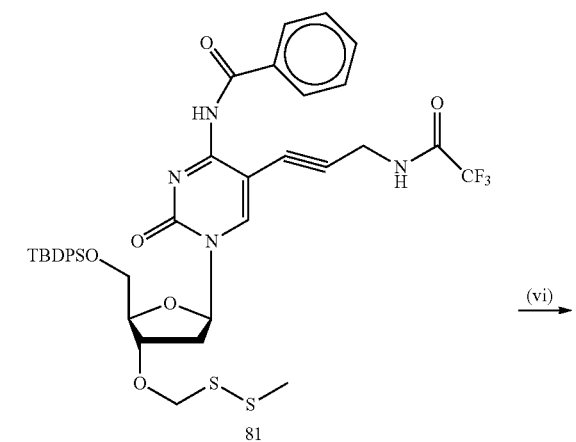
81
(vi)
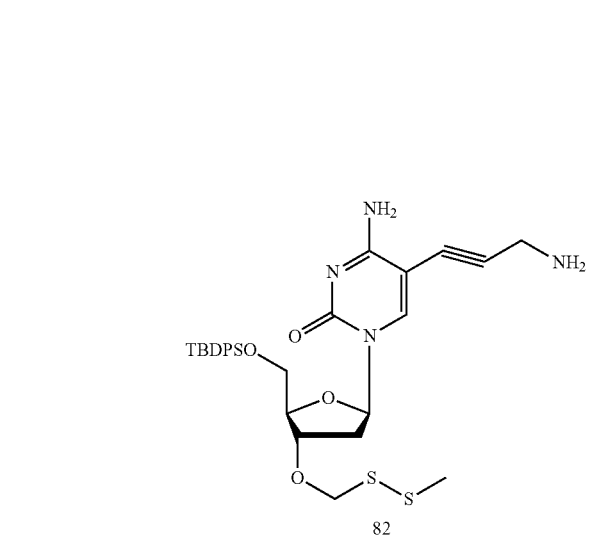
82

Scheme 15
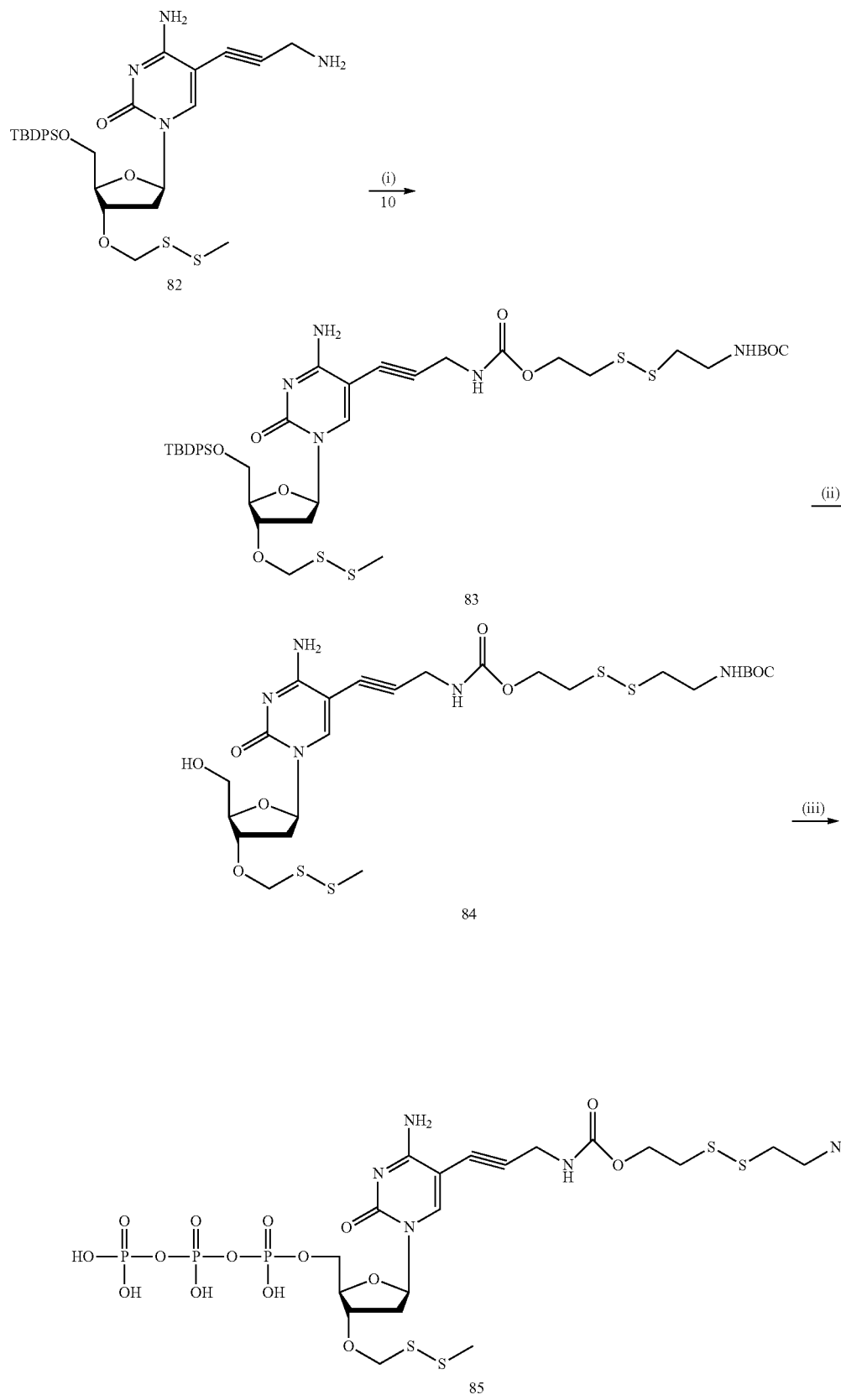

-continued

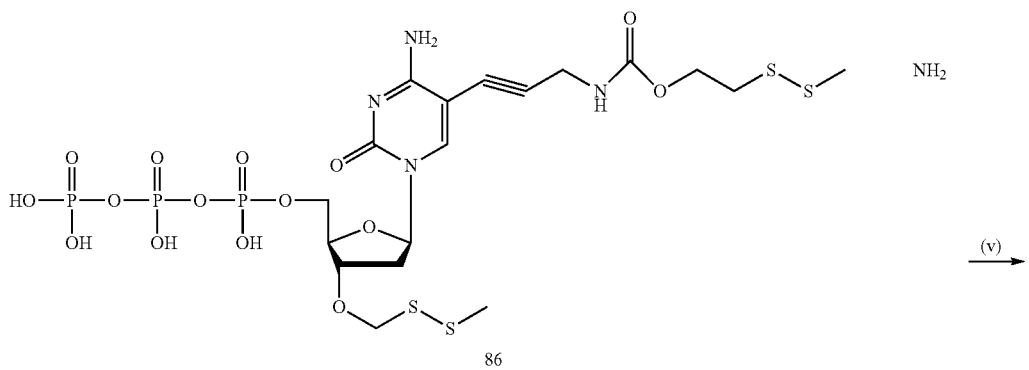

86

(v) →

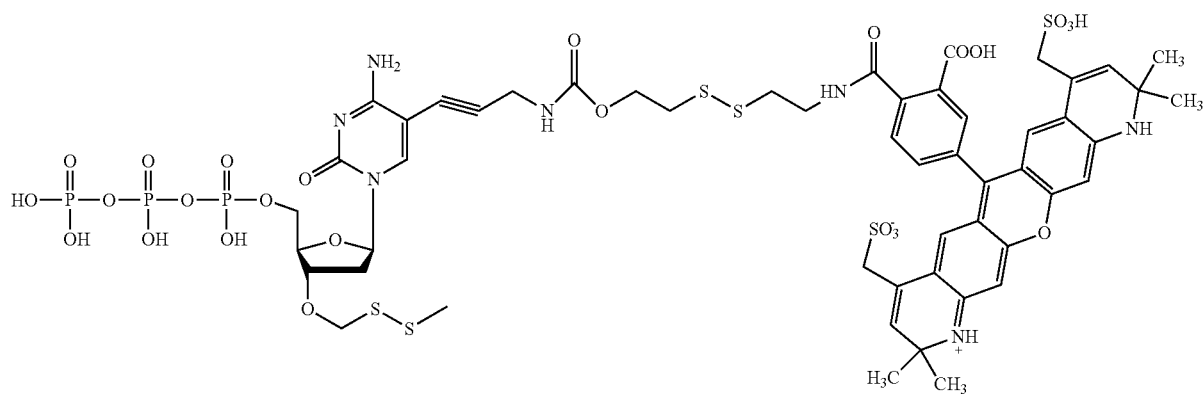

87

The chemical transformations shown in schemes 14-15 can be accomplished in many ways. For example, reagents and conditions used in scheme 14 may be: (i) N-trifluoroacetylpropargylamine, Pd(PPh$_3$)$_4$, CuI, triethylamine, DMF; (ii) tert-butyl-diphenylsilylchloride, pyridine; (iii) (a) chlorotrimethylsilane, pyridine, (b) benzoyl chloride; (iv) DMSO, AcOH, acetic anhydride; (v) (a) SO$_2$Cl$_2$, (b) potassium p-toluenethiosulfonate, (c) sodium thiomethoxide, RT; (vi) methanolic ammonia. Reagents and conditions used in Scheme 15 may be: (i) 10, NaHCO$_3$/Na$_2$CO$_3$ buffer (pH 9.2), acetonitrile; (ii) Et$_3$N.3HF, THF; (iii) (a) 2-chloro-1H-1,3,2-benzodioxaphosphorin-4-one, pyridine, THF, (b) tributylamine, tributylammonium pyrophosphate, (c) tert-butyl hydrogen peroxide; (iv) aqueous TFA; (v) ALEXA FLUOR® 568 NHS ester [1,10-Dihydro-2,2,10,10-tetramethyl-4,8-bis(sulfomethyl)-2H-pyrano[3,2-g:5,6-g']diquinolin-6-yl]benzenedicarboxylate-N-ethyl-N-(1-methylethyl)-2-propanamine, NaHCO$_3$/Na$_2$CO$_3$ buffer (pH 9.2).

For example, Schemes 16-17 depict synthetic routes that may provide some novel labeled reversible terminators.

Scheme 16

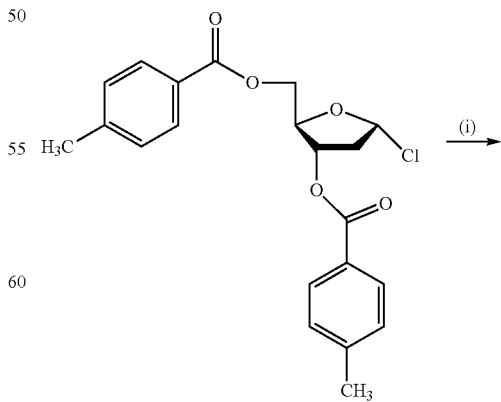

29

(i) →

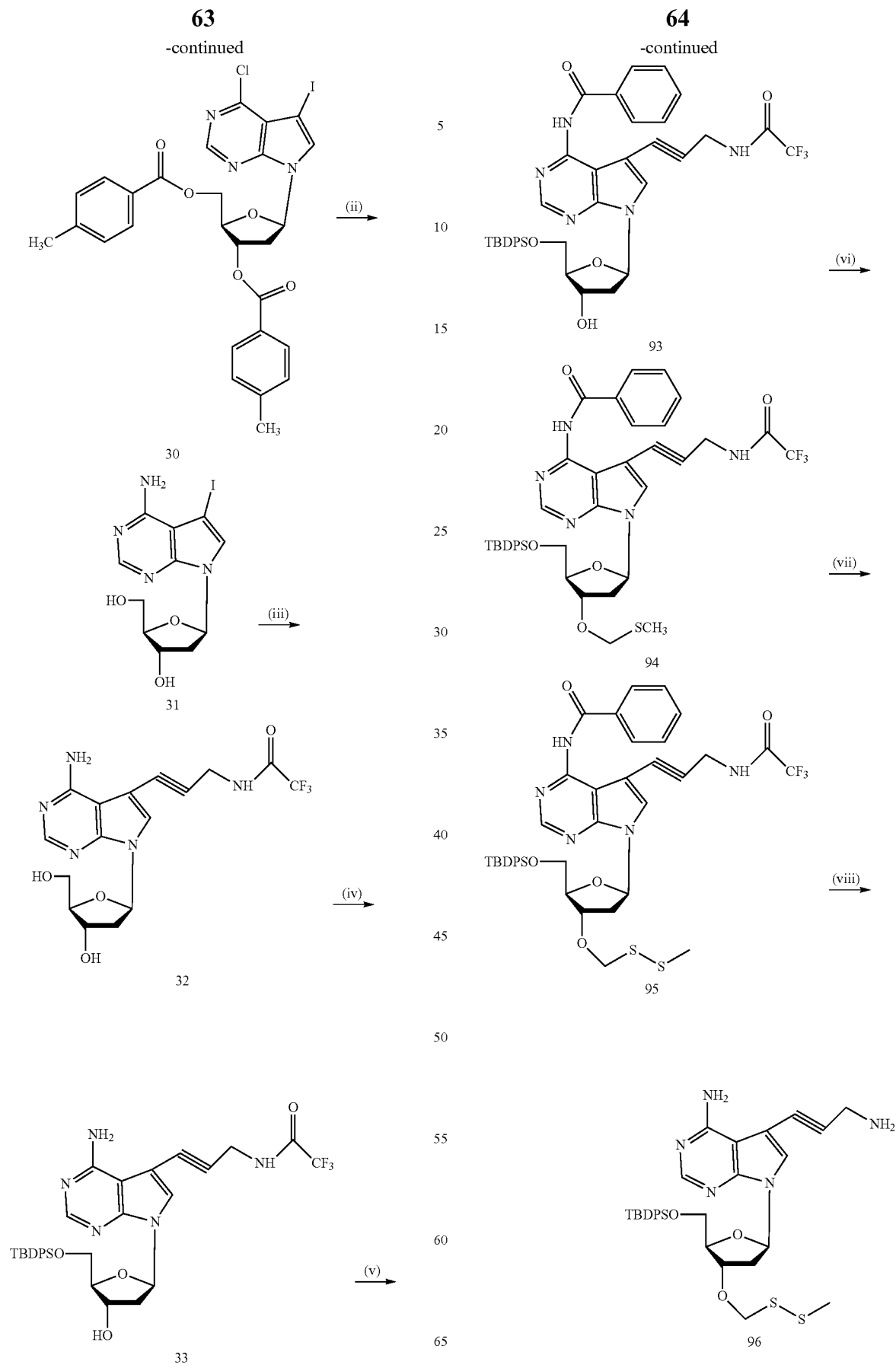

Scheme 17
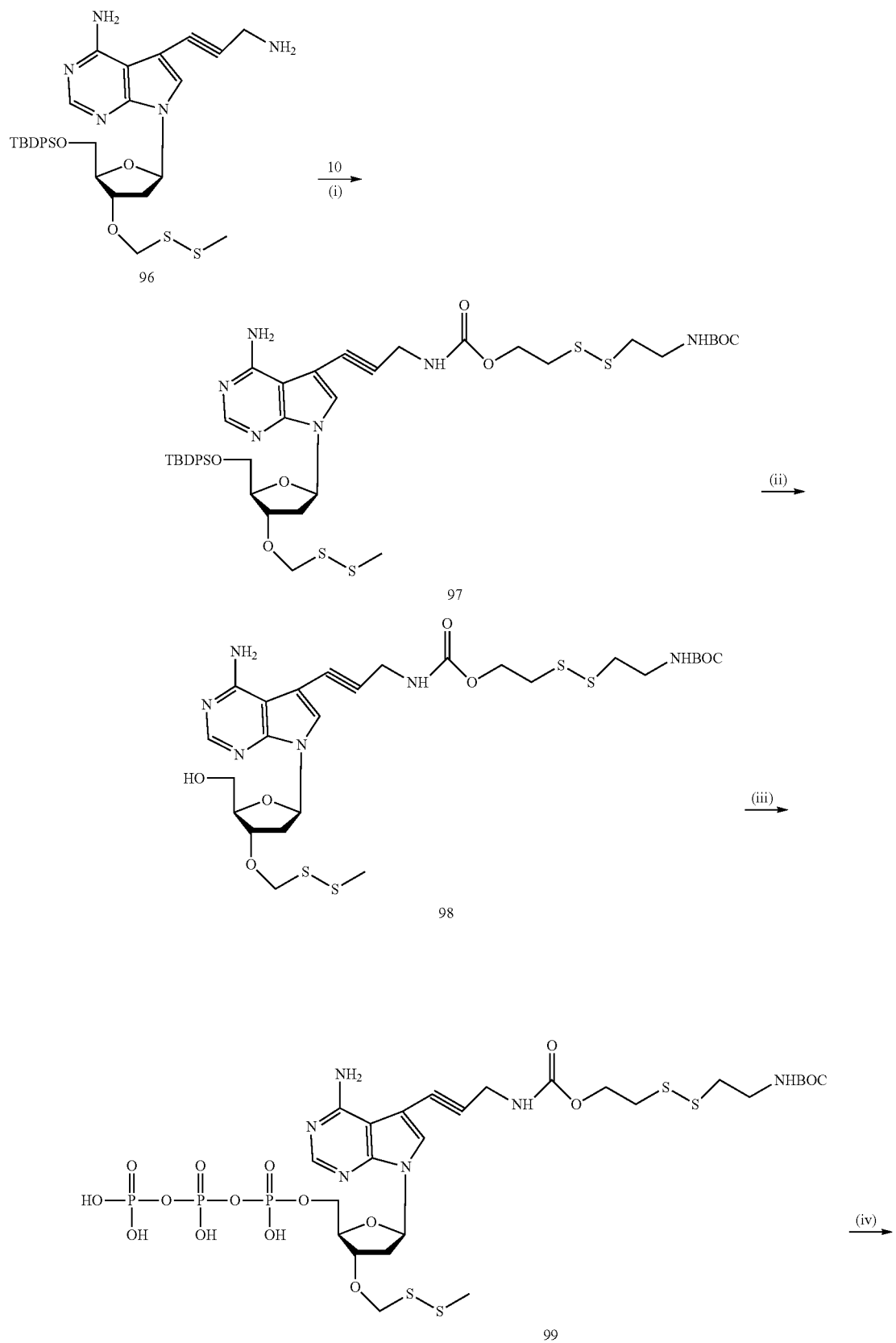

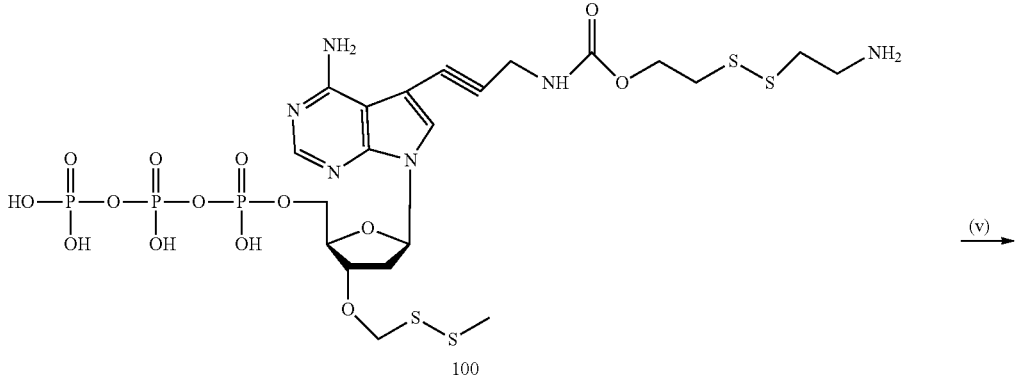

100

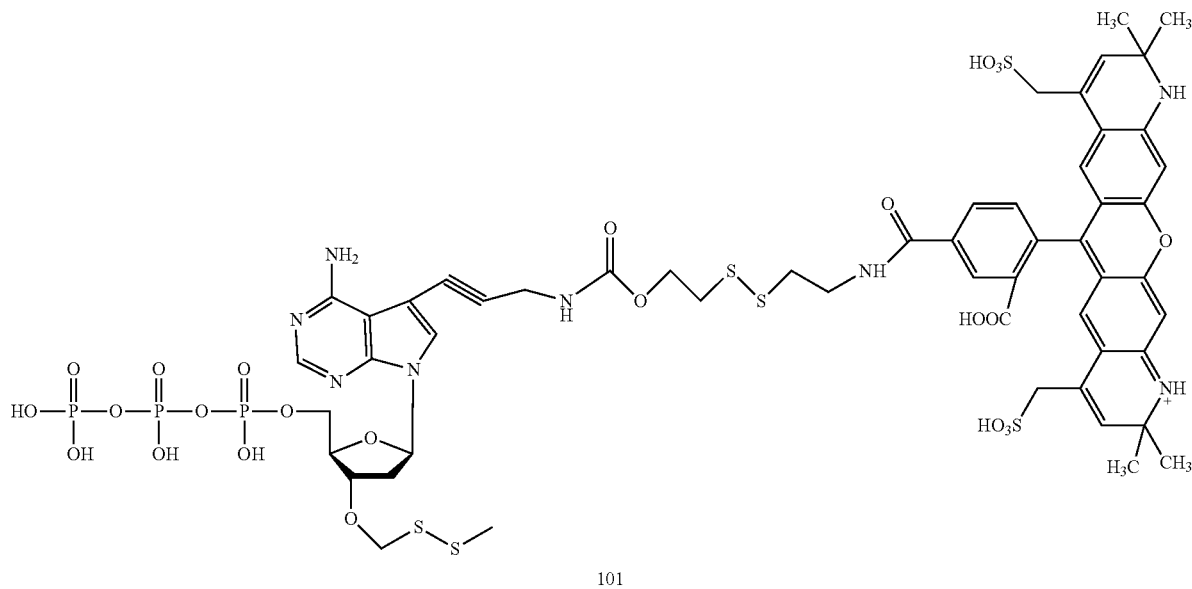

101

The chemical transformations shown in schemes 16-17 can be accomplished in many ways. For example, reagents and conditions used in scheme 16 may be: (i) 4-chloro-5-iodo-7H-pyrrolo[2.3-d]pyrimidine, NaH, ACN; (ii) NH₄OH, MeOH; (iii) N-trifluoroacetylpropargylamine, Pd(PPh₃)₄, CuI, triethylamine, DMF; (iv) tert-butyl-diphenylsilylchloride, pyridine; (v) (a) chlorotrimethylsilane, pyridine, (b) benzoyl chloride; (vi) DMSO, AcOH, acetic anhydride; (vii) (a) SO₂Cl₂, (b) potassium p-toluenethiosulfonate, (c) sodium thiomethoxide; (viii) MeOH, ammonia. Reagents and conditions used in Scheme 17 may be: (i) 10, NaHCO₃/Na₂CO₃ buffer (pH 9.2), acetonitrile; (ii) Et₃N.3HF, THF; (iii) (a) 2-chloro-1H-1,3,2-benzodioxaphosphorin-4-one, pyridine, THF, (b) tributylamine, tributylammonium pyrophosphate; (c) tert-butyl hydrogen peroxide; (iv) aqueous TFA, (v) ALEXA FLUOR® 568 NHS ester [1,10-Dihydro-2,2,10,10-tetramethyl-4,8-bis(sulfomethyl)-2H-pyrano[3,2-g:5,6-g']diquinolin-6-yl]benzenedicarboxylate-N-ethyl-N-(1-methylethyl)-2-propanamine, NaHCO₃/Na₂CO₃ buffer (pH 9.2).

For example, Schemes 18-19 depict synthetic routes that may provide some novel labeled reversible terminators.

Scheme 18

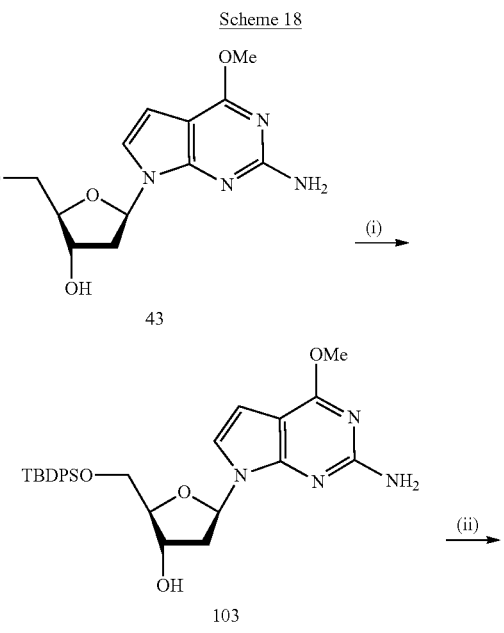

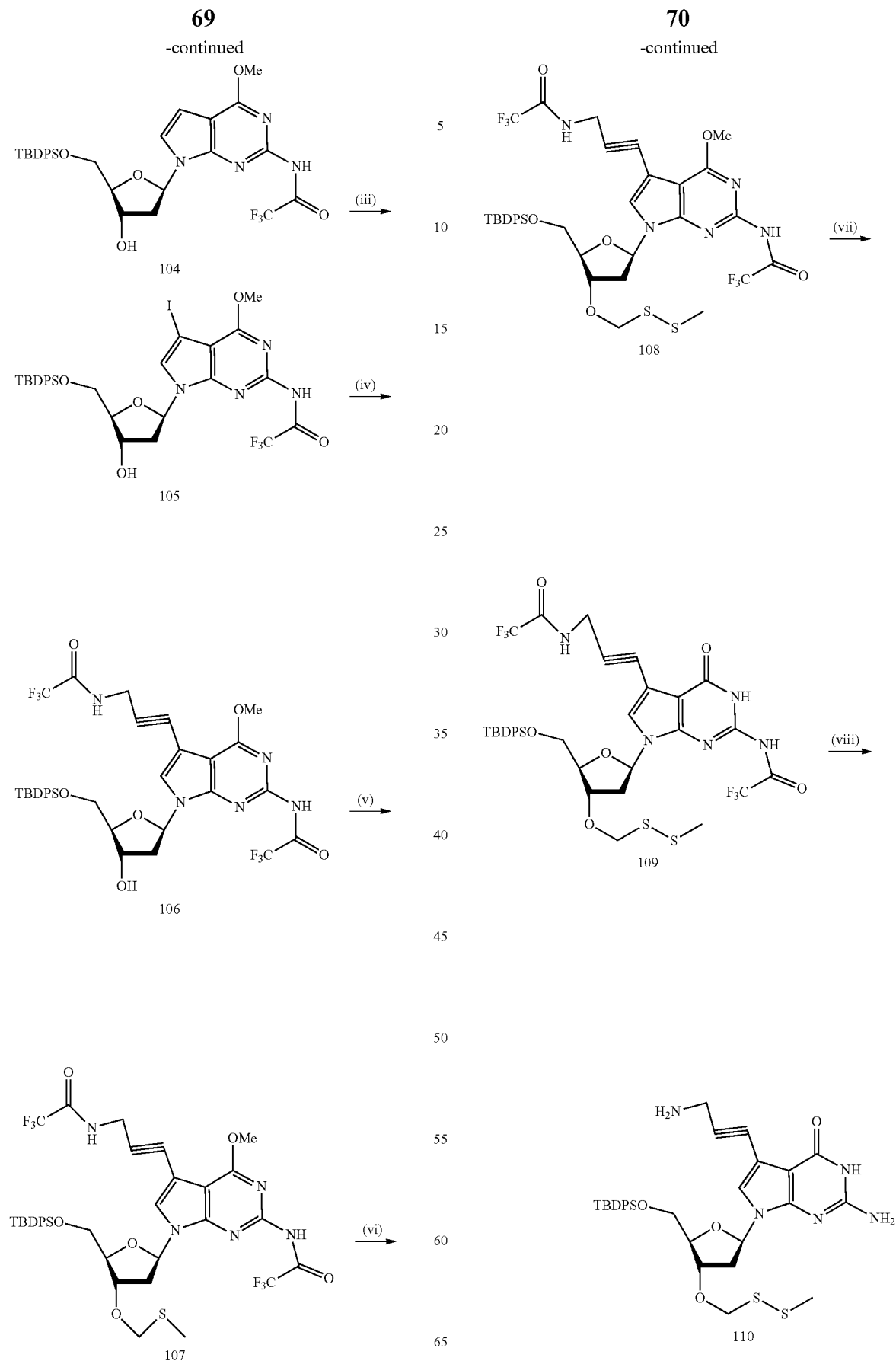

Scheme 19
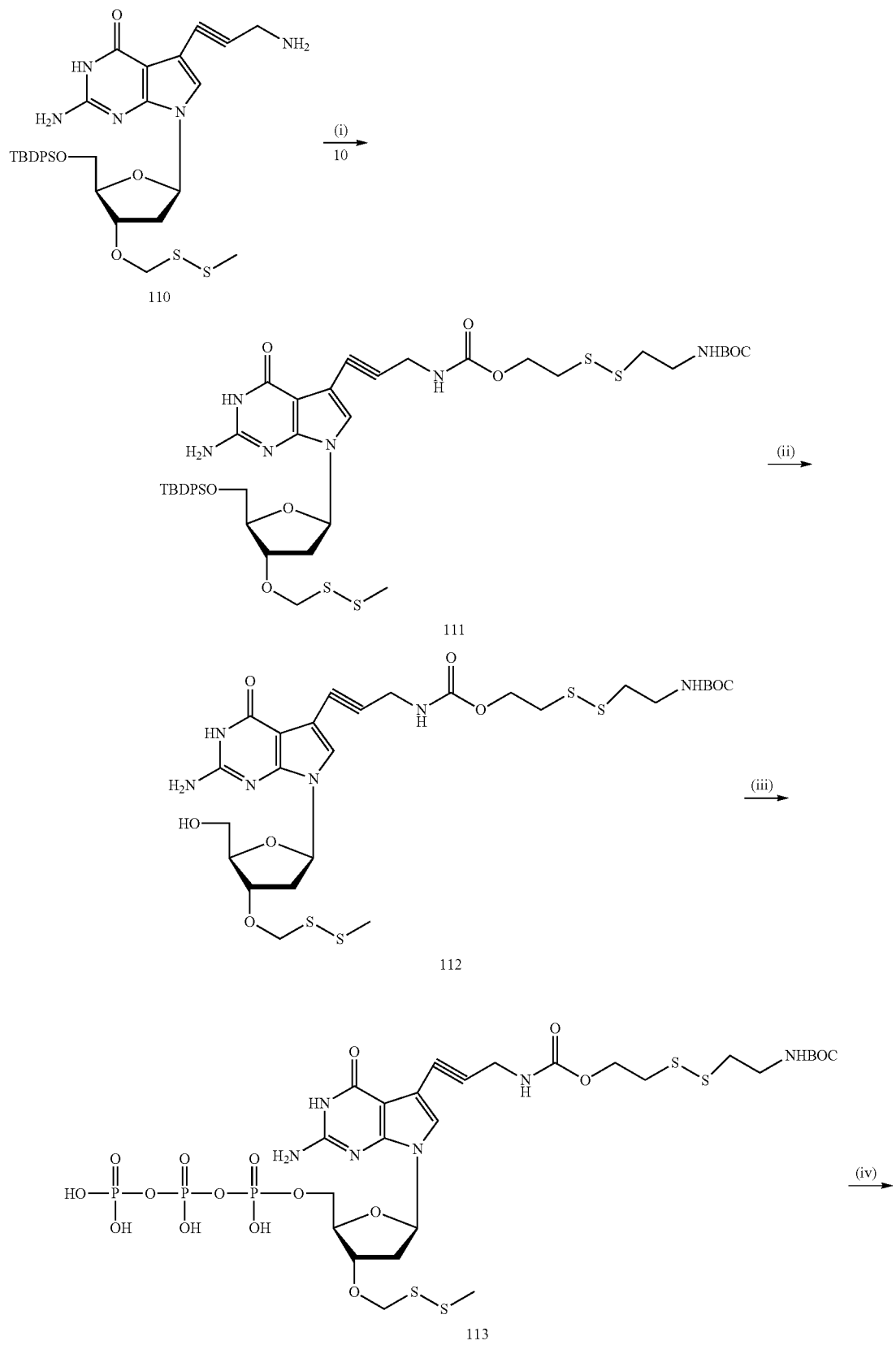

-continued

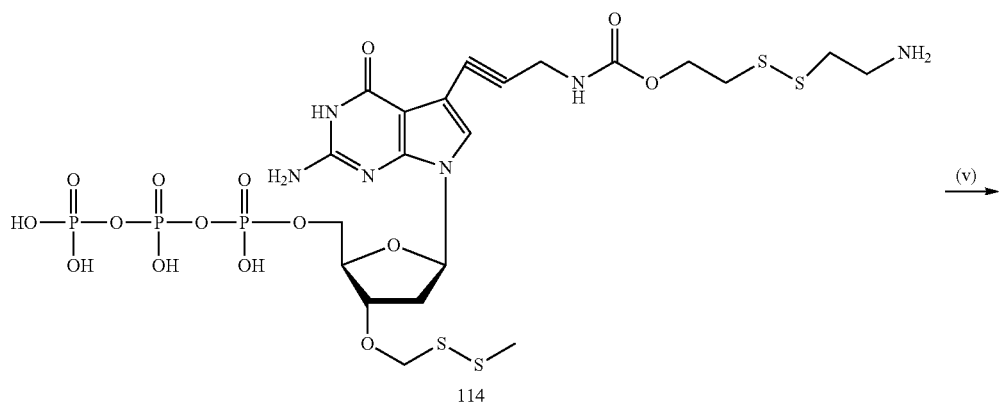

114

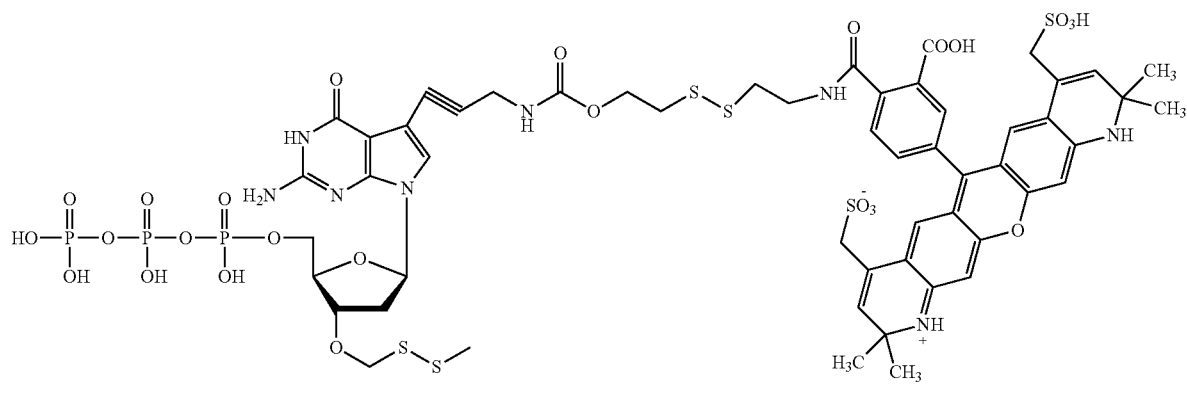

115

The chemical transformations shown in schemes 18-19 can be accomplished in many ways. For example, reagents and conditions used in scheme 18 may be: (i) tert-butyl-diphenylsilylchloride, pyridine, RT, 12 h; (ii) trifluoroacetic anhydride, pyridine, RT, 12 h; (iii) N-iodosuccinamide, DMF, 80° C., 2 h; (iv) N-trifluoroacetylpropargylamine, Pd(PPh$_3$)$_4$, CuI, triethylamine, DMF, RT, 12 h; (v) DMSO, AcOH, acetic anhydride, RT, 12 h; (vi) (a) SO$_2$Cl$_2$, 0° C., 1 h, (b) potassium p-toluenethiosulfonate, RT, 2 h, (c) sodium thiomethoxide, RT, 1.5 h; (vii) trimethylsilyliodide, DMF, 6 h; (viii) methanolic ammonia, RT, 12 h. Reagents and conditions used in Scheme 19 may be: (i) 10, NaHCO$_3$/Na$_2$CO$_3$ buffer (pH 9.2), acetonitrile; (ii) Et$_3$N.3HF, THF; (iii) (a) 2-chloro-1H-1,3,2-benzodioxaphosphorin-4-one, pyridine, THF, 1.5 h, (b) tributylamine, tributylammonium pyrophosphate, 4 h; (c) tert-butyl hydrogen peroxide, 1 h; (iv) aqueous TFA; (v) ALEXA FLUOR® 568 NHS ester [1,10-Dihydro-2,2,10,10-tetramethyl-4,8-bis(sulfomethyl)-2H-pyrano[3,2-g:5,6-g']diquinolin-6-yl]benzenedicarboxy-late-N-ethyl-N-(1-methylethyl)-2-propanamine, NaHCO$_3$/Na$_2$CO$_3$ buffer (pH 9.2).

There may be many different routes leading to the synthesis of a reversible terminator of the general formulae (II) or (III):

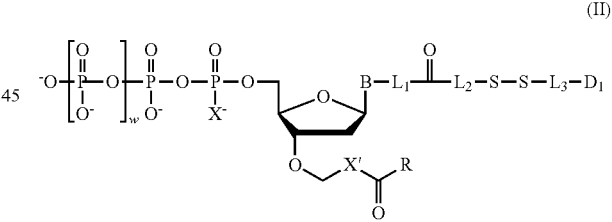
(II)

wherein w is 1-5; X is O, S, or BH$_3$; X' is O or S; w is 1, 2, 3, 4, or 5; B is a nucleotide base or an analog thereof; each of L$_1$, L$_2$ and L$_3$ is independently a linker; D$_1$ is a detectable label, R$_X$ is H or C$_{1-6}$ alkyl;

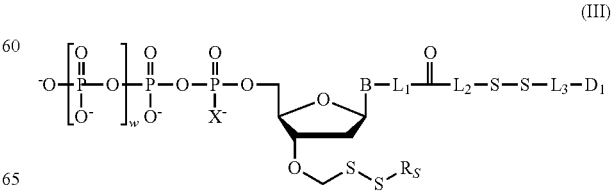
(III)

wherein w is 1-5; X is O, S, or $BH_3$; w is 1, 2, 3, 4, or 5; B is a nucleotide base or an analog thereof; each of $L_1$, $L_2$ and $L_3$ is independently a linker; D is a detectable label, $R_X$ is H or $C_{1-6}$ alkyl.

In some embodiments, for example, the bond between $L_1$ and the carbonyl group can be formed from two respective intermediates; the bond between $L_2$ and the carbonyl group can be formed from two respective intermediates; the disulfide bond between $L_1$ and $L_2$ can be formed from two respective intermediates; and $L_3$ can be formed by joining two intermediates together through a bond-formation step. Each of $L_1$, $L_2$ and $L_3$ may contain additional points of bond-making positions to connect two intermediates together in order to from the reversible terminator. Although the present disclosure only presents a few synthetic routes leading to the reversible terminator, other similar or different synthetic routes may be possible when taken into consideration of the particular structure of the targeted reversible terminator. Such synthetic methods to connect two intermediates may be used similar to what have been disclosed herein.

To prepare reversible terminators according to the present disclosure, the conversion of nucleosides to the corresponding nucleoside 5'-triphosphates may use any one of the many published protocols for carrying out this purpose. (See, for instance, Caton-Williams J, et al., "Use of a Novel 5'-Regioselective Phosphitylating Reagent for One-Pot Synthesis of Nucleoside 5'-Triphosphates from Unprotected Nucleosides," *Current Protocols in Nucleic Acid Chemistry*, 2013, 1.30.1-1.30.21; Nagata S, et al., "Improved method for the solid-phase synthesis of oligoribonucleotide 5'-triphosphates," *Chem. Pharm. Bull.*, 2012, 60(9): 1212-15; Abramova et al., "A facile and effective synthesis of dinucleotide 5' triphosphates," *Bioorg. Med. Chem.*, 15:6549-6555, 2007; Abramova et al., "Synthesis of morpholine nucleoside triphosphates," *Tet. Lett.*, 45:4361, 2004; Lebedev et al., "Preparation of oligodeoxyribonucleotide 5'-triphosphates using solid support approach," *Nucleos. Nucleot. Nucleic. Acids*, 20: 1403, 2001; Hamel et al., "Synthesis of deoxyguanosine polyphosphates and their interactions with the guanosine 5'-triphosphate requiring protein synthetic enzymes of *Escherichia coli*," *Biochemistry*, 1975, 14(23): 5055-5060; Vaghefi M., "Chemical synthesis of nucleoside 5'-triphosphates," In: Nucleoside Triphosphates and their Analogs, pp. 1-22, Taylor & Francis, 2005; Burgess et al., "Synthesis of nucleoside triphosphates," *Chem. Rev.*, 100: 2047-2059, 2000).

Reversible terminators in the present disclosure comprise an (alkyldisulfanyl)methyl group at the 3' oxygen of the sugar moiety. Reversible terminator nucleotides of this type may be useful in methodologies for determining the sequence of polynucleotides. The methodologies in which these reversible terminator nucleotides are useful may include, but are not limited to, automated Sanger sequencing, NGS methods including, but not limited to, sequencing by synthesis, and the like. Many methods of analyzing or detecting a polynucleotide may optionally employ the presently disclosed reversible terminator nucleotides. Such methods may optionally employ a solid substrate to which the template is covalently bound. The solid substrate may be a particle or microparticle or flat, solid surface of the type used in current instrumentation for sequencing of nucleic acids. (See, for example, Ruparel et al., *Proc. Natl. Acad Sci.*, 102:5932-5937, 2005; EP 1,974,057; WO 93/21340 and U.S. Pat. Nos. 5,302,509 and 5,547,839, and references cited therein). Optionally, the sequencing reaction employing the presently disclosed reversible terminator nucleotides may be performed in solution or the reaction is performed on a solid phase, such as a microarray or on a microbead, in which the DNA template is associated with a solid support. Solid supports may include, but are not limited to, plates, beads, microbeads, whiskers, fibers, combs, hybridization chips, membranes, single crystals, ceramics, and self-assembling monolayers and the like. Template polynucleic acids may be attached to the solid support by covalent binding such as by conjugation with a coupling agent or by non-covalent binding such as electrostatic interactions, hydrogen bonds or antibody-antigen coupling, or by combinations thereof. There are a wide variety of methods of attaching nucleic acids to solid supports.

Linkers

Linkers or contemplated herein are of sufficient length and stability to allow efficient hydrolysis or removal by chemical or enzymatic means. Useful linkers may be readily available and may be capable of reacting with a hydroxyl moiety (or base or nucleophile) on one end of the linker or in the middle of the linker. One end of the linker may be capable of being bound to or modified by a label group, such as D1 for a detectable label. The number of carbons or atom in a linker, optionally derivatized by other functional groups, must be of sufficient length to allow either chemical or enzymatic cleavage of the blocking group, if the linker is attached to a blocking group or if the linker is attached to the detectable label.

While precise distances or separation may be varied for different reaction systems to obtain optimal results, in some cases, a linkage that maintains the bulky label moiety at some distance away from the nucleotide may be provided, e.g., a linker of 1 to 20 nm in length, to reduce steric crowding in enzyme binding sites. Therefore, the length of the linker may be, for example, 1-50 atoms in length, or 1-40 atoms in length, or 2-35 atoms in length, or 3 to 30 atoms in length, or 5 to 25 atoms in length, or 10 to 20 atoms in length, etc.

Linkers may be comprised of any number of basic chemical starting blocks. For example, linkers may comprise linear or branched alkyl, alkenyl, or alkynyl chains, or combinations thereof, that provide a useful distance between the sugar group and the detectable label, for example, D1. For instance, amino-alkyl linkers, e.g., amino-hexyl linkers, have been used to provide label attachment to nucleotide analogs, and are generally sufficiently rigid to maintain such distances. The longest chain of such linkers may include as many as 2 atoms, 3 atoms, 4 atoms, 5 atoms, 6 atoms, 7 atoms, 8 atoms, 9 atoms, 10 atoms, or even 11-35 atoms, or even 35-50 atoms. The linear or branched linker may also contain heteroatoms other than carbon, including, but not limited to, oxygen, sulfur, phosphate, and nitrogen. A polyoxyethylene chain (also commonly referred to as polyethyleneglycol, or PEG) is a preferred linker constituent due to the hydrophilic properties associated with polyoxyethylene. Insertion of heteroatom such as nitrogen and oxygen into the linkers may affect the solubility and stability of the linkers.

In some cases, a linker may be selected from a group selected from alkylene, alkenylene, alkynylene, heteroalkylene, cycloalkylene, heteroarylalkylene, heterocycloalkylene, arylene, heteroarylene, or $[R_2-K-R_2]_n$, or combinations thereof; and each linker group may be substituted with 0-6 $R_3$; each $R_2$ is independently alkylene, alkenylene, alkynylene, heteroarylalkylene, cycloalkylene, heterocycloalkylene, arylene, or heteroarylalkylene;

K is a bond, —O—, —S—, —S(O)—, —S($O_2$)—, —C(O)—, —C(O)O—, —C(O)N($R_3$)—, or

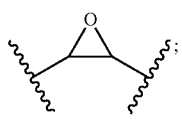

each $R_3$ is independently hydrogen, alkyl, alkenyl, alkynyl, arylalkyl, heteroalkyl, cycloalkyl, heterocycloalkyl, cycloalkylalkyl, cycloaryl, or heterocycloaryl, substituted with 0-6 $R_5$; each $R_5$ is independently halogen, alkyl, —$OR_6$, —$N(R_6)_2$, —$SR_6$, —$S(O)R_6$, —$SO_2R_6$, or —$C(O)OR_6$; each $R_6$ is independently —H, alkyl, alkenyl, alkynyl, arylalkyl, cycloalkylalkyl, or heterocycloalkyl; and n is an integer from 1-4

The linker may be rigid in nature or flexible. Rigid structures include laterally rigid chemical groups, e.g., ring structures such as aromatic compounds, multiple chemical bonds between adjacent groups, e.g., double or triple bonds, in order to prevent rotation of groups relative to each other, and the consequent flexibility that imparts to the overall linker. Thus, the degree of desired rigidity may be modified depending on the content of the linker, or the number of bonds between the individual atoms comprising the linker. Further, addition of ringed structures along the linker may impart rigidity. Ringed structures may include aromatic or non-aromatic rings. Rings may be anywhere from 3 carbons, to 4 carbons, to 5 carbons or even 6 carbons in size. Rings may also optionally include heteroatoms such as oxygen or nitrogen and also be aromatic or non-aromatic. Rings may additionally optionally be substituted by other alkyl groups and/or substituted alkyl groups.

Linkers that comprise ring or aromatic structures can include, for example aryl alkynes and aryl amides. Other examples of the linkers of the disclosure include oligopeptide linkers that also may optionally include ring structures within their structure.

For example, in some cases, polypeptide linkers may be employed that have helical or other rigid structures. Such polypeptides may be comprised of rigid monomers, which derive rigidity both from their primary structure, as well as from their helical secondary structures, or may be comprised of other amino acids or amino acid combinations or sequences that impart rigid secondary or tertiary structures, such as helices, fibrils, sheets, or the like. By way of example, polypeptide fragments of structured rigid proteins, such as fibrin, collagen, tubulin, and the like may be employed as rigid linker molecules.

All of the linkers which attach the detectable label to the base of the nucleotide comprise a disulfide moiety in the present disclosure. In addition, a second cleavable group such as a carbonate or a carbamate is placed in the vicinity of the disulfide bond between the disulfide bond and the base. The separation between the disulfide bond and the second cleavable group may be 2 or 3 atoms. In some embodiments, the separation may be an ethylene group, optionally with 1 or 2 substitutions. In other embodiments, the separation may be a propylene group, optionally with 1-3 substitutions.

Labels & Dyes

A label or detectable label, as in D1, of the present reversible terminators, may be any moiety that comprises one or more appropriate chemical substances or enzymes that directly or indirectly generate a detectable signal in a chemical, physical or enzymatic reaction. A large variety of labels are well known in the art. (See, for instance, PCT/GB2007/001770).

For instance, one class of such labels is fluorescent labels. Fluorescent labels have the advantage of coming in several different wavelengths (colors) allowing distinguishably labeling each different terminator molecule. (See, for example, Welch el al., Chem. Eur. J., 5(3):951-960, 1999). One example of such labels is dansyl-functionalized fluorescent moieties. Another example is the fluorescent cyanine-based labels Cy3 and Cy5, which can also be used in the present disclosure. (See, Zhu el al., Cytometry, 28:206-211, 1997). Labels suitable for use are also disclosed in Prober et al., Science, 238:336-341, 1987; Connell et al., BioTechniques, 5(4):342-384, 1987; Ansorge el al., Nucl. Acids Res., 15(11):4593-4602, 1987; and Smith et al., Nature, 321:674, 1986. Other commercially available fluorescent labels include, but are not limited to, fluorescein and related derivatives such as isothiocyanate derivatives, e.g. FITC and TRITC, rhodamine, including TMR, texas red and Rox, bodipy, acridine, coumarin, pyrene, benzanthracene, the cyanins, succinimidyl esters such as NHS-fluorescein, maleimide activated fluorophores such as fluorescein-5-maleimide, phosphoramidite reagents containing protected fluorescein, boron-dipyrromethene (BODIPY) dyes, and other fluorophores, e.g. 6-FAM phosphoramidite 2. All of these types of fluorescent labels may be used in combination, in mixtures and in groups, as desired and depending on the application.

Various commercially available fluorescent labels are known in the art, such as Alexa Fluor Dyes, e.g., Alexa 488, 555, 568, 660, 532, 647, and 700 (Invitrogen-Life Technologies, Inc., California, USA, available in a wide variety of wavelengths, see for instance, Panchuk, et al., J. Hist. Cyto., 47:1179-1188, 1999). Also commercially available are a large group of fluorescent labels called ATTO dyes (available from ATTO-TEC GmbH in Siegen, Germany). These fluorescent labels may be used in combinations or mixtures to provide distinguishable emission patterns for all terminator molecules used in the assay since so many different absorbance and emission spectra are commercially available.

In various exemplary embodiments, a label comprises a fluorescent dye, such as, but not limited to, a rhodamine dye, e.g., R6G, R1 10, TAMRA, and ROX, a fluorescein dye, e.g., JOE, VIC, TET, HEX, FAM, etc., a halo-fluorescein dye, a cyanine dye. e.g., CY3, CY3.5, CY5, CY5.5, etc., a BODIPY® dye, e.g., FL, 530/550, TR, TMR, etc., a dichlororhodamine dye, an energy transfer dye, e.g., BIGD YE™ v 1 dyes, BIGD YE™ v 2 dyes, BIGD YE™ v 3 dyes, etc., Lucifer dyes, e.g., Lucifer yellow, etc., CASCADE BLUE®, Oregon Green, and the like. Other exemplary dyes are provided in Haugland, Molecular Probes Handbook of Fluorescent Probes and Research Products, Ninth Ed. (2003) and the updates thereto. Non-limiting exemplary labels also include, e.g., biotin, weakly fluorescent labels (see, for instance, Yin et al., Appl Environ Microbiol., 69(7):3938, 2003; Babendure et al., Anal. Biochem., 317(1): 1, 2003; and Jankowiak et al., Chem. Res. Toxicol., 16(3):304, 2003), non-fluorescent labels, colorimetric labels, chemiluminescent labels (see, Wilson et al., Analyst, 128(5):480, 2003; Roda et al., Luminescence, 18(2):72, 2003), Raman labels, electrochemical labels, bioluminescent labels (Kitayama et al., Photochem. Photobiol., 77(3):333, 2003; Arakawa et al., Anal. Biochem., 314(2):206, 2003; and Maeda, J. Pharm. Biomed Anal., 30(6): 1725, 2003), and the like.

Multiple labels can also be used in the disclosure. For example, bi-fluorophore FRET cassettes (Tet. Letts., 46:8867-8871, 2000) are well known in the art and can be utilized in the disclosed methods. Multi-fluor dendrimeric systems (*J. Amer. Chem. Soc.,* 123:8101-8108, 2001) can also be used. Other forms of detectable labels are also available. For example, microparticles, including quantum dots (Empodocles, et al., *Nature,* 399:126-130, 1999), gold nanoparticles (Reichert et al., *Anal. Chem.,* 72:6025-6029, 2000), microbeads (Lacoste et al., *Proc. Natl. Acad Sci. USA,* 97(17):9461-9466, 2000), and tags detectable by mass spectrometry can all be used.

Multi-component labels can also be used in the disclosure. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

Thus, a "label" as presently defined is a moiety that facilitates detection of a molecule. Common labels in the context of the present disclosure include fluorescent, luminescent, light-scattering, and/or colorimetric labels. Suitable labels may also include radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. As other non-limiting examples, the label can be a luminescent label, a light-scattering label (e.g., colloidal gold particles), or an enzyme (e.g., Horse Radish Peroxidase (HRP)).

Fluorescence energy transfer (FRET) dyes may also be employed, such as DY-630/DY-675 from Dyomics GmbH of Germany, which also commercially supplies many different types of dyes including enzyme-based labels, fluorescent labels, etc. (See, for instance, Dohm et al., "Substantial biases in ultra-short read data sets from high-throughput DNA sequencing," *Nucleic Acids Res.,* 36:e105, 2008). Other donor/acceptor FRET labels include, but are not limited to:

| Donor | Acceptor | $R_0$ (Å) |
|---|---|---|
| Fluorescein | Tetramethylrhodamine | 55 |
| IAEDANS | Fluorescein | 46 |
| EDANS | Dabcyl | 33 |
| Fluorescein | Fluorescein | 44 |
| BODIPY FL | BODIPY FL | 57 |
| Fluorescein | QSY 7 and QSY 9 dyes | 61 |

(See also, Johansen, M. K., "Choosing Reporter-Quencher Pairs for Efficient Quenching Through Formation of Intramolecular Dimers," Methods in Molecular Biology, vol. 335: Fluorescent Energy Transfer Nucleic Acid Probes: Designs and Protocols, Edited by: V. V. Didenko, Humana Press Inc., Totowa, N.J.). Other dye quenchers are commercially available, including dabcyl, QSY quenchers and the like. (See also, Black Hole Quencher Dyes from Biosearch Technologies, Inc., Novato, Calif.; Iowa Black Dark Quenchers from Integrated DNA Technologies, Inc. of Coralville, Iowa; and other dye quenchers sold by Santa Cruz Biotechnology, Inc. of Dallas, Tex.).

The label and linker construct can be of a size or structure sufficient to act as a block to the incorporation of a further nucleotide onto the nucleotide of the disclosure. This permits controlled polymerization to be carried out. The block can be due to steric hindrance, or can be due to a combination of size, charge and structure.

Polymerase Enzymes used in SBS/SBE Sequencing

As already commented upon, one of the key challenges facing SBS or SBE technology is finding reversible terminator molecules capable of being incorporated by polymerase enzymes efficiently and which provide a blocking group that can be removed readily after incorporation. Thus, to achieve the presently claimed methods, polymerase enzymes must be selected which are tolerant of modifications at the 3' and 5' ends of the sugar moiety of the nucleoside analog molecule. Such tolerant polymerases are known and commercially available.

BB Preferred polymerases lack 3'-exonuclease or other editing activities. As reported elsewhere, mutant forms of 9° N-7(exo-) DNA polymerase can further improve tolerance for such modifications (WO 2005024010; WO 2006120433), while maintaining high activity and specificity. An example of a suitable polymerase is THERMINATOR™ DNA polymerase (New England Biolabs, Inc., Ipswich, Mass.), a Family B DNA polymerase, derived from *Thermococcus* species 9° N-7. The 9° N-7(exo-) DNA polymerase contains the D141A and E143A variants causing 3'-5' exonuclease deficiency. (See, Southworth et al., "Cloning of thermostable DNA polymerase from hyperthermophilic marine Archaea with emphasis on *Thermococcus* species 9° N-7 and mutations affecting 3'-5' exonuclease activity," *Proc. Natl. Acad Sci. USA,* 93(11): 5281-5285, 1996). THERMINATOR™ I DNA polymerase is 9° N-7 (exo-) that also contains the A485L variant. (See, Gardner et al., "Acyclic and dideoxy terminator preferences denote divergent sugar recognition by archaeon and Taq DNA polymerases," *Nucl. Acids Res.,* 30:605-613, 2002). THERMINATOR™ III DNA polymerase is a 9° N-7(exo-) enzyme that also holds the L408S, Y409A and P410V mutations. These latter variants exhibit improved tolerance for nucleotides that are modified on the base and 3' position. Another polymerase enzyme useful in the present methods and kits is the exo-mutant of KOD DNA polymerase, a recombinant form of *Thermococcus kodakaraensis* KOD1 DNA polymerase. (See, Nishioka et al., "Long and accurate PCR with a mixture of KOD DNA polymerase and its exonuclease deficient mutant enzyme," *J. Biotech.,* 88:141-149, 2001). The thermostable KOD polymerase is capable of amplifying target DNA up to 6 kbp with high accuracy and yield. (See, Takagi et al., "Characterization of DNA polymerase from *Pyrococcus* sp. strain KOD1 and its application to PCR," *App. Env. Microbiol.,* 63(11):4504-4510, 1997). Others are Vent (exo-), Tth Polymerase (exo-), and Pyrophage (exo-) (available from Lucigen Corp., Middletown, Wis., US). Another non-limiting exemplary DNA polymerase is the enhanced DNA polymerase, or EDP. (See, WO 2005/024010).

When sequencing using SBE, suitable DNA polymerases include, but are not limited to, the Klenow fragment of DNA polymerase I, SEQUENASE™ 1.0 and SEQUENASE™ 2.0 (U.S. Biochemical), T5 DNA polymerase, Phi29 DNA polymerase, THERMO SEQUENASE™ (Taq polymerase with the Tabor-Richardson mutation, see Tabor et al., *Proc. Natl. Acad. Sci. USA,* 92:6339-6343, 1995) and others known in the art or described herein. Modified versions of these polymerases that have improved ability to incorporate a nucleotide analog of the disclosure can also be used.

Further, it has been reported that altering the reaction conditions of polymerase enzymes can impact their promiscuity, allowing incorporation of modified bases and reversible terminator molecules. For instance, it has been reported that addition of specific metal ions, e.g., $Mn^{2+}$, to polymerase reaction buffers yield improved tolerance for modified nucleotides, although at some cost to specificity (error rate). Additional alterations in reactions may include conducting the reactions at higher or lower temperature, higher or lower pH, higher or lower ionic strength, inclusion of co-solvents or polymers in the reaction, and the like.

Random or directed mutagenesis may also be used to generate libraries of mutant polymerases derived from native species; and the libraries can be screened to select mutants with optimal characteristics, such as improved efficiency, specificity and stability, pH and temperature optimums, etc. Polymerases useful in sequencing methods are typically polymerase enzymes derived from natural sources. Polymerase enzymes can be modified to alter their specificity for modified nucleotides as described, for example, in WO 01/23411, U.S. Pat. No. 5,939,292, and WO 05/024010. Furthermore, polymerases need not be derived from biological systems.

De-Blocking: Removal of the 3' Blocking Group and the Detectable Label

After incorporation, both the 3' blocking group (i.e., (alkyldisulfanyl)methyl group) and the detectable label attached to the base group of the nucleotide via a disulfide can be removed from the reversible terminator molecules by various means including, but not limited to, chemical means. Removal of the blocking group reactivates or releases the growing polynucleotide strand, freeing it to be available for subsequent extension by the polymerase enzyme. This enables the controlled extension of the primers by a single nucleotide in a sequential manner. The reversible terminators disclosed herein are designed to allow such removal by chemical means, and, in some cases, by enzymatic means.

In one embodiment, the reducing reagents to carry out the disulfide cleavage may be DTT or 2-mercaptoethanol. In another embodiment, the reducing reagents to carry out the disulfide cleavage may be DTT. In still another embodiment, the reducing reagents to carry out the disulfide cleavage may be 2-mercaptoethanol. In one embodiment, the reducing reagents may be trialkylphosphine and triarylphosphine. In another embodiment, the reducing reagent to carry out the disulfide cleavage is trialkylphosphine. In one embodiment, the reducing reagent to carry out the disulfide cleave is tris(2-carboxyethyl)phosphine.

DTT may be used to reduce the disulfide bonds. DTT may reduce solvent-accessible disulfide bonds, for example, the disulfide bonds of the novel reversible terminators disclosed herein. The pH of the reaction may be controlled such that DTT can cleave the disulfide bond. For example, at pH above 7.

Trialkylphosphine can reduce organic disulfides to thiols in water. Since trialkylphosphines are kinetically stable in aqueous solution, selective for the reduction of the disulfide linkage, and unreactive toward many other functional groups other than disulfides, they may be reducing agents in biochemical applications, including reactions with nucleotides such as DNA and RNA molecules.

One advantage to use trialkylphosphines over triarylphosphines (e.g., $Ph_3P$) is that the former are more likely to be liquids, which can be more easily kept from exposing to air. Another advantage of using trialkylphosphines is the fact that the resulting trialkylphosphine oxide can be water soluble and thus, are readily removed from the water-insoluble products by a simple wash with aqueous solutions.

The terminology used herein is for the purpose of describing particular cases only and is not intended to be limiting. As used herein, the singular forms "a", "an" and "the" can be intended to include the plural forms as well, unless the context clearly indicates otherwise. Furthermore, to the extent that the terms "including", "includes", "having", "has", "with", or variants thereof can be used in either the detailed description and/or the claims, such terms can be intended to be inclusive in a manner similar to the term "comprising".

The term "about" or "approximately" can mean within an acceptable error range for the particular value as determined by one of ordinary skill in the art, which may depend in part on how the value is measured or determined, i.e., the limitations of the measurement system. For example, the term "about" as used herein indicates the value of a given quantity varies by +/−10% of the value, or optionally +/−5% of the value, or in some embodiments, by +/−1% of the value so described. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values may be described in the application and claims, unless otherwise stated the term "about" meaning within an acceptable error range for the particular value should be assumed. Also, where ranges and/or subranges of values are provided, the ranges and/or subranges can include the endpoints of the ranges and/or subranges.

The term "substantially" as used herein can refer to a value approaching 100% of a given value. For example, an active agent that is "substantially localized" in an organ can indicate that about 90% by weight of an active agent, salt, or metabolite can be present in an organ relative to a total amount of an active agent, salt, or metabolite. In some cases, the term can refer to an amount that can be at least about 90%, 91%, 92%, 93%, 94%, 95%, 96%, 97%, 98%, 99%, 99.9%, or 99.99% of a total amount. In some cases, the term can refer to an amount that can be about 100% of a total amount.

As used herein, nucleotides are abbreviated with 3 letters. The first letter indicates the identity of the nitrogenous base (e.g. A for adenine, G for guanine), the second letter indicates the number of phosphates (mono, di, tri), and the third letter is P, standing for phosphate. Nucleoside triphosphates that contain ribose as the sugar, ribonucleoside triphosphates, are conventionally abbreviated as NTPs, while nucleoside triphosphates containing deoxyribose as the sugar, deoxyribonucleoside triphosphates, are abbreviated as dNTPs. For example, dATP stands for deoxyribose adenine triphosphate. NTPs are the building blocks of RNA, and dNTPs are the building blocks of DNA.

The term "immobilization" as used herein generally refers to forming a covalent bond between two reactive groups. For example, polymerization of reactive groups is a form of immobilization. A Carbon to Carbon covalent bond formation is an example of immobilization.

The term "label" or "detectable label" as used herein generally refers to any moiety or property that is detectable, or allows the detection of an entity which is associated with the label. For example, a nucleotide, oligo- or polynucleotide that comprises a fluorescent label may be detectable. In some cases, a labeled oligo- or polynucleotide permits the detection of a hybridization complex, for example, after a labeled nucleotide has been incorporated by enzymatic means into the hybridization complex of a primer and a template nucleic acid. A label may be attached covalently or non-covalently to a nucleotide, oligo- or polynucleotide. In some cases, a label can, alternatively or in combination: (i) provide a detectable signal; (ii) interact with a second label to modify the detectable signal provided by the second label, e.g., FRET; (iii) stabilize hybridization, e.g., duplex formation; (iv) confer a capture function, e.g., hydrophobic affinity, antibody/antigen, ionic complexation, or (v) change a physical property, such as electrophoretic mobility, hydrophobicity, hydrophilicity, solubility, or chromatographic behavior. Labels may vary widely in their structures and their mechanisms of action. Examples of labels may include, but are not limited to, fluorescent labels, non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. Fluorescent labels may include dyes of the fluorescein family, dyes of the rhodamine family, dyes of the cyanine family, or a coumarine, an oxazine, a boradiazaindacene or any derivative thereof. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), Texas Red is commercially available from, e.g., Thermo Fisher Scientific, Inc. (Grand Island, N.Y., USA). Dyes of the cyanine family include, e.g., CY2, CY3, CY5, CY5.5 and CY7, and are commercially available from, e.g., GE Healthcare Life Sciences (Piscataway, N.J., USA).

The term "different detectable label" or "differently labeled" as used herein generally refers to the detectable label being a different chemical entity or being differentiated among the different bases to which the labels are attached to.

As used herein, the solid substrate used can be biological, non-biological, organic, inorganic, or a combination of any of these. The substrate can exist as one or more particles, strands, precipitates, gels, sheets, tubing, spheres, containers, capillaries, pads, slices, films, plates, slides, or semiconductor integrated chips, for example. The solid substrate can be flat or can take on alternative surface configurations. For example, the solid substrate can contain raised or depressed regions on which synthesis or deposition takes place. In some examples, the solid substrate can be chosen to provide appropriate light-absorbing characteristics. For example, the substrate can be a polymerized Langmuir Blodgett film, functionalized glass (e.g., controlled pore glass), silica, titanium oxide, aluminum oxide, indium tin oxide (ITO), Si, Ge, GaAs, GaP, $SiO_2$, $SiN_4$, modified silicon, the top dielectric layer of a semiconductor integrated circuit (IC) chip, or any one of a variety of gels or polymers such as (poly)tetrafluoroethylene, (poly)vinylidenedifluoride, polystyrene, polycarbonate, polydimethylsiloxane (PDMS), polymethylmethacrylate (PMMA), polycyclicolefins, or combinations thereof.

Solid substrates can comprise polymer coatings or gels, such as a polyacrylamide gel or a PDMS gel. Gels and coatings can additionally comprise components to modify their physicochemical properties, for example, hydrophobicity. For example, a polyacrylamide gel or coating can comprise modified acrylamide monomers in its polymer structure such as ethoxylated acrylamide monomers, phosphorylcholine acrylamide monomers, betaine acrylamide monomers, and combinations thereof.

The term "hydroxyl protective group" as used herein generally refers to any group which forms a derivative of the hydroxyl group that is stable to the projected reactions wherein said hydroxyl protective group subsequently optionally can be selectively removed. Said hydroxyl derivative can be obtained by selective reaction of a hydroxyl protecting agent with a hydroxyl group.

The term "complementary" as used herein generally refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "polynucleotide sequence" or "nucleotide sequence" as used herein generally refers to a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

A "linker group" or a "linker" as used herein generally refers to a cleavable linker as described in this disclosure or a group selected from alkylene, alkenylene, alkynylene, heteroalkylene, cycloalkylene, heteroarylalkylene, heterocycloalkylene, arylene, heteroarylene, or $[R_2—K—R_2]_n$, or combinations thereof; and each linker group may be substituted with 0-6 $R_3$; each $R_2$ is independently alkylene, alkenylene, alkynylene, heteroarylalkylene, cycloalkylene, heterocycloalkylene, arylene, or heteroarylalkylene; K is a bond, —O—, —S—, —S(O)—, —S(O$_2$)—, —C(O)—, —C(O)O—, —C(O)N(R$_3$)—, or

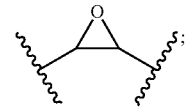 [SMILES: *C1OC1*]

each $R_3$ is independently hydrogen, alkyl, alkenyl, alkynyl, arylalkyl, heteroalkyl, cycloalkyl, heterocycloalkyl, cycloalkylalkyl, cycloaryl, or heterocycloaryl, substituted with 0-6 $R_5$; each $R_5$ is independently halogen, alkyl, —OR$_6$, —N(R$_6$)$_2$, —SR$_6$, —S(O)R$_5$, —SO$_2$R$_6$, or —C(O)OR$_6$; each $R_6$ is independently —H, alkyl, alkenyl, alkynyl, arylalkyl, cycloalkylalkyl, or heterocycloalkyl; and n is an integer from 1-4.

A "sugar moiety" as used herein generally refers to both ribose and deoxyribose and their derivatives/analogs.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York), as well as in Ausubel, infra.

The term "polynucleotide" (and the equivalent term "nucleic acid") encompasses any physical string of monomer units that can be corresponded to a string of nucleotides, including a polymer of nucleotides, e.g., a typical DNA or RNA polymer, peptide nucleic acids (PNAs), modified oligonucleotides, e.g., oligonucleotides comprising nucleotides that are not typical to biological RNA or DNA, such as 2'-O-methylated oligonucleotides, and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

The term "oligonucleotide" as used herein generally refers to a nucleotide chain. In some cases, an oligonucleotide is less than 200 residues long, e.g., between 15 and 100 nucleotides long. The oligonucleotide can comprise at least or about 1, 2, 3, 4, 5, 6, 7, 8, 9, 10, 15, 20, 25, 30, 35, 40, 45, or 50 bases. The oligonucleotides can be from about 3 to about 5 bases, from about 1 to about 50 bases, from about 8 to about 12 bases, from about 15 to about 25 bases, from about 25 to about 35 bases, from about 35 to about 45 bases, or from about 45 to about 55 bases. The oligonucleotide (also referred to as "oligo") can be any type of oligonucleotide (e.g., a primer). Oligonucleotides can comprise natural nucleotides, non-natural nucleotides, or combinations thereof.

The term "analog" in the context of nucleic acid analog is meant to denote any of a number of known nucleic acid analogs such as, but not limited to, LNA, PNA, etc. Further, a "nucleoside triphosphate analog" may contain 3-7 phosphate groups, wherein one of the oxygen (—O') on the phosphate may be replaced with sulfur (—S') or borane (—BH$_3^-$). Still further, a "nucleoside triphosphate analog" may contain a base which is an analog of adenine (A), guanine (G), thymine (T), cytosine (C) and uracil (U). For example, the bases are included:

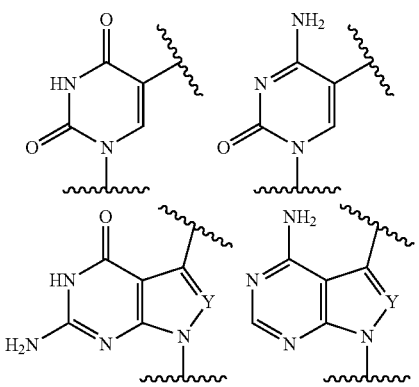

wherein Y is CH or N. One nitrogen atom of the purines and pyrimidines base, or analogs thereof, is connected to the ribose or deoxyribose C-1 position. As shown above, one carbon atom of the purines and pyrimidines base, or analogs thereof, is connected to a linker to a label.

The term "aromatic" used in the present application means an aromatic group which has at least one ring having a conjugated pi electron system, i.e., aromatic carbon molecules having 4n+2 delocalized electrons, according to Hückel's rule, and includes both carbocyclic aryl, e.g., phenyl, and heterocyclic aryl groups, e.g., pyridine. The term includes monocyclic or fused-ring polycyclic, i.e., rings which share adjacent pairs of carbon atoms, groups.

The term "heterocyclic nucleic acid base" used herein means the nitrogenous bases of DNA or RNA. These bases can be divided into two classes: purines and pyrimidines. The former includes guanine and adenine and the latter includes cytosine, thymine, and uracil.

The term "aromatic" when used in the context of "aromatic solvent" as used in the present disclosure means any of the known and/or commercially available aromatic solvents, such as, but not limited to, toluene, benzene, xylenes, any of the Kesols, and/or GaroSOLs, and derivatives and mixtures thereof.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated, i.e. $C_1$-$C_{10}$ means one to ten carbon atoms in a chain. Non-limiting examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl."

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group may have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—, —S(O)—CH$_2$, —CH$_2$—CH$_2$—S(O)$_2$—CH$_3$, —CHCH—O—CH$_3$, —Si(CH$_3$)$_3$, —CH$_2$—CHN—OCH$_3$, and —CHCH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini, e.g., alkyleneoxy, alkylenedioxy, alkyleneamino, alkylenediamino, and the like. Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl," by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring, such as those that follow Hückel's rule (4n+2, where n is any integer), or multiple rings (preferably from 1 to 5 rings), which are fused together or linked covalently and including those which obey Clar's Rule. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms, e.g., aryloxy, arylthioxy, arylalkyl, includes both aryl and heteroaryl rings as defined above. Thus, the term "arylalkyl" is meant to include those radicals in which an aryl group is attached to an alkyl group, e.g., benzyl, phenethyl, pyridylmethyl and the like, including those alkyl groups in which a carbon atom, e.g., a methylene group, has been replaced by, for example, an oxygen atom, e.g., phenoxymethyl, 2-pyridyloxymethyl, 3-(1-naphthyloxy)propyl, and the like.

Each of the above terms, e.g., "alkyl," "heteroalkyl," "aryl" and "heteroaryl," is meant to include both substituted and unsubstituted forms of the indicated radical. Preferred substituents for each type of radical are provided below.

Substituents for the alkyl and heteroalkyl radicals, including those groups often referred to as alkylene, alkenyl, heteroalkylene, heteroalkenyl, alkynyl, cycloalkyl, heterocycloalkyl, cycloalkenyl, and heterocycloalkenyl, are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR', —NR—C(NR'R")=NR'", —S(O)R', —S(O)$_2$R', —S(O)$_2$NR'R", —NRSO$_2$R', —CN and —NO$_2$ in a number ranging from zero to (2M'+1), where M' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, the term "alkyl" is meant to include groups including carbon atoms bound to groups other than hydrogen groups, such as haloalkyl, e.g., —CF$_3$ and —CH$_2$CF$_3$) and acyl, e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR, —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present. In the schemes that follow, the symbol X represents "R" as described above.

Unless otherwise noted, the term "catalytic amount," as used herein, includes that amount of the reactant that is sufficient for a reaction of the process of the disclosure to occur. Accordingly, the quantity that constitutes a catalytic amount is any quantity that serves to allow or to increase the rate of reaction, with larger quantities typically providing a greater increase. The quantity used in any particular application may be determined in large part by the individual needs of the manufacturing facility. Factors which enter into such a determination include the catalyst cost, recovery costs, desired reaction time, and system capacity. An amount of reactant may be used in the range from about 0.001 to about 0.5 equivalents, from about 0.001 to about 0.25 equivalents, from about 0.01 to about 0.25 equivalents, from about 0.001 to about 0.1, from about 0.01 to about 0.1 equivalents, including about 0.005, about 0.05 or about 0.08 equivalents of the reactant/substrate, or in the range from about 0.001 to about 1 equivalents, from about 0.001 to about 0.5 equivalents, from about 0.001 to about 0.25 equivalents, from about 0.001 to about 0.1 equivalents, from about 0.01 to about 0.5 equivalents or from about 0.05 to about 0.1 equivalents, including about 0.005, about 0.02 or about 0.04 equivalents.

Unless otherwise noted, the term "cleavable chemical group," as used herein, includes chemical group that caps the —OH group at the 3'-position of the ribose or deoxyribose in the nucleotide analogue. The cleavable chemical group may be any chemical group that 1) is stable during the polymerase reaction, 2) does not interfere with the recognition of the nucleotide analogue by polymerase as a substrate, and 3) is cleavable by a basic reagent.

Applicants are aware that there are many conventions and systems by which organic compounds may be named and otherwise described, including common names as well as systems, such as the IUPAC system.

Abbreviations

Abbreviations used throughout the present application have the meanings provided below. The meanings provided below are not meant to be limiting, but are meant to also encompass any equivalent common or systematic names understood by one of skill in the art. The meaning commonly understood by one of skill in the art should be ascribed to any other abbreviated names not listed below.

$I_2$=iodine
TBDMS=tert-butyldimethylsilyl
TBDPS=tert-butyldiphenylsilyl
BOC=tert-butyloxycarbonyl
Pyr=pyridine base
THF=tetrahydrofuran
TsOH=p-toluene sulfonic acid
DCA=dichloroacetic acid
$Bu_3N$=tributyl amine
DMF=dimethylformamide
Py=pyridine
TEAB=triethylammonium bicarbonate
DMTO=4,4'-dimethoxytriphenylmethoxy
CEO=2-cyanoethoxy
TIPSCl=triisopropylsilyl ether chloride
Et=ethyl
EtOAc=ethyl acetate
Ph=phenyl
$(PhO)_2P(O)Cl$=diphenylphosphoryl chloride
CEO-P(NiPr$_2$)$_2$=O-(2-cyanoethyl)-N,N,N,N-tetraisopropylphosphorodiamidite
$iPr_2NH$=diisopropylamine
DBU=1,8-diazabicycloundec-7-ene
FMOC=fluorenylmethyloxycarbonyl
TCEP=(tris(2-carboxyethyl)phosphine)
CDI=1,1'-carbonyldiimidazole
RT=room temperature
MeOH=methanol
TBA=tert-butyl alcohol or 2-methyl-2-propanol
TEA=triethanolamine
TFP=tetrafluoropropanol or 2,2,3,3-tetrafluoro-1-propanol
BSA=bovine serum albumin
DTT=dithiothreitol
ACN=acetonitrile
NaOH=sodium hydroxide
IE HPLC=ion-exchange high performance liquid chromatography
TLC=thin-layer chromatography
TCEP=tris(2-carboxyethyl)phosphine Synthetic Methods The size and scale of the synthetic methods may vary depending on the desired amount of end product. It is understood that while specific reactants and amounts are provided in the Examples, one of skill in the art knows other alternative and equally feasible sets of reactants that may also yield the same compounds. Thus, where general oxidizers, reducers, solvents of various nature (aprotic, apolar, polar, etc.) are utilized, equivalents may be contemplated for use in the present methods.

For instance, in all instances, where a drying agent is used, contemplated drying agents include all those reported in the literature and known to one of skill, such as, but not limited to, magnesium sulfate, sodium sulfate, calcium sulfate, calcium chloride, potassium chloride, potassium hydroxide, sulfuric acid, quicklime, phosphorous pentoxide, potassium carbonate, sodium, silica gel, aluminum oxide, calcium hydride, lithium aluminum hydride (LAH), potassium hydroxide, and the like. (See, Burfield et al., "Desiccant Efficiency in Solvent Drying. A Reappraisal by Application of a Novel Method for Solvent Water Assay," *J. Org. Chem.*, 42(18):3060-3065, 1977). The amount of drying agent to add in each work up may be optimized by one of skill in the art and is not particularly limited. Further, although general guidance is provided for work-up of the intermediates in each step, it is generally understood by one of skill that other optional solvents and reagents may be equally substituted during the work-up steps. However, in some exceptional instances, it was found the very specific work-up conditions are required to maintain an unstable intermediate. Those instances are indicated below in the steps in which they occur.

Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6$^{th}$ Ed., University Science Books, Sausalito, Calif., 1998, Ann B. McGuire, Ed., pp. 45-59). Though certain organic co-solvents and quenching agents may be indicated in the steps described below, other equivalent organic solvents and quenching agents known to one of skill may be employed equally as well and are fully contemplated herein. Further, most of the work-ups in most steps may be further altered according to preference and desired end use or end product. Drying and evaporation, routine steps at the organic synthetic chemist bench, need not be employed and may be considered in all steps to be optional. The number of extractions with organic solvent may be as many as one, two, three, four, five, or ten or more, depending on the desired result and scale of reaction. Except where specifically noted, the volume, amount of quenching agent, and volume of organic solvents used in the work-up may be varied depending on specific reaction conditions and optimized to yield the best results.

Additionally, where inert gas or noble gas is indicated, any inert gas commonly used in the art may be substituted for the indicated inert gas, such as argon, nitrogen, helium, neon, etc.

A number of patents and publications are cited herein in order to more fully describe and disclose the present methods, compounds, compositions and kits, and the state of the art to which they pertain. The references, publications, patents, books, manuals and other materials cited herein to illuminate the background, known methods, and in particular, to provide additional details with respect to the practice of the present methods, compositions and/or kits, are all incorporated herein by reference in their entirety for all purposes, to the same extent as if each individual reference was specifically and individually indicated to be incorporated by reference.

Examples

It is understood that the examples and embodiments described herein are for illustrative purposes and that various modifications or changes in light thereof may be suggested to persons skilled in the art and are to be included within the spirit and purview of this application and scope of the claims. Accordingly, the following examples are offered to illustrate, but not to limit, the claimed invention.

The following examples describe the detail synthetic steps shown in Schemes 2-4. Specifically, reagents and conditions used in Scheme 2 are: (i) N-trifluoroacetylpropargylamine, Pd (PPh$_3$)$_4$, CuI, triethylamine, DMF, room temperature (RT), 12 h; (ii) tert-butyldiphenylsilylchloride, pyridine, RT, 6 h; (iii) (a) NH$_4$OH, MeOH, 55° C. 3 h.; (b) di-tert-butyl dicarbonate (Boc$_2$O), triethylamine, in CH$_2$Cl$_2$ at room temperature, and (c) DMSO, AcOH, acetic anhydride, RT, 12 h; (iv) SO$_2$Cl$_2$, 0° C. 1 h; v) potassium salt of acetate or potassium salt of thioacetate, 18-crown-6, DMF, 4 h.

Reagents and conditions used in Scheme 3 are: (i) 2-mercaptoethanol, pyridine, anhydrous MeOH, RT, 12 h; (ii) A-BOC-cysteamine, pyridine, MeOH, RT, 12 h; (iii) 4-nitrophenylchloroformate, Et$_3$N, MeCN.

Reagents and conditions used in Scheme 4 are: (i) aqueous TFA; (ii) 10, NaHCO$_3$/Na$_2$CO$_3$ buffer (pH 9.2), acetonitrile (iii) Et$_3$N*3HF, THF, 55° C. 4 h; (iv) (a) 2-chloro-1H-1,3,2-benzodioxaphosphorin-4-one, pyridine, THF, 1.5 h, (b) tributylamine, tributylammonium pyrophosphate, 4 h; (c) tert-butyl hydrogen peroxide, 1 h; (v) aqueous TFA; (vi) fluorescent label-containing succinimidyl ester in DMSO, NaHCO$_3$/Na$_2$CO$_3$ buffer (pH 9.2).

Synthesis of 2,2,2-trifluoro-N-(3-(1-((2R,4S,5R)-4-hydroxy-5-(hydroxymethyl)tetrahydrofuran-2-yl)-2,4-dioxo-1,2,3,4-tetrahydropyrimidin-5-yl)prop-2-yn-1-yl)acetamide (2). To a solution of 5-iodouridine 1 (5.0 g, 14.1 mmol) in anhydrous DMF (40 mL), CuI (0.20 g. 1.05 mmol) and Pd(PPh$_3$)$_4$ (0.41 g, 0.035 mmol) were added under nitrogen. After stirring for 10 min. triethylamine (4.0 mL, 28.6 mmol) and 2,2,2-trifluoro-A-(prop-2-yn-1-yl)acetamide (5.4 g, 35.7 mmol) were added and the reaction mixture was stirred overnight at room temperature. The volatiles were removed under vacuum and the residue was purified by flash chromatography on silica gel [MeOH in EtOAc from 0% to 15%)] to afford the product as a yellow solid 4.1 g (76%). 1H-NMR (DMSO-d6) 511.68, (br s, 1H, NH), 10.02 (s, 1H, NH), 7.94 (s, 1H, H-6), 6.11 (t, J=7.2 Hz, 1H, H-1'), 5.29 (d, J=0.4 Hz, 1H, OH), 4.21 (m, 3H, H-3', NCH$_2$), 3.71-3.83 (m, 3H, CH$_2$-5', H-4'), 2.15-2.19 (m, 1H, H-2'), 2.03-2.08 (m, 1H, H-2'), Mass Calcd. for C$_{14}$H$_{14}$F$_3$N$_3$O$_6$ (M+Na), 400, Found 40.

Synthesis of N-(3-(1-((2R,4S,5R)-5-(((tert-butyldiphenylsilyl)oxy)methyl)-4-hydroxytetrahydrofuran-2-yl)-2,4-dioxo-1,2,3,4-tetrahydropyrimidin-5-yl)prop-2-yn-1-yl)-2,2,2-trifluoroacetamide (3). To a cooled (0° C.) solution of 2 (2.5 g, 6.61 mmol) in anhydrous pyridine (50 mL), tert-butyldiphenylsilyl chloride (2.1 g, 7.63 mmol) was added slowly under N$_2$ and the reaction mixture was further stirred at room temp overnight at room temp. The volatiles were removed under vacuum and the residue was purified by flash chromatography on silica gel (EA in hexanes from 75% to 100%) to afford desired product as white solid (2.82 g, 71%). 1H-NMR (DMSO-d6) δ 11.71 (br S, 1H, NH), 9.98 (s, 1H, NH), 8.60 (s, 1H, OH), 8.14 (s, 1H, H-6), 7.62-7.65 (m, 4H, Ar—H), 6.12 (t, J=6.9 Hz, 1H, H-1'), 5.32 (d=4.4 Hz, 1H, OH), 4.23-4.27 (m, 1H, H-3'), 4.09 (d, J=4.8 Hz, 2H, NCH$_2$), 3.83-3.88 (m, 2H, H-5'), 3.68-3.74 (m, 1H, H-4'), 2.18 (m, 2H, H-2'), 1.00 (s, 9H, C(CH$_3$)$_3$); Mass Calcd. for C$_{30}$H$_{32}$F$_3$N$_3$O$_6$Si (M+Na), 638.6 found 638.

Synthesis of N-(3-(1-((2R,4S,5R)-5-(((tert-butyldiphenylsilyl)oxy)methyl)-4-((methylthio)methoxy)tetrahydrofuran-2-yl)-2,4-dioxo-1,2,3,4-tetrahydropyrimidin-5-yl)prop-2-yn-1-yl)-2,2,2-trifluoroacetamide (4). Compound 3 (2.0 g, 3.24 mmol) in DMSO (5.2 mL), acetic acid (1.1 mL) and acetic anhydride (3.5 mL) were added subsequently under N$_2$, and the reaction was stirred overnight at room temperature. The reaction mixture was concentrated under vacuum and the residue was diluted with ethyl acetate (EA) and poured in satd. NaHCO$_3$ solution (150 mL) and stirred for 1 h. The aqueous layer was extracted with EA. The combined organic layers were dried (MgSO$_4$), filtered and concentrated to afford an oil. The oil was purified by flash column chromatography over silica gel and eluted with 40-80% EA in hexanes to afford the product 4 as a white solid (1.22 g, 55%). 1H-NMR (DMSO-d6) δ 8.60 (br s, 2H, NH), 8.17 (s, 1H, H-6), 7.68-7.71 (m, 4H, Ar—H), 7.41-7.50 (m, 6H, Ar-if), 6.30 (dd, J=5.6 Hz and 2.8 Hz, 1H, H-1'), 4.6-4.64 (m, 2H, OCH$_2$S), 4.13-4.15 (m, 1H, H-3'), 4.06-4.08 (m, 3H, H-5' and NCH$_2$), 3.98-4.02 (m, 1H, H-5'), 3.79-3.82 (m, 1H, H-4'), 2.54-2.59 (m, 1H, H-2'), 2.44-2.48 (M, 1H, H-2'), Mass calcd. for C$_{32}$H$_{36}$F$_3$N$_3$O$_6$SSi, 675.8, Found (M+H), 676.

Synthesis of Compound 6. A solution of Compound 4 and cyclohexene in anhydrous dichloromethane is cooled to 0° C., and sulfuryl chloride (1M solution in DCM) is added dropwise under N$_2$. After stirring for 1 h, volatiles are removed under vacuum and the residue is dissolved in anhydrous DMF and potassium acetate or potassium thioacetate is added and stirred for 3 h. The reaction is quenched with dichloromethane and the organic layer is washed with saturated aq. brine solution. The organic layer is dried over anhydrous MgSO$_4$ and concentrated under vacuum. The residue is chromatographed over silica gel to provide Compound 6.

2-(Pyridin-2-yldisulfaneyl)ethan-1-ol (8). 2-Mercaptoethanol (3.9 g, 49.9 mmol) was added to a solution of 1,2-di(pyridin-2-yl)disulfane 7 (10 g, 45.4 mmol) in pyridine/Methanol (3:200 mL) and mixture was stirred overnight. The mixture was evaporated to dryness and the residue was purified by flash chromatography on silica gel. The residue was eluted with 30-50% ethyl acetate in hexanes to afford the product 8 as a colorless oil (4.5 g, 53%). 1H-NMR (CDCl$_3$) δ 8.51 (d, J=4.0 Hz, 1H, Ar—H), 7.57-7.62 (m, 1H—Ar—H), 7.40-7.62 (m, 1H, Ar—H), 7.15-7.28 (m, 1H, Ar—H), 5.84 (br s, 1H, OH), 3.81 (t, J=5.2 Hz, 2H, OCH$_2$), 2.96 (t, J=5.2 Hz, SCH$_2$), Mass calcd. for C$_7$H$_9$NOS$_2$ 187, Found (M+H) 188.

tert-Butyl (2-((2-hydroxyethyl)disulfaneyl)ethyl)carbamate (9). To a solution of Compound 8 (0.9 g, 4.8 mmol) in methanol/pyridine (40/1 mL) was added BOC-cysteamine (2.1 g, 11.8 mmol) and the mixture was stirred overnight. The reaction was concentrated and the residue was purified by flash chromatography on silica gel. The product 9 was obtained with 40-60% ethanol in hexanes gradient as a colorless oil (1.04 g, 86%). 1H-NMR (CDCl3) δ 4.89 (br s, 1H, OH), 3.88-3.91 (t, J=5.6 Hz, 2H, OCH$_2$), 3.46-3.48 (m, 2H, NCH$_2$), 2.88-2.91 (t, J=6.0H$_z$, 2H, SCH$_2$), 2.80-2.83 (t, J=6.8 Hz, 2H, SCH$_2$), 1.45 (s, 9H, C(CH$_3$)$_3$). Mass calcd for C$_9$H$_{19}$NO$_3$S$_2$, 253.0, found (M+Na) 276.

tert-Butyl (2-((2-(((4-nitrophenoxy)carbonyl)oxy)ethyl)disulfaneyl)ethyl)-carbamate (10). To a cooled (4° C.) of Compound 9 (0.80 g, 3.16 mmol) in anhydrous acetonitrile, triethyl amine (540 µL, 3.82 mmol) and a solution of 4-nitrophenylcarbonate (0.75 g, 3.72 mmol) in acetonitrile was added slowly during 10 minutes under nitrogen. The reaction was stirred further overnight at room temperature. After removing the volatiles, the crude residue was purified by flash chromatography on silica gel. The product 10 was eluted as a white crystalline solid (1.05 g, 75%). 1H-NMR (CDCl$_3$) δ 8.30 (d, J=9.2 Hz, 2H, Ar—H), 7.41 (d, J=9.2 Hz, 2H, Ar—H), 4.55-4.58 (t, J=6.8 Hz, 2H, OCH$_2$), 3.48-3.49 (m, 2H, NCH$_2$), 3.02-3.06 (t, J=6.8 Hz, 2H, SCH$_2$), 2.84-2.87 (t, J=6.0 Hz, 2H, SCH$_2$), 1.46 (s, 9H, C(CH$_3$)$_3$), Mass calcd for C$_{16}$H$_{22}$N$_2$O$_7$S$_2$(M+Na) 441, found, 441.

Synthesis Compound 11. Aqueous TFA is used to remove the BOC group on the primary amine 6 to afford intermediate 11.

Synthesis of Compound 12. To a solution of intermediate 11 in acetonitrile, a solution of 10 in acetonitrile is added and the reaction is stirred overnight. Reaction is diluted with ethyl acetate, and washed with brine. Organic layer is separated, dried over anhydrous MgSO$_4$ and concentrated. The residue is purified by flash chromatography on silica gel to give the intermediate 12.

Synthesis of Compound 13. To a solution of 12 in anhydrous THF is added a solution of triethylamine trihydrofluoride and the mixture is heated for 3 h at 55° C. The volatiles are removed and the residue is purified by flash chromatography on silica gel to afford intermediate 13.

Synthesis of Compound 14. To a solution of 13 in anhydrous THF and anhydrous pyridine (v/v=1:1), a solution of 2-chloro-4H-1,3,2-benzodioxaphosphorin-4-one dissolved in THF is added under nitrogen and stirred for 1.5 h. Tributylamine and tributyl-ammonium pyrophosphate are added subsequently and stirred further for 3 h. tert-Butyl hydroperoxide solution is added to reaction and stirred further for 1 h. The reaction is then quenched with water and left overnight. The crude product is purified by ion exchange HPLC using Dionex DNA Pac column (9×250 mm) and 50 mM TRIS as buffer A and 50 mM Tris and 800 mM ammonium chloride as buffer B with a gradient of 0-40% B in 30 min to give compound 14.

Synthesis of Compound 15. Aqueous trifluoroacetic acid solution is added to a solution of 14 in water and stirred for 4 h. The desired product is isolated by reverse phase HPLC using Hamilton PRP-column (21.2×250 mm) and 50 mm triethylammonium bicarbonate as buffer A and acetonitrile as buffer B using a gradient of 0-40% B in 30 minutes.

Synthesis of fluorescein labeled terminator 16: To a solution of 15 in water, a solution of fluorescent label-containing succinimidyl ester in DMSO is added. The pH of the reaction mixture is maintained at about 8.3. The reaction is stirred overnight. The crude product is purified by reverse phase HPLC using 50 mM triethyl ammonium bicarbonate as buffer A and acetonitrile as buffer B using a gradient of 0-40% B in 30 min to afform reversible terminator 16.

The following examples describe the detail synthetic steps shown in Schemes 12-13. Specifically, reagents and conditions used in Scheme 12 are: (i) N-trifluoroacetylpropargylamine, Pd (PPh$_3$)$_4$, CuI, triethylamine, DMF, room temperature (RT), 12 h; (ii) tert-butyldiphenylsilylchloride, pyridine, RT, 6 h; (iii) DMSO, AcOH, acetic anhydride, RT, 12 h; (iv) (a) SO$_2$Cl$_2$, 0° C. 1 h, (b) potassium p-toluenethiosulfonate, RT, 2 h, (c) sodium thiomethoxide, RT, 1.5 h.

Reagents and conditions used in Scheme 13 are: (i) methanolic ammonia, RT, 12 h; (ii) 10, NaHCO$_3$/Na$_2$CO$_3$ buffer (pH 9.2), acetonitrile (iii) Et$_3$N*3HF, THF, RT, 12 h; (iv) (a) 2-chloro-1H-1,3,2-benzodioxaphosphorin-4-one, pyridine, THF, 1 h, (b) tributylamine, tributyl ammonium pyrophosphate, 1.5 h; (c) tert-butyl hydrogen peroxide, 1 h; (v) aqueous TFA; (vi) ALEXA FLUOR® 568 NHS ester [1,10-Dihydro-2,2,10,10-tetramethyl-4,8-bis(sulfomethyl)-2H-pyrano[3,2-g:5,6-g']diquinolin-6-yl]benzenedicarboxylate-N-ethyl-N-(1-methylethyl)-2-propanamine, NaHCO$_3$/Na$_2$CO$_3$ buffer (pH 9.2).

Synthesis of N-(3-(1-((2R,4S,5R)-5-(((tert-butyldiphenylsilyl)oxy)methyl)-4-((methyldisulfaneyl)methoxy)tetrahydrofuran-2-yl)-2,4-dioxo-1,2,3,4-tetrahydropyrimidin-5-yl)prop-2-yn-1-yl)-2,2,2-trifluoroacetamide (65). A solution of Compound 4 (2.23 g, 3.31 mmol) in dichloromethane (40 mL) was cooled (−78° C.). Cyclohexene (1.67 mL, 16.5 mmol) and sulfuryl chloride (8.27 mL, 8.26 mmol) was added and the reaction mixture was stirred for 1 h until all starting material was consumed (as indicated by TLC). The reaction was warmed to room temperature and a solution of p-toluenethiosulfonate in acetonitrile (12 mL) was added, and stirred further for 2 hr. Sodium methoxide was then added to reaction mixture and the reaction mixture was stirred further for 1.5 h. The reaction mixture was filtered, and the filtrate was concentrated under vacuum. The residue was purified by flash chromatography on silica gel using ethyl acetate in hexanes (from 5% to 40%) to afford the product 5 as a white foam (2.02 g, 86%). 1H-NMR (CDCl3) δ 8.67 (br s, 1H, NH), 8.17 (s, 1H, H-6), 7.65-7.69 (m, 4H, Ar—H), 7.42-7.50 (m, 6H, Ar—H), 6.30 (dd, J=5.6 Hz and 2.8 Hz, 1H, H-1'), 4.76-4.86 (q, J=17.6 and 11.6 Hz, 2H, OCH$_2$S), 4.55-4.59 (m 1H, H-3'), 4.17-4.19 (m, 1H, H-4'), 4.04-4.06 (t, J=4.4 Hz, 2H, NCH$_2$), 3.98-4.02 (m, 1H, H-5'), 3.79-3.82 (m, 1H—H-5'), 2.54-2.59 (m, 1H, H-2'), 2.42 (s, 3H, SCH3), 2.09-2.17 (M, 1H, H-2'), Mass calcd. for C$_{32}$H$_{36}$F$_3$N$_3$O$_6$S$_2$Si, 707.18, found (M−H) 706.17.

5-(3-Aminoprop-1-yn-1-yl)-1-((2R,4S,5R)-5-(((tert-butyldiphenylsilyl)oxy)methyl)-4-((methyldisulfaneyl)methoxy)tetrahydrofuran-2-yl)pyrimidine-2,4(1H,3H)-dione (70). Compound 65 (2.00 g, 2.83 mmol) was dissolved in methanolic ammonia (40 mL) in a sealed tube and stirred overnight at room temperature. All volatiles were removed under vacuum and further dried on high vacuum for 1 h to afford 70 as a crude product, which was used as such for the next step.

tert-Butyl (2-((2-(((3-(1-((2R,4S,5R)-5-(((tert-butyldiphenylsilyl)oxy)-methyl)-4-((methyldisulfaneyl)methoxy)tetrahydrofuran-2-yl)-2,4-dioxo-1,2,3,4-tetrahydropyrimidin-5-yl)prop-2-yn-1-yl)carbamoyl)oxy)ethyl)disulfaneyl)

ethyl)carbamate (71). The crude 70 was dissolved in pyridine and the linker 10 (3.55 g, 8.49 mmol) was added to it. The reaction was stirred further overnight at room temperature. The reaction mixture was concentrated under vacuum and the residue was dissolved in ethyl acetate, washed with saturated sodium bicarbonate and brine. The organic layer was separated, dried over magnesium sulfate, and concentrated. The residue was purified by flash chromatography on silica gel using EA in hexanes (0 to 55%) to afford the product 71 as a white solid (1.18 g, 47%). $^1$H-NMR (CDCl$_3$) δ 8.05 (s, 1H, H-6), 7.67-7.70 (m, 4H, Ar—H), 7.42-7.51 (m, Ar—H-6H), 6.26-6.32 (m, 1H, H-1'), 4.75-4.85 (m, 2H, OCH$_2$S), 4.54 (d, J=5.6 HZ, 1H, HC-3;'), 4.24-4.30 (t, 2H, OCH$_2$), 4.14 9d, J=5.6 Hz, 1H, H-4'), 3.90-3.98 (m, 3H, NCH$_2$, OCH$_2$-5'), 3.74-3.80 (m, 1H, OCH$_2$-5'), 3.37-3.40, (m, 2H, NCH$_2$), 2.87-2.91 (t, J=6.0 HZ, 2H, SCH$_2$), 2.79-2.82 (t, J=6.4 Hz, 2H, SCH$_2$), 2.54-2.59 (m, 1H, H-2'), 2.42 (S, 3H, SCH$_3$), 2.111-2.18 (m, 1H, H-2'), 1.46 (s, 9H, O(CH$_3$)$_3$), 1.09 (s, 9H, C(CH$_3$)$_3$); Mass calcd. for C$_{40}$H$_{54}$N$_4$O$_9$S$_4$Si, 891.22, found (M–H) 890.27.

tert-Butyl (2-((2-(((3-(1-((2R,4S,5R)-5-(hydroxymethyl)-4-((methyldisulfaneyl)methoxy)tetrahydrofuran-2-yl)-2,4-dioxo-1,2,3,4-tetrahydropyrimidin-5-yl)prop-2-yn-1-yl)carbamoyl)oxy)ethyl)disulfaneyl)ethyl)carbamate (72). To a solution of 71 (1.15 g, 1.30 mmol) in anhyd. THF (10 mL) was added a solution of triethylamine-trihydrofluoride (3.55 g, 8.49 mmol) and the mixture was stirred at room temperature overnight. The volatiles were removed, and the oily residue was purified by flash chromatography on silica gel using methanol in dichloromethane (0 to 35%) to afford the product 72 as a white solid (0.34 g, 40%). $^1$H-NMR (CDCl$_3$) δ 8.35 (br s, 1H, NH), 8.20 (s, 1H, H-6), 6.20-6.23 (t, J=6.4 Hz, 1H, H-T), 5.50 (br s, 1H, OH), 4.82-4.92 (dd, J=11.6 Hz, 2H, OCH$_2$S), 4.57-4.58 (m, 1H, H-3'), 4.34-4.36 (t, J=6.0 Hz 1H, OCH$_2$), 4.17-4.19 (m, 3H, NCH$_2$ and H-4'), 3.96-4.04 (m, 1H, OCH$_2$-5'), 3.82-3.87 (m, 1H, OCH$_2$-5'), 3.4.43-4.38 (m, 2H, NCH$_2$), 2.87-2.91 (t, J=6.0 HZ, 2H, SCH$_2$), 2.79-2.82 (t, J=6.0 Hz, 2H, SCH$_2$), 2.45-55 (m, 4H, SCH$_3$, H-2'), 2.20-2.28 (m, 1H, H-2'), 1.46 (s, 9H, O(CH$_3$)$_3$), Mass calcd for C$_{24}$H$_{36}$N$_4$O$_9$S$_4$, 652.14, found (M–H) 651.1.

tert-Butyl (2-((2-(((3-(1-((2R,4S,5R)-5-(((hydroxy((hydroxy(phosphonooxy)phosphoryl)oxy)phosphoryl)oxy)methyl)-4-((methyldisulfaneyl)methoxy)tetrahydrofuran-2-yl)-2,4-dioxo-1,2,3,4-tetrahydropyrimidin-5-yl)prop-2-yn-1-yl)carbamoyl)oxy)ethyl)disulfaneyl)ethyl)carbamate (73). To a solution of 72 (0.15 g, 0.23 mmol) in anhydrous THF and pyridine (5 mL each), a solution of 2-chloro-1H-1,3,2-benzodioxaphosphorin-4-one (0.060 g, 0.29 mmol) dissolved in 1 mL THF was added under nitrogen and stirred for 1 h (when TLC didn't show any starting material was left). Tributylamine (0.17 g, 0.94 mmol) and tributyl-ammonium pyrophosphate (0.5 mmol solution in DMF, 0.7 mL, 0.35 mmol) were added subsequently and stirred further for 1.5 h. tert-Butyl hydroperoxide solution (5.5 m solution in decane, 210 μl, 1.1 mmol) was added to reaction and stirred further for 1 h. The reaction was then quenched with water and left overnight. The reaction mixture was concentrated, and the residue was purified by reverse phase HPLC using Hamilton PRP-column (21.2×250 mm). A gradient of triethylammonium bicarbonate (A, 25 mM) in acetonitrile (B, 0-20%) in 30 min. afforded the product 73. Mass calcd. for C$_{24}$H$_{39}$N$_4$O$_{18}$P$_3$S$_4$, 892.04; found (M-1) 891.03.

2-((2-Aminoethyl)disulfaneyl)ethyl (3-(1-((2R,4S,5R)-5-(((hydroxy((hydroxy(phosphonooxy)phosphoryl)oxy)phosphoryl)oxy)methyl)-4-((methyldisulfaneyl)methoxy)tetrahydrofuran-2-yl)-2,4-dioxo-1,2,3,4-tetrahydropyrimidin-5-yl)prop-2-yn-1-yl)carbamate (74). To a cooled solution of 13 (33.30 μmols) in water was added an aqueous trifluoroacetic acid solution (410 μL in 52 μL water) and the resulting mixture was stirred overnight. The mixture was purified by reverse phase HPLC using Hamilton PRP-column (21.2× 250 mm). A gradient of and triethylammonium bicarbonate (A, 25 mM) in acetonitrile (B, 0-20%) in 30 minutes afforded the product 74. Mass calcd. for C$_{19}$H$_{31}$N$_4$O$_{16}$P$_3$S$_4$, 791.98, found (M-1) 790.98.

(6-(3-carboxy-4-((2-((2-(((3-(1-((2R,4R,5R)-5-(((hydroxy((hydroxy(phosphonooxy)phosphoryl)oxy)phosphoryl)oxy)methyl)-4-((methyldisulfaneyl)methoxy)tetrahydrofuran-2-yl)-2,4-dioxo-1,2,3,4-tetrahydropyrimidin-5-yl)prop-2-yn-1-yl)carbamoyl)oxy)ethyl)disulfaneyl)ethyl)carbamoyl)phenyl)-2,2,10,10-tetramethyl-8-(sulfomethyl)-10,11-dihydro-2H-pyrano[3,2-g:5,6-g']diquinolin-1-ium-4-yl)methanesulfonate (75). To a solution of 74 (1.03 μM) in sodium carbonate/sodium bicarbonate buffer (pH 9.2, 280 μL), a solution of ALEXA FLUOR® 568 NHS ester [1,10-Dihydro-2,2,10,10-tetramethyl-4,8-bis(sulfomethyl)-2H-pyrano[3,2-g:5,6-g']diquinolin-6-yl]benzenedicarboxylate-N-ethyl-N-(1-methylethyl)-2-propanamine (2 mg, 2.5 μM) in DMSO (50 μL) was added. The reaction was stirred overnight. The crude product was purified by reverse phase HPLC using 50 mM triethylammonium bicarbonate as buffer A and acetonitrile as buffer B and using a gradient of 0-3-25% B in 30 min. The product 75 was a reddish powder and was characterized by LCMS, Mass calcd. for C$_{52}$H$_{59}$N$_6$O$_{26}$P$_3$S$_6$, 1468.10, found (M-1) 1467.10.

Enzymatic Incorporation and Cleavage Studies: S-((((2R,3S,5R)-5-(5-(3-((tert-butoxycarbonyl)amino)prop-1-yn-1-yl)-2,4-dioxo-3,4-dihydropyrimidin-1 (2H)-yl)-2-(((hydroxy((hydroxy(phosphonooxy)phosphoryl)oxy)phosphoryl)oxy)methyl)tetrahydrofuran-3-yl)oxy)methyl) ethanethioate (60), a model compound, was synthesized similar to conditions of the relevant reactions disclosed in Schemes 2-4.

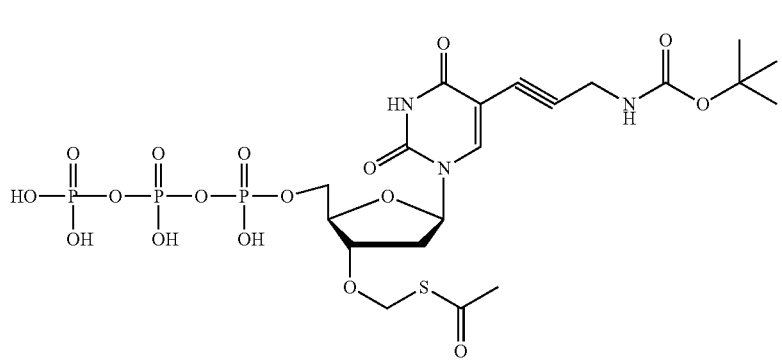

Figure 2:
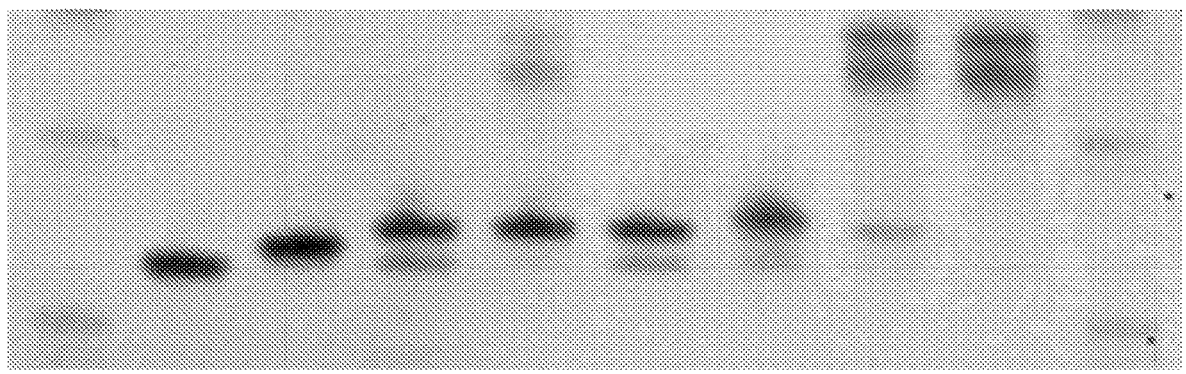
FIG. 2 shows primer extension with compound 60 into a growing DNA chain.

FIG. 2 shows that compound 60 can be used in enzymatic incorporation in the presence of DNA polymerase ("CENT1") (lane 3), blockage of further extension after incorporation of the terminator (lane 4) by treating the enzymatic product thus obtained in a "runaway" reaction in the presence of all four unmodified dNTPs and a polymerase, cleavage of the label and the blocking group (lane 5), and further extension by the next base added (lane 6) after the cleavage.

Figure 4:
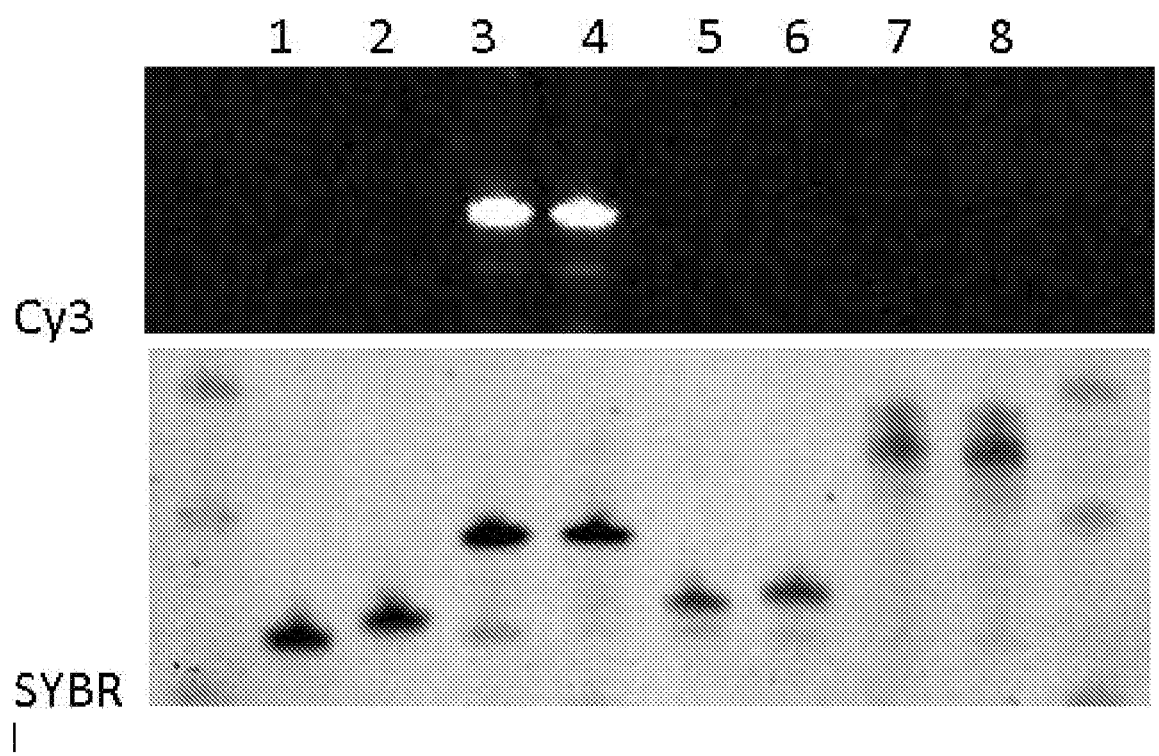
FIG. 4 shows primer extension with compound 75 into a growing DNA chain.

Enzymatic Incorporation and Cleavage Studies: (6-(3-carboxy-4-((2-(((3-(1-((2R,4R,5R)-5-(((hydroxy((hydroxy(phosphonooxy)phosphoryl)oxy)phosphoryl)oxy)-methyl)-4-((methyldisulfaneyl)methoxy)tetrahydrofuran-2-yl)-2,4-dioxo-1,2,3,4-tetrahydropyrimidin-5-yl)prop-2-yn-1-yl)carbamoyl)oxy)ethyl)disulfaneyl)ethyl)carbamoyl)-phenyl)-2,2,10,10-tetramethyl-8-(sulfomethyl)-10,11-dihydro-2H-pyrano[3,2-g:5,6-g']diquinolin-1-ium-4-yl) methanesulfonate (75), showed excellent enzymatic incorporation in FIG. 4 (lane 3) with compound 75 in the presence of a DNA polymerase ("CENT1"). It also showed excellent blockage (lane 4) of further extension after the incorporation of the terminator by treating the enzymatic product thus obtained in a "runaway" reaction (in the presence of all four unmodified dNTPs and a DNA polymerase). Then simultaneous cleavage of the 3' blocking group along with the labeled linker tag can be observed after the treatment with DTT (lane 5), and further extension with on base added (lane 6), as well continued extension in a "runaway" reaction in the presence of all four unmodified dNTPs and a DNA polymerase (lanes 7 and 8).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A nucleoside 5'-triphosphate analog according to formula (II):

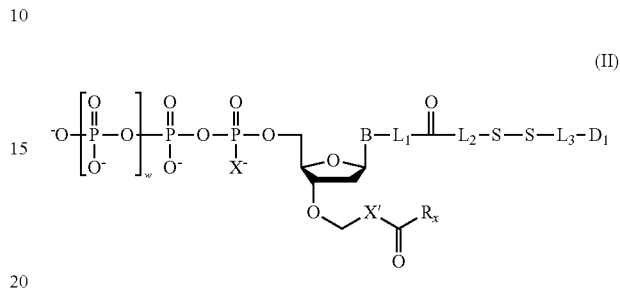

or a salt or protonated form thereof, wherein:
X is O;
X' is O or S;
w is 1;
base B is a nucleotide base or an analog thereof;
$R_x$ is H or $C_{1-6}$ alkyl, wherein the $C_{1-6}$ alkyl is unsubstituted or substituted by 1-3 groups selected from the group consisting of F and Cl;
$L_1$ is a first linker group and $L_1$ is 3-25 atoms in length;
$L_2$ is a second linker group and $L_2$ is

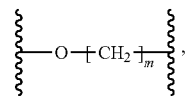

and m is 2 or 3;
$L_3$ is a third linker group and $L_3$ is 4-47 atoms in length;
$D_1$ is a fluorophore.

2. A nucleoside 5'-triphosphate, wherein the nucleoside 5'-triphosphate analog is according to formula (IV):

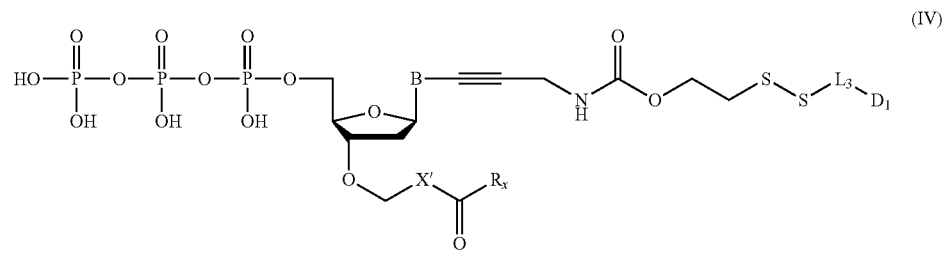

or a salt or protonated form thereof, wherein:
X' is O or S
$R_x$ is H or $C_{1-6}$ alkyl, wherein the $C_{1-6}$ alkyl is unsubstituted or substituted by 1-3 groups selected from the group consisting of F and Cl;
base B is selected from the group consisting of

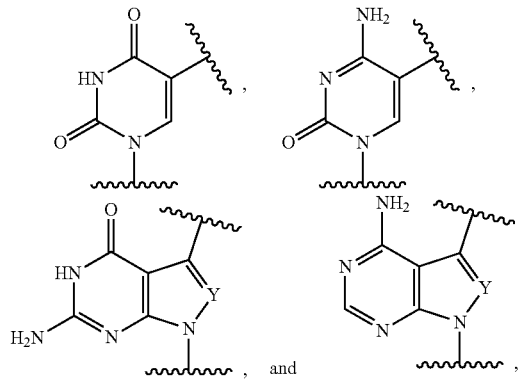

and Y is CH or N; and
$L_3$ is a third linker group and $L_3$ is 4-47 atoms in length.

3. The nucleoside 5'-triphosphate analog of claim 2, wherein $L_3$ comprises alkylene, alkenylene, cycloalkylene with a 3-7 membered ring, alkynylene, arylene, heteroarylene, heterocyclene with a 5-12 membered ring comprising 1-3 atoms of N, O or S, —O—, —NH—, —S—, —N($C_{1-6}$ alkyl)—, —C(=O)—, —C(=O)NH—, or combinations thereof.

4. The nucleoside 5'-triphosphate analog of claim 2, wherein $R_x$ is H or methyl.

5. The nucleoside 5'-triphosphate analog of claim 1, wherein:
$L_1$ is

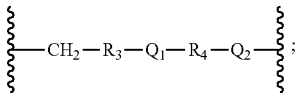

n is 0 or 1;
$R_x$ is H or methyl;
$R_1$ is

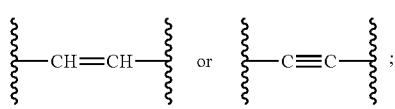

$R_2$ is

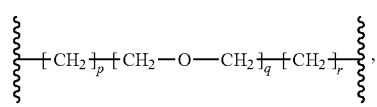

wherein p is independently 0-3, q is independently 0-12, and r is independently 1-3; and
Z is O or NH.

6. The nucleoside 5'-triphosphate analog of claim 5, wherein:
$L_3$ is

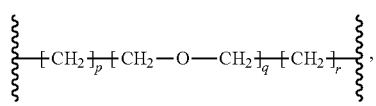

$Q_1$ and $Q_2$ are independently selected from the group consisting of a bond,

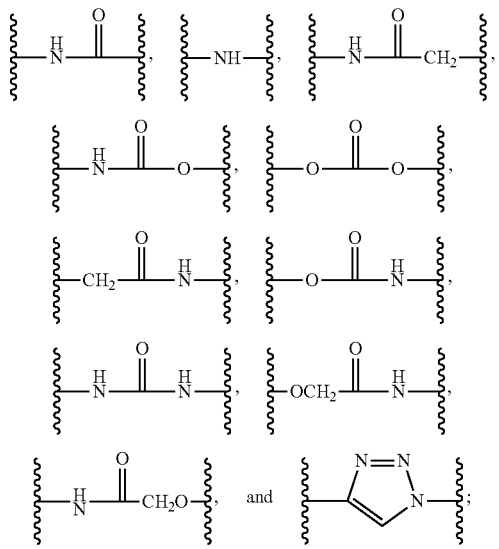

and
$R_3$ and $R_4$ are independently

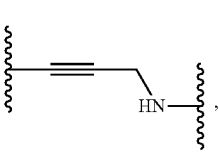

wherein p is independently 0-3, q is independently 0-12, and r is independently 1-3.

7. The nucleoside 5'-triphosphate analog of claim 1, wherein:
w is 1;
X is O;
X' is O or S;
$R_x$ is H or methyl;
$L_1$ is , or -continued
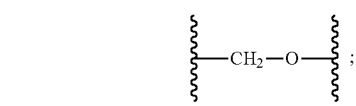
L₂ is
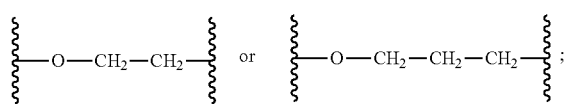
L₃ is
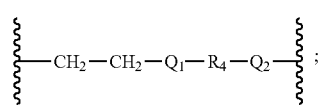
R₄ is
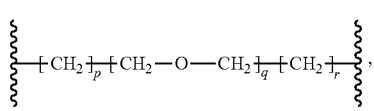
wherein p is 0-3, q is 0-12, and r is 1-3; and
Q₁ and Q₂ are independently selected from the group consisting of a bond,
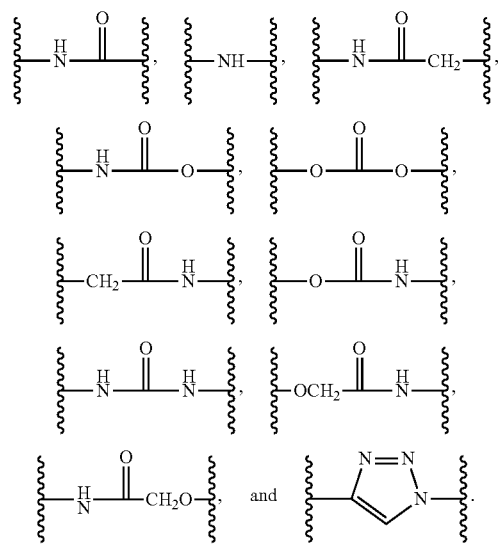
8. The nucleoside 5′-triphosphate analog of claim 2, wherein:
X′ is O or S;
$R_x$ is H or methyl;
L₁ is
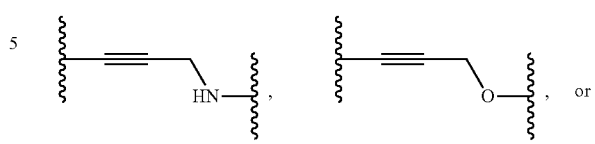
L₂ is
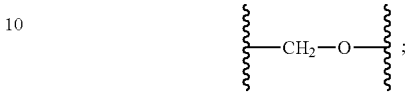
L₃ is
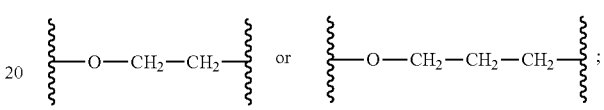
R₄ is
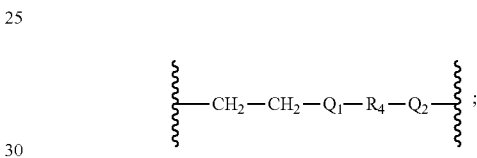
wherein p is 0-3, q is 0-12, and r is 1-3; and
Q₁ and Q₂ are independently selected from the group consisting of a bond,
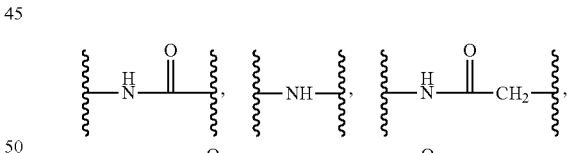
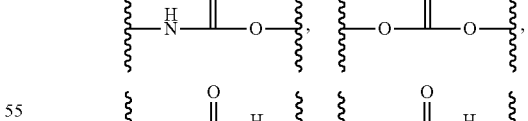
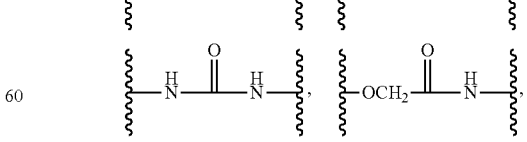
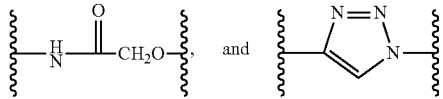

9. The nucleoside 5'-triphosphate analog of claim 1, wherein:

$L_3$ is

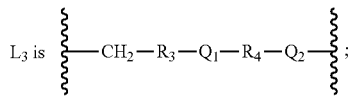

$Q_1$ and $Q_2$ are independently selected from the group consisting of a bond,

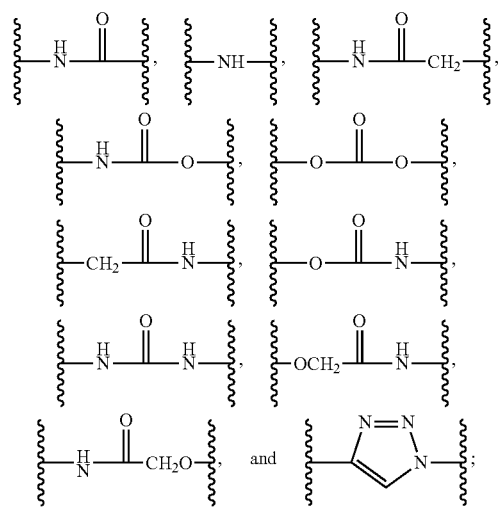

and $R_3$ and $R_4$ are independently

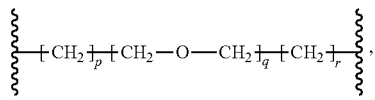

wherein p is independently 0-3, q is independently 0-12, and r is independently 1-3.

10. The nucleoside 5'-triphosphate analog of claim 2, wherein:

$L_3$ is

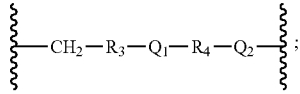

$Q_1$ and $Q_2$ are independently selected from the group consisting of a bond,

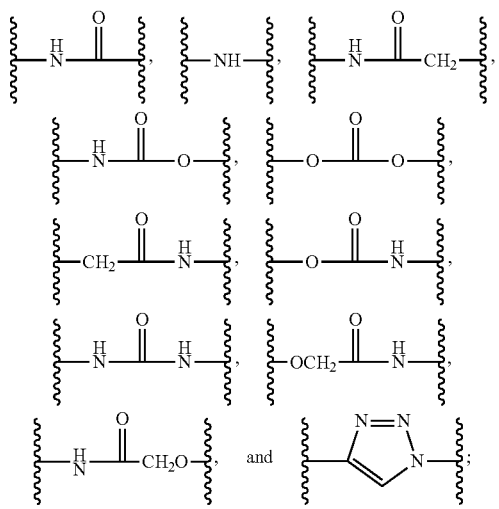

and $R_3$ and $R_4$ are independently

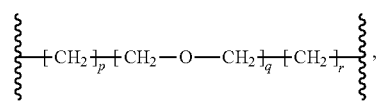

wherein p is independently 0-3, q is independently 0-12, and r is independently 1-3.

* * * * *